United States Patent [19]

Grate et al.

[11] Patent Number: 5,506,363
[45] Date of Patent: Apr. 9, 1996

[54] CATALYTIC SYSTEM FOR OLEFIN OXIDATION TO CARBONYL PRODUCTS

[75] Inventors: John H. Grate; David R. Hamm, both of Mountain View, Calif.; Robert J. Saxton, West Chester, Pa.; Mark T. Muraoka, Mountain View, Calif.

[73] Assignee: Catalytica, Inc., Mountain View, Calif.

[21] Appl. No.: 934,643

[22] PCT Filed: Mar. 5, 1991

[86] PCT No.: PCT/US91/01508

§ 371 Date: Sep. 4, 1992

§ 102(e) Date: May 24, 1991

[87] PCT Pub. No.: WO91/13851

PCT Pub. Date: Sep. 19, 1991

Related U.S. Application Data

[63] Continuation-in-part of Ser. No. 489,806, Mar. 5, 1990, abandoned.

[51] Int. Cl.$^6$ .................................................. C07C 45/34
[52] U.S. Cl. .......................................... 568/401; 568/400
[58] Field of Search ................................... 568/400, 401

[56] References Cited

U.S. PATENT DOCUMENTS

| | | | |
|---|---|---|---|
| 3,119,875 | 1/1964 | Steinmetz | 260/604 |
| 3,122,586 | 2/1964 | Berndt | 260/586 |
| 3,154,586 | 10/1964 | Bander | 260/596 |
| 3,485,877 | 12/1969 | Hargis | 260/604 |
| 4,146,574 | 3/1979 | Onada | 423/299 |
| 4,404,397 | 9/1983 | Daniel | 562/546 |
| 4,434,082 | 2/1984 | Murtha | 502/164 |
| 4,448,892 | 5/1984 | Kukes | 502/164 |
| 4,507,506 | 3/1985 | Shioyama | 568/401 |
| 4,507,507 | 3/1985 | Murtha | 568/401 |
| 4,532,362 | 7/1985 | Kukes | 568/401 |
| 4,550,212 | 10/1985 | Shioyama | 568/401 |
| 4,720,474 | 1/1988 | Vasilevskis | 502/165 |
| 4,723,041 | 2/1988 | Vasilevskis | 568/401 |
| 4,762,817 | 8/1988 | Logsdon | 502/329 |
| 5,004,845 | 4/1991 | Bradley | 568/885 |

FOREIGN PATENT DOCUMENTS

| | | |
|---|---|---|
| 828603 | 10/1975 | Belgium . |
| 0031729 | 7/1981 | European Pat. Off. . |
| 123085 | 11/1976 | German Dem. Rep. . |
| 61-43131 | 8/1984 | Japan . |
| 1508331 | 4/1978 | United Kingdom . |

OTHER PUBLICATIONS

Smidt, J., et al., "The Oxidation of Olefins with Palladium Chloride Catalysts," *Angew. Chem. Internat. Edit.* (1962) vol. 1, pp. 80–88.
Miller, S. A., editor, *Ethylene and Its Industrial Derivatives* (published by Ernest Benn Ltd, London, 1969), Chapter 8, pp. 639–689.
Matveev, K. I., et al., *Kinetika i Kataliz* (1977) vol. 18, No. 2, pp. 380–386. The English translation edition, "Kinetics of Oxidation of Ethylene to Acetaldehyde by Phosphomolyb-dicvanadic Heteropolyacids in the Presence of a Pd(II) Aquo Complex," pp. 320–326, is provided.
Polotebnova, N. A., et al., *Zh. Neorg. Khim.* (1973) 18:413. The English translation edition, "Properties of Vanadomolybdophosphoric Acids with Varying Concentrations of Molybdenum and Vanadium," Russian Journal of Inorganic Chemistry (1973) 18(2):216–219, is provided.
Zangen, M., "Solvent Extraction From Molten Salts. V. Zinc(II) Chloride, Bromide, and Iodide," *Inorg. Chem.*, (1968) 7(1):133–138. P. 137 is provided.
Matveev, K. I., *Kinetika i Katal.* (1977) vol. 18, No. 4, pp. 862–877. The English translation edition, "Development of New Homogeneous Catalysts for the Oxidation of Ethylene to Acetaldehyde," pp. 716–727, is provided.
Cihova, M., et al., "Catalytic Oxidation of Octene–1 in the Presence of Palladium(II) Salts and Heteropolyacids," *Reaction Kinetics and Catalysis Letters*, (1981) 16:383–386.
Cihova, M., et al., "Oxidácia 1–okténu na 2–octanón v prietočnom reaktore," *Ropa Uhlie* (1986) 28:297–302. An English language abstract (Chem. Abstr. 107(1):6740r) is attached.
El Ali, Bassam, et al., "Oxydation catalytique de l'octène–1 en présence de complexes de rhodium(III) ou de palladium(II associés à des acides phosphomolybdovanadiques et au dioxygène," *J. Organomet. Chem.* (1987) 327:C9–C14. The publication includes an English language abstract.
Kuznetsova, L. I., et al., "Catalytic Oxidation of Vanadyl Salts by Oxygen in the Presence of Sodium Molybdate," *Reaction Kinetics and Catalysts Letters* (1975) 3(3):305–310.
Kuznetsova, L. I., et al., *Koordinatsionnaya Khimiya* (1977) vol. 3, No. 1, pp. 51–58. The English translation edition, "State of Phosphomolybdovanadium Heteropoly Blue Oxides in Aqueous Solution," pp. 39–44, is provided.
Berdnikov, V. M. et al., *Koordinatsionnaya Khimiya* (1979) vol. 5, No. 1, pp. 78–85. The English translation edition "Kinetics and Mechanism of the Oxidation of Reduced Molybdovanadophosphoric Heteropolyacids with Oxygen (List continued on next page.)

Primary Examiner—James H. Reamer
Attorney, Agent, or Firm—John H. Grate

[57] ABSTRACT

The present invention provides aqueous catalyst solutions useful for oxidation of olefins to carbonyl products, comprising a palladium catalyst, a polyoxoacid or polyoxoanion oxidant comprising vanadium, and chloride ions. It also provides processes for oxidation of olefins to carbonyl products, comprising contacting olefin with the aqueous catalyst solutions of the present invention. It also provides processes for oxidation of olefins to carbonyl products by dioxygen, comprising contacting olefin with the aqueous catalyst solutions of the present invention, and further comprising contacting dioxygen with the aqueous catalyst solutions. The present invention also provides a process for the oxidation of palladium(0) to palladium(II) comprising contacting the palladium(0) with an aqueous solution comprising chloride ions and a polyoxoacid or polyoxoanion oxidant comprising vanadium.

22 Claims, 4 Drawing Sheets

OTHER PUBLICATIONS

Hexavanadic Heteropoly Blues," pp. 60–66, is provided.

Kozhevnikov, I. V., *Izvestiya Akademii Nauk SSSR, Seriya Khimicheskaya* (1981) No. 11., pp. 2428–2435. The English translation edition, "Mechanism of the Oxidation of 12–Molybovanadophosphate Blues by Oxygen in Aqueous Solution," pp. 2001–2007, is provided.

Burov, Y. V., et al. *Izvestiya Akademii Nauk SSSR, Seriya Khimicheskaya* (1980) No. 7, pp. 1469–1473. The English translation edition, "Steady–Flow Investigation of the Kinetics of the Reaction Between $VO^{2+}$ and Phosphorus–Molybdenum–Vanadium Heteropoly Anions," pp. 1017–1021, is provided.

Kuznetsova, L. I., et al., "Mechanism of Oxidation of Molybdovanadophosphoric Heteropoly Blues by Molecular Oxygen. Trivanadium Heteropoly Blue," *Reaction Kinetics and Catalysis Letters* (1981) 17:401–406.

Davison, S. F., et al., "Phosphomolybdic Acid as a Reoxidant in the Palladium(II)–catalysed Oxidation of But–1–ene to Butan–2–one," *J. Chem. Soc. Dalton Trans.* (1984) pp. 1223–1228.

Davison, S. F., Ph.D., Dissertation, "Palladium and Heteropolyacid Catalyzed Oxidation of Butene to Butanone," University of Sheffield, 1981. The Summary, Table of Contents, pp. 63 and 77, are provided.

Pope, Michael Thor, *Inorganic Chemistry Concepts 8: Heteropoly and Isopoly Oxometalates,* published by Springer–Verlag, NY. A copy of the Table of Contents is provided.

Koscielski, T., et al., "Catalytic Hydrogenation on Raney Nickel Catalyst Modified by Chromium Hydroxide Deposition," *Applied Catalysis* (1989) 49:91–99.

*Sixth World Petroleum Congress Proceedings, Section IV,* Paper 40, pp. 461–466, Frankfurt, 19–26 Jun. 1963.

"New Process for Acetone and MEK: A Special Report: 6th World Petroleum Congress," in *Hydrocarbon Processing & Petroleum Refiner* (1963) vol. 42, pp. 149–152.

"Wacker Process Can Make Acetone, MEK," in *Chemical and Engineering News*, 8 Jul. 1963, pp. 50–51.

Bonnier, J–M., et al., "Raney Nickel as a Selective Catalyst for Aldehyde Reduction in the Presence of Ketones," *Applied Catalysis* (1987) 30:181–184.

CATALYTIC SYSTEM FOR OLEFIN OXIDATION TO CARBONYL PRODUCTS

CROSS-REFERENCES TO RELATED APPLICATIONS

This patent application is a continuation-in-part of U.S. patent application Ser. No. 489,806 filed Mar. 5, 1990 now abandoned which is incorporated by reference entirely. Related U.S. patent applications Ser. Nos. 07/689,050, 07/689,048, and 07/675,937, co-filed with this application on Sep. 4, 1992, are each incorporated by reference entirely.

FIELD OF THE INVENTION

This invention relates generally to oxidation of olefins to carbonyl compounds. More specifically, it relates to oxidation of olefins to carbonyl compounds by polyoxoanion oxidants in aqueous solution, catalyzed by palladium. In another aspect, it relates to reoxidation of reduced polyoxoanions in aqueous solution by reaction with dioxygen. It further relates to an overall process for the oxidation of olefins to carbonyl compounds by dioxygen catalyzed by palladium and polyoxoanions in aqueous solution.

BACKGROUND OF THE INVENTION

The catalyst solutions and the processes of the present invention are useful for the production of aldehydes, ketones, and carboxylic acids, which are chemicals of commerce and/or feedstocks for the production of chemicals and materials of commerce. For example, acetone, methyl ethyl ketone and methyl isobutyl ketone are used as solvents. Acetaldehyde is used in the production of acetic acid, polyols, and pyridines. Acetic acid is used in the production of vinyl acetate, cellulose acetate, and various alkyl acetate esters which are used as solvents. Acetone is used in the production of methylmethacrylate for polymethylmethacrylate. Cyclohexanone is used in the production of caprolactam for nylon-6 and adipic acid for nylon-6,6. Other cyclic ketones can be used for the production of other nylon-type polymers.

Acetaldehyde is industrially produced by the Wacker oxidation of ethylene by dioxygen, which uses an aqueous catalyst system of palladium chloride, copper chloride, and hydrochloric acid to accomplish the following net conversion:

$$C_2H_4 + \tfrac{1}{2}O_2 \rightarrow CH_3CHO \quad (1)$$

Reviews of the Wacker process chemistry and manufacturing processes for the direct oxidation of ethylene to acetaldehyde can be found in "The Oxidation of Olefins with Palladium Chloride Catalysts", *Angew. Chem. internat. Edit.*, Vol. 1 (1962), pp. 80–88, and in Chapter 8 of Ethylene and its Industrial Derivatives, S. A. Miller ed., Ernest Benn Ltd., London, 1969, each of which is incorporated by reference entirely. Aspects of Wacker technology are also disclosed in U.S. Pat. Nos. 3,122,586, 3,119,875, and 3,154,586, each incorporated by reference entirely.

In the Wacker process chemistry, ethylene is oxidized by cupric chloride in aqueous solution, catalyzed by palladium:

$$C_2H_4 + 2\,Cu^{II}Cl_2 + H_2O \xrightarrow{Pd^{II}Cl_4^{=}} CH_3CHO + 2\,Cu^ICl_2^- + 2\,H^+ \quad (2)$$

In a typical manufacturing operation, copper is present in the aqueous solution at concentrations of about 1 mole per liter, total chloride is present at concentrations of about 2 moles per liter, and the palladium catalyst is present at concentrations of about 0.01 moles per liter. Under these conditions, palladium(II) exists predominantly as the tetrachloropalladate ion, $PdCl_4^{=}$. Cuprous chloride resulting from the oxidation of ethylene is solubilized in the aqueous solution by the co-produced hydrochloric acid, as the dichlorocuprate ion, $Cu^ICl_2^-$. In a subsequent Wacker chemistry step, this reduced copper is reoxidized by reaction with dioxygen:

$$2\,Cu^ICl_2^- + 2H^+ + \tfrac{1}{2}O_2 \rightarrow 2\,Cu^{II}Cl_2 + H_2O \quad (3)$$

(Reactions (2) and (3) combined give overall reaction (1))

Two acetaldehyde manufacturing processes, a two-stage process and a one-stage process, have been developed and operated using the Wacker system chemistry. In the two-stage process, ethylene oxidation by cupric chloride, reaction (2), and reoxidation of cuprous chloride by air, reaction (3), are conducted separately, with intermediate removal of the acetaldehyde product from the aqueous solution. The reoxidized aqueous solution is recycled to the ethylene oxidation stage. The reactions are conducted at temperatures of about 100 to 130° C. in reactors which, by providing very efficient gas-liquid mixing, result in high rates of diffusion (mass transfer) of the reacting gas into the aqueous solution. Under these conditions, about 0.24 moles ethylene per liter of solution can be reacted within about 1 minute in the ethylene reactor, corresponding to an average ethylene reaction rate of about 4 (millimoles/liter)/second. With a typical palladium concentration of about 0.01 moles per liter, this corresponds to a palladium turnover frequency (a measure of catalyst activity) of about 0.4 (moles $C_2H_4$/mole Pd)/second. In the air reactor, about 0.12 moles dioxygen per liter of solution can be reacted within about 1 minute, corresponding to an average dioxygen reaction rate of about 2 (millimoles/liter)/second.

In the one-stage process, ethylene and dioxygen are simultaneously reacted with the aqueous solution, from which acetaldehyde is continuously removed.

Palladium catalyzes the oxidation of ethylene by cupric chloride (reaction (2)) by oxidizing ethylene (reaction (4)) and then reducing cupric chloride (reaction (5)):

$$C_2H_4 + PdCl_4^{=} + H_2O \rightarrow CH_3CHO + Pd^0 + 2H^+ + 4Cl^- \quad (4)$$

$$Pd^0 + 4Cl^- + 2\,Cu^{II}Cl_2 \rightarrow PdCl_4^{=} + 2\,Cu^ICl_2^- \quad (5)$$

Functionally, the copper chlorides mediate the indirect reoxidation of the reduced palladium(0) by dioxygen via reaction (5) plus reaction (3). Direct oxidation of palladium(0) by dioxygen is thermodynamically possible but is far too slow for practical application.

The overall rate of oxidation of ethylene by the Wacker system is limited by the rate of oxidation of ethylene by the tetrachloropalladate (reaction (4)). The reaction rate is inversely dependent on both the hydrogen ion concentration and the square of the chloride ion concentration, having the following concentration dependencies:

$$C_2H_4\ \text{reaction rate} \propto [PdCl_4^{=}][C_2H_4]/[H^+][Cl^-]^2 \quad (6)$$

Two chloride ions must be dissociated from tetrachloropalladate before palladium(II) productively binds both the substrates of reaction (4), ethylene and water. Said another way, chloride competes with the two substrates for the third and fourth coordination sites on palladium(II). This occurs by the following equilibria:

$$PdCl_4^= + C_2H_4 \rightleftharpoons PdCl_3(C_2H_4)^- + Cl^- \quad (7)$$

$$PdCl_3(C_2H_4)^- + H_2O \rightleftharpoons PdCl_2(C_2H_4)(H_2O) + Cl^- \quad (8)$$

Not only does chloride ion competitively inhibit the binding of substrates, but the remaining bound chlorides in intermediate complexes diminish the electrophilicity (positive charge density) at the palladium(ll) center which drives the overall reaction to palladium(0). The subsequent reaction steps, hydrogen ion dissociation (reaction (9)) and collapse of the resulting intermediate to products (reaction (10)), are less favored for these chloride-bound intermediate complexes that they would be for their aquated counterparts with fewer or no bound chlorides.

$$PdCl_2(C_2H_4)(H_2O) \rightleftharpoons PdCl_2(C_2H_4)(OH)^- + H^+ \quad (9)$$

$$PdCl_2(C_2H_4)(OH)^- \rightarrow CH_3CHO + Pd^0 + H^+ + 2Cl^- \quad (10)$$

A step in reaction (10) is turnover rate-limiting for reaction (4) in the Wacker system (reactions (7), (8), (9), and (10) give reaction (4)), so that the disfavoring influences of chloride ion on reaction (10) and on the preceding equilibria (7), (8), and (9) are manifested in the obtained palladium catalyst activity.

However, the Wacker system requires a high total chloride concentration to function effectively. The chloride to copper ratio must be greater than 1:1 for the copper(ll) to be soluble $CuCl_2$ rather than insufficiently soluble copper hydroxide chlorides, and for copper(I) to be soluble $CuCl_2^-$ rather than insoluble CuCl. Moreover, in the absence of chloride, aquated copper(ll) is thermodynamically impotent for oxidizing palladium(0) metal to aquated palladium(ll). Chloride complexation raises the copper(ll)/copper(I) oxidation potential and lowers the palladium(ll)/palladium(0) oxidation potential, so that at high chloride ion concentrations the forward reaction (5) becomes thermodynamically favored.

The Wacker system has several undesirable characteristics in the manufacture of acetaldehyde. These undesirable characteristics result from the high cupric chloride concentration. The aqueous cupric chloride solution is extremely corrosive; manufacturing process equipment is constructed of expensive corrosion resistant materials, usually titanium. The manufacturing processes typically convert a percent or more of the ethylene feed to chlorinated organic by-products. These chlorinated organic by-products are hygienically and environmentally objectionable. Their adequate separation from the acetaldehyde product and from other gas and liquid streams which exit the process and their proper destruction or disposal add to the operating costs of the manufacturing processes.

These chlorinated organic by-products have a number of mechanistic origins. Some result from direct additions of hydrochloric acid to ethylene, giving ethylchloride, and to olefinic by-products. Others result from palladium centered oxychlorination, for example, 2-chloroethanol from ethylene. The predominant origin of chlorinated organic by-products is oxychlorination by cupric chloride, most arise from copper centered oxychlorination of acetaldehyde, giving chloroacetaldehydes, and further reactions of the chloroacetaldehydes. Accordingly, we determined that most of the objectionable chlorinated organic by-product yield results not simply from the presence of chloride, but from the combination of chloride and copper.

Aqueous palladium(II) salts also oxidize higher olefins to carbonyl compounds according to equation (11), where R, R', and R" are hydrocarbyl substituent groups and/or hydrogen (R=R'=R"=H for ethylene):

$$RR'C=CHR'' + Pd^{II} + H_2O \longrightarrow \quad (11)$$

$$RR'CH-\overset{O}{\underset{\|}{C}}R'' + Pd^0 + 2H^+$$

As examples, aqueous palladium(II) salts oxidize propylene to acetone (and some propionaldehyde), butenes to methyl ethyl ketone (and some butyraldehyde), and cyclohexene to cyclohexanone. Higher olefins can be oxidized by dioxygen using the Wacker system, but serious problems encountered in using the Wacker system to oxidize higher olefins have effectively prohibited any other significant application to manufacturing carbonyl compounds.

The rate of oxidation of the olefinic double bond by aqueous palladium(II) salts generally decreases as the number and/or size of hydrocarbyl substituents increases. This decrease in rate is particularly severe with $PdCl_4^=$ in the Wacker system, due to the competition of chloride with the more weakly binding higher olefins for palladium(II) complexation and due to the lowered electrophilicity of multiply chloride-bound olefin-palladium(II) intermediates. Consequently, much higher palladium concentrations (with its concomitant palladium investment) are necessary to obtain volumetric production rates of higher carbonyl compounds comparable to acetaldehyde production rates.

An even more prohibitive disadvantage of the Wacker system for manufacturing carbonyl compounds from higher olefins is the substantially increased production of chlorinated organic by-products. Higher olefins are more susceptible to palladium centered oxychlorination, which chlorinates not only at olefinic carbon atoms but also at allylic carbon atoms. Higher aldehydes and ketones having methylene groups adjacent to the carbonyl group are also more susceptible to cupric chloride mediated oxychlorination than is acetaldehyde. As a result, the productivity of the Wacker system for producing chlorinated organic by-products increases rapidly both with increasing number and size of hydrocarbyl substituents in the olefin.

Other, multistep manufacturing processes are typically used instead of the Wacker process to convert higher olefins into corresponding carbonyl compounds. For example, the manufacture of methyl ethyl ketone (2-butanone) involves the reaction of n-butenes with concentrated sulfuric acid to produce sec-butyl hydrogen sulfate and hydrolysis of sec-butyl hydrogen sulfate to obtain 2-butanol and diluted sulfuric acid. 2-butanol is catalytically dehydrogenated to produce methyl ethyl ketone. The diluted sulfuric acid must be reconcentrated for recycle.

Other carbonyl compounds are instead manufactured from starting materials more expensive than the corresponding higher olefin. For example, cyclopentanone is manufactured from adipic acid instead of from cyclopentene.

An effective method for the direct oxidation of higher olefins to carbonyl compounds by dioxygen has been long sought in order to enable more economical manufacturing of carbonyl compounds. Yet, in 30 years since the development of the Wacker system, no alternate palladium-based system for the oxidation of olefins by dioxygen which avoids the disadvantages and limitations of the Wacker system has been successfully applied in commercial manufacturing operation.

Systems have been proposed which use polyoxoanions, instead of cupric chloride, in combination with palladium to effect the oxidation of olefins.

U.S. Pat. No. 3,485,877, assigned to Eastman Kodak Company (hereafter, "Eastman patent") discloses a system for converting olefins to carbonyl compounds by contacting with an agent comprising two components, one of which is palladium or platinum, and the other is molybdenum trioxide or a heteropolyacid or salt thereof. This patent discloses that the so-called "contact agent" may be in an aqueous solution for a liquid phase process, but that it is advantageous and preferred to support the agent on a solid carrier for a vapor phase process in which gaseous olefin is contacted with the solid phase agent. The patent compares the oxidation of propylene with a liquid phase contact agent (in Example 16), to give acetone substantially free of byproducts with the oxidation of propylene in the vapor phase with a corresponding solid contact agent (in Example 10), to give acrolein. Apparently, the behavior of an olefin's liquid phase reaction with the disclosed aqueous contact agent solution cannot be predicted from the behavior of the olefin's vapor phase reaction with the analogous solid contact agent.

Eastman patent discloses that, when operating in the liquid phase, heteropolyacids or their salts, and particularly phosphomolybdic acid or silicomolybdic acid in water are preferred. Among the heteropolyacids disclosed, only phosphomolybdic acid and silicomolybdic acid are demonstrated by working example. No salts of heteropolyacids are so demonstrated. Phosphomolybdovanadic acid or salts thereof are nowhere mentioned in this patent.

Eastman patent also discloses the reaction in the presence of oxygen or oxygen containing gas. It also discloses periodic regeneration of the contact agent with air. However, the use of oxygen or air is demonstrated by working examples only for reactions of olefins in the vapor phase with solid phase contact agents.

We have found that oxygen reacts too slowly with reduced phosphomolybdic acid or silicomolybdic acid in aqueous solutions for such solutions to be practically useful in the industrial conversion of olefins to carbonyl compounds using oxygen or air as oxidant. In contrast, our reduced polyoxoanions comprising vanadium in aqueous solution of the present invention can react rapidly with oxygen or air.

In addition, Eastman patent discloses palladium chlorides among various preferred palladium or platinum components for the contact agent. Palladous chloride is predominantly used among the working examples. Eastman patent also discloses that it is possible to improve the action of the contact agent by incorporating small amounts of hydrochloric acid or ferric chloride. However, the only demonstration by working example adds ferric chloride in a solid phase contact agent for a vapor phase reaction (Example 19) to obtain higher reaction rates (conversion and space time yield). No such demonstration, nor result, is given for addition of hydrochloric acid to either a solid or a liquid phase contact agent, nor for addition of either hydrochloric acid or ferric chloride to a liquid phase contact agent.

Belgian Patent No. 828,603 and corresponding United Kingdom Patent No. 1,508,331 (hereafter "Matveev patents") disclose a system for the liquid phase oxidation of olefins employing an aqueous solution combining: a) a palladium compound; b) a reversible oxidant which has a redox potential in excess of 0.5 volt and which is a mixed isopolyacid or heteropolyacid containing both molybdenum and vanadium, or a salt of said polyacid; and, c) an organic or mineral acid other than said mixed isopolyacid or heteropolyacid, which organic or mineral acid is free of halide ions and is unreactive (or at most weakly reactive) with the palladium compound. The disclosed system differs from that of Eastman patent by simultaneously employing only certain heteropolyacids and mixed isopolyacids and adding certain other acids to the solution. Those certain polyacids employed contain both molybdenum and vanadium. Those certain other acids added are not the polyacid and are free of halide ions.

Matveev patents disclose that only the certain polyacids, containing both molybdenum and vanadium, function satisfactorily in the system as reversibly acting oxidants, wherein the reduced form of the oxidant is reacted with dioxygen to regenerate the oxidant. The patent further discloses that the polyacid used contains from 1 to 8 vanadium atoms, more preferably 6 atoms, in a molecule with molybdenum. According to the disclosure, as the number of vanadium atoms increases from 1 to 6 the principal characteristics of the catalyst, such as its activity, stability, and olefin capacity, increase.

Matveev patents disclose typical heteropolyacids of a formula $H_n[PMo_pV_qO_{40}]$, in which n=3+q, p=12-q, q=1 to 10. Matveev patents disclose that the catalyst is prepared, in part, by dissolving in water, oxides, salts, and/or acids of the elements forming the polyacid and then adding to the solution, the specified other organic or mineral acid. A preferred catalyst is said to be prepared by dissolving in water $Na_3PO_4$ (or $Na_2HPO_4$, or $NaH_2PO_4$, or $H_3PO_4$, or $P_2O_5$), $MoO_3$ (or $Na_2MoO_4$, or $H_2MoO_4$), $V_2O_5$ (or $NaVO_3$), and $Na_2CO_3$ (or $NaOH$) to form a solution, adding $PdCl_2$ to the solution of molybdovanadophosphoric acid, and then adding the other acid. (Sulfuric acid is the only such acid demonstrated by working example.) It is said to be best if the total number of Na atoms per atom of P is not less than 6. Heteropolyacids in the series designated $H_4[PMo_{11}VO_{40}]$ to $H_{11}[PMo_4V_8O_{40}]$ are said to be obtained, and are said to be used in most of the working examples. (We have found that such solutions prepared according to the methods disclosed in Matveev patents are not actually solutions of free heteropolyacids, as designated by formulas of the type $H_n[PMo_pV_qO_{40}]$. Instead, they are solutions of sodium salts of partially or completely neutralized heteropolyacids; that is, solutions of sodium polyoxoanion salts.)

According to Matveev patents, the activity and stability of the catalyst is increased by the presence of certain other mineral or organic acids which do not react (or react only feebly) with palladium and contain no halide ions(e.g. $H_2SO_4$, $HNO_3$, $H_3PO_4$, or $CH_3COOH$). The most preferable of the above acids is sulfuric acid, which is said to increase the activity and stability of the catalyst whilst not seriously increasing the corrosivity of the solution. Sulfuric acid is the only acid which appears in the working examples. Matveev patents prescribe that the amount of acid is enough to maintain the "pH" of the solution at "not more than 3, preferably at 1.0". The working examples predominantly recite "pH" 1. Matveev patents indicate that with "higher pH values", the catalyst is not sufficiently stable with respect to hydrolysis and palladium precipitation, and is of low activity in the olefinic reaction. They further indicate that with "lower pH values", the rate of the oxygen reaction is appreciably diminished. However, Matveev patents do not disclose any method for determining the "pH" of the disclosed solutions, nor do they specify anywhere how much sulfuric acid was added to achieve the stated "pH" value.

The disclosure of Matveev patents is generally directed towards providing a catalyst system having a reversibly acting oxidant (wherein the reduced form of the oxidant can be reacted with dioxygen to regenerate the oxidant) and having an absence of chloride ions. Mineral acids which contain halide ions are specifically excluded from the certain other acids added in the disclosed system. $PdCl_2$ is among the palladium compounds used in the working examples; it is the only source of added chloride disclosed and is added only coincidental to the selection of $PdCl_2$ as the palladium source. $PdCl_2$ and $PdSO_4$ are generally disclosed to be equivalent palladium sources.

Matveev patents' preferred palladium concentration in the catalyst is said to be 0.002 g-atom/liter (2 millimolar). This is the concentration demonstrated in most of the working examples. In Example 9 of both Belgian and British patents, a catalyst containing a very high concentration of heteropolyacid, 1.0 g-mole/liter, and a very high concentration of $PdCl_2$, 0.5 g-atom/liter, is disclosed. This would mean that 1.0 g-atom/liter chloride is added as part of the palladium source. The stated conclusion from this example is that the high viscosity and specific gravity of such concentrated solutions adversely affect the mass transfer conditions and make the process diffusion controlled and impractical. The result reported for this test with 0.5 g-atom/liter $PdCl_2$ is so poor, especially in terms of palladium activity (see Table 1), as to lead one away from attempting to use the example.

The results of selected working examples reported in Matveev patents are presented in Table 1. The examples selected are those said to use a phosphomolybdovanadic heteropolyacid in the oxidation of ethylene for which quantitative results are reported. Data and results to the left of the vertical bar in Table 1 are taken directly from the patent. Results to the right of the vertical bar are calculated from the reported results. The Example numbers are those used in Belgian 828,603.

Most working examples in Matveev patents report tests conducted in a shaking glass reactor. Typical reaction conditions in this reactor were 90° C. with 4.4 psi of ethylene, and separately with 4.4 psi of oxygen. Among the examples collected in Table 1, those using the shaking glass reactor with the preferred concentrations of heteropolyacid and palladium (Examples 1–6) gave ethylene and oxygen rates of 0.089–0.156 and 0.037–0.086 (millimoles/liter)/second, respectively (see Table 1). Example 9, with 0.5 g-atom/liter $PdCl_2$, is said to be diffusion controlled; ethylene and oxygen reaction rates were 0.223 and 0.156 (millimoles/liter)/second, respectively.

We have found that shaking reactors are generally poor devices for mixing such gaseous reactants and liquid aqueous phases and the rate diffusion (mass transfer) of gaseous reactants into an aqueous catalyst solution for reaction is prohibitively slow in such reactors. Additionally, 4.4 psi of ethylene is relatively too low a pressure for rapid dissolution of ethylene into a aqueous catalyst solution.

TABLE 1

Examples from Belgian Patent 828,603

Reported:

| Ex.[1] No. | Rctr[2] | [Pd][3] mM | Pd source | [HPA][4] Molar | HPA Vq[5] | % xs V[6] | temp °C. | $P_{C_2H_4}$ mm Hg | $C_2H_4$ rate W[9] | $C_2H_4$ capacity mole/l | $P_{O_2}$ mm Hg | $O_2$ rate W[10] |
|---|---|---|---|---|---|---|---|---|---|---|---|---|
| 1 | sg | 2 | $PdCl_2$ | 0.3 | 6 | 25 | 90 | 230 | 143 | 0.6 | 230 | 115 |
| 2 | sg | 2 | $PdCl_2$ | 0.3 | 8 | 35 | 90 | 230 | 248 | 0.8 | 230 | |
| 3 | sg | 2 | $PdSO_4$ | 0.3 | 4 | 15 | 90 | 230 | 128 | 0.36 | 230 | 105 |
| 4 | sg | 2 | $PdCl_2$ | 0.3 | 3 | 10 | 90 | 230 | 120 | 0.25 | 230 | 70 |
| 5 | sg | 2 | $PdSO_4$ | 0.3 | 2 | 5 | 90 | 230 | 210 | 0.15 | 230 | 50 |
| 6 | sg | 2 | $PdCl_2$ | 0.2 | 6 | 25 | 90 | 230 | 190 | 0.3 | 230 | 60 |
| 6 | sg | 2 | $PdCl_2$ | 0.2 | 6 | 25 | 110 | 6 atm | 900 | 0.3 | 3.5 atm | 450 |
| 9 | sg | 500 | $PdCl_2$ | 1.0 | 6 | 25 | 90 | 230 | 300 | 3.0 | 230 | 210 |
| 10 | sg | 1 | Pd metal | 0.2 | 6 | 25 | 90 | 230 | 150 | 0.2 | 230 | 100 |
| 12 | sg | 1 | $PdSO_4$ | 0.1 | 5 | ? | 50 | 230 | 25 | 0.15 | 230 | 10 |

Calculated:

| Ex.[1] No. | $P_{C_2H_4}$ psi | $C_2H_4$ rate mM/s[11] | Pd t.f. 1/s[12] | Pd TON[7] | % V red[8] | $P_{O_2}$ psi | $O_2$ rate mM/s[13] |
|---|---|---|---|---|---|---|---|
| 1 | 4.4 | 0.106 | 0.053 | 300 | 53 | 4.4 | 0.086 |
| 2 | 4.4 | 0.185 | 0.093 | 400 | 49 | 4.4 | ? |
| 3 | 4.4 | 0.095 | 0.048 | 180 | 52 | 4.4 | 0.078 |
| 4 | 4.4 | 0.089 | 0.045 | 125 | 51 | 4.4 | 0.052 |
| 5 | 4.4 | 0.156 | 0.078 | 75 | 48 | 4.4 | 0.037 |
| 6 | 4.4 | 0.141 | 0.071 | 150 | 40 | 4.4 | 0.045 |
| 6 | 88.2 | 0.670 | 0.335 | 150 | 40 | 51.4 | 0.335 |
| 9 | 4.4 | 0.223 | 0.0004 | 6 | 80 | 4.4 | 0.156 |
| 10 | 4.4 | 0.112 | 0.112 | 200 | 27 | 4.4 | 0.074 |
| 12 | 4.4 | 0.019 | 0.187 | 150 | 150? | 4.4 | 0.007 |

1. All examples use solutions said adjusted to pH 1 with sulfuric acid, except Ex. 12 in which no sulfuric acid is added and the pH is not reported.
2. Reactor type: sg = shaking glass, ss = stainless steel (method of agitation not reported)
3. Palladium concentration, millimolar (mg-atom/liter)
4. Heteropolyacid concentration, Molar (g-mole/liter)
5. Heteropolyacid said to be used, according to the formula $H_n[PMo_pV_qO_{40}]$, n = 3 + q, p = 12 − q
6. Vanadium used in excess in the preparation of the HPA solution, % of q (see footnote 5)
7. Palladium turnover number per ethylene reaction = ($C_2H_4$ capacity, moles/liter)/(Pd concentration, moles/liter)
8. Fraction of vanadium reduced (utilized to oxidize ethylene) in ethylene reaction = ($C_2H_4$ capacity,mole/l)/[(total V concentration,g-atom/l)/2], where total V concentration = [HPA](q)(1 + fraction excess V used in HPA solution preparation)
9. Average rate of ethylene reaction as [(milliliters $C_2H_4$ at 750 mmHg, 23° C.)/liter solution]/minute.
10. Average rate of oxygen reaction as [(milliliters $O_2$ at 750 mmHg, 23° C.)/liter solution]/minute.
11. Rate of ethylene reaction as [millimoles $C_2H_4$/liter solution/second.

TABLE 1-continued

Examples from Belgian Patent 828,603

12. Palladium turnover frequency, {[millimoles $C_2H_4$/liter solution]/second}/millimolar Pd concentration.
13. Rate of oxygen reaction as [millimoles $O_2$/liter solution]/second.

One test in Example 6 is reported for another reactor, a stainless steel reactor, with 88.2 psi of ethylene and with 51.4 psi of oxygen, each at 110° C. The method of mixing the gas and liquid phases in this reactor is not specified. Example 6 also reports results with the same catalyst system in the shaking glass reactor. The ethylene reaction rates were 0.141 (millimoles/liter)/second in the shaking glass reactor and 0.670 (millimoles/liter)/second in the stainless steel reactor. The oxygen reaction rates were 0.045 (millimoles/liter)/second in the shaking glass reactor and 0.335 (millimoles/liter)/second in the stainless steel reactor. Thus, the reaction rates did not increase proportionally with the pressure when it was increased from about 4 psi to about 90 psi. It is well known that the diffusion rate of a reacting gas into a liquid, as well as the gas molecule concentration in the liquid phase at saturation, is proportional to the partial pressure of the gas in the gas phase, all other factors being constant. Accordingly, the stainless steel reactor used for the higher pressure test of Example 6 appears to be a poorer device for the mixing of gas and liquid phases than the shaking glass reactor used for the other test in the Matveev patents.

Typical apparent palladium turnover frequencies calculated from ethylene reaction rates and palladium concentrations reported in Matveev patents' working examples using a shaking glass reactor are all less than 0.2 (millimoles $C_2H_4$/mg-atom Pd)/second. The higher pressure test at 110° C. in a stainless steel reactor in Example 6 gave the highest apparent palladium turnover frequency of 0.335 (millimoles $C_2H_4$/mg-atom Pd)/second. Although Matveev patents purport that the disclosed catalysts are up to 30 to 100 times more active in olefin oxidation over the Wacker catalyst, the apparent activity of the palladium catalyst in the best example is no higher than the activity of a typical Wacker palladium catalyst in typical process operation at comparable temperatures. This result is obtained even though the disclosed catalyst solution is substantially free of the chloride ion concentration which inhibits the palladium activity in the Wacker catalyst. In contrast, the present invention demonstrably provides palladium catalyst activities substantially exceeding the activity of a Wacker palladium catalyst in typical process operation.

From Matveev patents' ethylene reaction capacities and the palladium concentrations, the number of palladium turnovers per ethylene reaction capacity can be calculated (see Table 1, TON). The highest number of turnovers obtained was 400 with the heteropolyacid containing 8 vanadium atoms (and with 35% excess vanadium present), Example 2.

The ethylene reaction capacities of the catalyst solutions of Matveev's working examples appear generally to follow the vanadium content of the solutions (see Table 1). For the tests with the preferred concentrations of heteropolyacid and palladium and at the preferred "pH" 1 (Examples 1–6), the reported ethylene reaction capacities are calculated to correspond to 40% to 53% of the oxidizing capacity of the vanadium(V) content of the solution, assuming two vanadium(V) centers are reduced to vanadium(IV) for each ethylene oxidized to acetaldehyde.

Example 12 of Matveev's Belgian patent reports a test with no addition of sulfuric acid. (This result was omitted from the UK patent.) The heteropolyacid is designated $H_5[PMo_{10}V_2O_{40}]$ and is used at 0.1 molar concentration with palladium sulfate at 0.1 mg-atom/liter concentration. A "pH" for this solution is not reported. The reaction is conducted at 50 C. On cycling between ethylene and oxygen reactions, the rate of the ethylene reaction is said to diminish constantly due to hydrolysis of the Pd salt. (Typical examples with sulfuric acid added, such as examples 1–6, were reported stable to 10 or more cycles.) This result corresponds to Matveev's disclosure that the stability of the catalyst is increased by sulfuric acid, that the amount of acid is such as to maintain the "pH" at not more than 3, and that with higher "pH" values the catalyst is not sufficiently stable against hydrolysis and palladium precipitation. This result reported with no addition of sulfuric acid is so poor as to lead one away from attempting to use the example.

Matveev patents also report working examples for the oxidation of propylene to acetone, n-butenes to methyl ethyl ketone, and 1-hexene to methyl butyl ketone using the disclosed catalyst system. For reaction of mixtures of n-butenes, 4.4 psi, at 90° C. in the shaking glass reactor (Example 19 in Belgian 828,603; Example 16 in UK 1,508,331), the reported reaction rate is 50 [(ml butenes at 750 mm Hg, 23° C.)/liter]/minute (corresponding to 0.037 (millimoles butenes/liter)/second) an the capacity of the reaction solution is 0.25 moles butenes/liter. The palladium concentration in the example is 2 mg-atom/liter: the palladium turnover frequency is calculated 0.019 (millimoles butenes/mg-atom Pd)/second; the number of Pd turnovers per butene reaction capacity is calculated 125. The fraction of the vanadium(V) concentration of the solution reduced by the butene capacity is calculated 51%.

In contrast to the teachings of the Matveev patents, we have found the following: 1) Although the Matveev patents teach that sulfuric acid increases the activity and stability of the catalyst, we have discovered that substantially increased activity (olefin and oxygen reaction rates) and stability can be obtained by avoiding the presence of sulfuric acid, and of sulfate species generally; 2) Although the Matveev patents teach that the rate of the oxygen reaction is appreciably diminished at "pH" values lower than 1, we have discovered that oxygen reaction rates can be obtained which are orders of magnitude higher than those reported in the patents and which are substantially undiminished in solutions having hydrogen ion concentrations greater than 0.10 mole/liter; 3) Although the Matveev patents teach that the activity and stability of the catalyst are increased on increasing the number of vanadium atoms in the polyacid, for example from 1 to 6, we have discovered that, at least in the practice of the present inventions, the activity (olefin and dioxygen reaction rates) is typically invariable with the vanadium content of the polyacid and the stability may be decreased on increasing the vanadium content of the polyacid towards 6; 4) Although the Matveev patents teach that the total number of Na atoms per atom of P be not less than 6, we have found that with the preferred polyoxoanion-comprising catalyst solutions of the present invention, which optionally contain $Na^+$ countercations, the desired acidity can be obtained while avoiding sulfuric acid by preferably keeping the number of Na atoms per atom of P less than 6.

East German Patent No. 123,085, by some of the inventors of the Matveev patents, discloses a chloride-free catalyst for the liquid phase oxidation of ethylene to acetaldehyde and acetic acid that consists of a solution of a palladium salt with an anion that does not complex palladium or does so only weakly and a heteropolyacid or isopolyacid or salts thereof that have a redox potential greater than 0.35 V. The aqueous solutions disclosed in the Examples contain $2.5 \times 10^{-4}$ mole/liter $PdSO_4$, $5 \times 10^{-2}$ mole/liter heteropolyacid, (specified as $H_5[P(Mo_2O_7)_5V_2O_6]$, $H_8[Si(Mo_2O_7)V_2O_6]$, or $H_8[Ge(Mo_2O_7)V_2O_6]$), $5 \times 10^{-2}$ mole/liter $CuSO_4$ (omitted in Example 3), and $5 \times 10^{-2}$ mole/liter $NaVO_3$, and are said to have a "pH" of 2. Neither the method of preparation of the heteropolyacids in the solutions, nor the means of acidifying the solutions to this stated "pH" is disclosed. In the Examples, these solutions are said to be reacted at 30° C. with ethylene at 720 mm Hg partial pressure or at 60° C. with ethylene at 600 mm Hg partial pressure, and with oxygen at the same pressures, using a glass reactor that can be agitated. The greatest ethylene reaction rate disclosed is 44 ml ethylene reacted by 50 ml solution in 20 minutes at 60° C. with and ethylene partial pressure of 600 mm Hg, corresponding to 0.21 (millimole $C_2H_4$/liter)/second and a palladium turnover frequency of 0.085 (millimole $C_2H_4$/mg-atom Pd)/second. The greatest oxygen reaction rate disclosed is 10 ml oxygen reacted by 50 ml solution in 27 minutes at 30° C. with an oxygen partial pressure of 720 mm Hg, corresponding to 0.005 (millimole $O_2$/liter)/second.

East German Patent No. 123,085, also mentions small additions of chloride or bromide ions act as oxidation accelerators and activate the catalysts, with molar ratios of $[Pd^{++}]:[Cl^-] \leq 1:20$ and $[Pd^{++}]:[Br^-] \leq 1:5$ being favorable. The patent makes no other mention of chloride addition to the disclosed catalyst and chloride is nowhere indicated in any of the working Examples. Instead, the title of the patent, the claims, and the disclosure elsewhere all explicitly specify a chloride-free catalyst.

Additional results from some of the inventions of the Matveev patents are reported in *Kinetika i Kataliz*, vol. 18(1977), pp. 380–386 (English translation edition pp. 320–326, hereafter *"Kinet. Katal.* 18-1"). Reaction kinetic experiments are reported for the ethylene oxidation reaction with phosphomolybdicvanadic heteropolyacids in the presence of Pd(II) sulfate using a shaking reactor with circulation of the gas phase. The absolute values of the observed reaction rates are said to be quite small, and not complicated by mass-transfer processes. Most of the reported experiments are conducted at about 20° C., and this low temperature appears to be the principal reason the observed reaction rates are so small. Typical reaction rates reported are about 1 to $12 \times 10^{-4}$ (moles/liter)/minute, which corresponds to about 0.002 to 0.020 (millimoles/liter)/second; compare to ethylene reaction rates of about 0.1–0.2 (millimoles/liter)/second calculated from the results reported for experiments at 90° C. in Matveev patents (see Table 1). The reaction rates reported in *Kinet. Katal.* 18-1 are so small as to lead one away from attempting to use the reported reaction conditions for any practical production purpose.

Ethylene pressures for the reactions of *Kinet. Katal.* 18-1 are not reported. The ethylene concentrations are instead given, but no method of either setting or determining the ethylene concentration is mentioned, nor is it clear whether these ethylene concentrations are sustained in solution under the reaction conditions.

*Kinet. Katal.* 18-1 states that solutions of phosphomolybdicvanadic heteropolyacids were synthesized by a procedure described in *Zh. Neorg. Khim.*, vol. 18(1973), p. 413 (English translation edition pp. 216–219). This reference describes making solutions from $Na_2HPO_4$, $Na_2MoO_4 \cdot 2H_2O$, and $NaVO_3 \cdot 2H_2O$ at "pH" 2; the method of acidification of the solutions of these basic salts, when stated, is with sulfuric acid. (This reference further mentions the isolation of crystalline vanadomolybdo-phosphoric acids via ether extraction of their ether addition compounds from sulfuric acid-acidified solutions. These methods of preparing solution vanadomolybdophosphoric acids with sulfuric acid and crystalline products by ether extraction are also described in earlier papers cited by this reference; for example, *Inorg. Chem.*, 7 (1968), p. 137.) The reaction solutions of *Kinet. Katal.* 18-1 are said to be prepared from the solutions of phosphomolybdicvanadic heteropolyacids by addition palladium sulfate, dilution, and adjustment of the pH by the addition of $H_2SO_4$ or NaOH. However, this reference does not disclose the composition of the test solutions, in terms of the amounts of $H_2SO_4$ or NaOH added, nor any method for determining the pH of the disclosed solutions.

*Kinet. Katal.* 18-1 reports the dependence of the ethylene reaction rate on the solution pH over the stated range 0.8 to 2.2, under the disclosed conditions with the heteropolyacid designated $H_6[PMo_9V_3O_{40}]$ at 0.05 mole/liter, palladium at $3 \times 10^{-3}$ g-atom/liter, ethylene at $1 \times 10^{-4}$ mole/liter, and 21° C. As the pH is increased towards 2, the rate of the ethylene reaction is shown to decrease. From evaluation of graphic figures in the reference, the maximum rate of ethylene reaction was achieved over a pH range of 0.8 to 1.6, and corresponded to 0.023 (millimole $C_2H_4$/liter)/second and a palladium turover frequency of 078 (mole $C_2H_4$/mole palladium)/second.

Matveev reviews his studies on the oxidation of ethylene to acetaldehyde in *Kinetika i Kataliz*, vol. 18 (1977), pp. 862–877 (English translation edition pp. 716–727; *"Kinet. Katal.* 18-2"). The author states (English translation edition p. 722): "The chloride-free catalyst was an aqueous solution of one of the HPA-n, acidified with $H_2SO_4$ to pH 1, in which a nonhalide palladium salt (sulfate, acetate, etc.) was dissolved." (HPA-n are defined as phosphomolybdenumvanadium heteropolyacids.) Reference is then made to the studies reported in *Kinet. Katal.* 18-1.

*Reaction Kinetics and Catalysis Letters*, vol 16 (1981), pp. 383–386 reports oxidation of 1-octene to 2-octanone using a catalytic system of $PdSO_4$ and heteropolyacid designated $H_9PMo_6V_6O_{40}$ in a shaking glass reactor with 1 atm. oxygen. The heteropolyacid is said to be synthesized as in UK 1,508,331, and used as an acidic sodium salt $Na_7H_2PMo_6V_6O_{40}$. The catalyst solution is said to have a pH equal to 0.5–1.0, which was attained by the addition of $H_2SO_4$. However, no results are identified with a specific pH value. Palladium is used in concentrations of ~4–6 millimolar and $PdSO_4$ is said to give a more active catalyst than $PdCl_2$. The catalyst is said to have limited stability above 80° C., apparently due to precipitation of palladium.

Ropa Uhlie 28, pp. 297–302 (1986) (Chem Abstr. 107(1):6740r) reports oxidation of 1-octene to 2-octanone using a solution of 0.075 M heteropolyacid designated $H_{3+n}PMo_{12-n}V_nO_{40}$, n=6 or 8, and containing $PdSO_4$. The heteropolyacid solution was prepared from $NaH_2PO_4$, $MoO_3$, and $V_2O_5$ in water by addition of NaOH, then $H_2SO_4$, with adjustment of the stated "pH" to 1.

*J. Organomet. Chem.* 327 (1987) pp. C9–C14 reports oxidation of 1-octene to 2-octanone by oxygen using an aqueous solution of 0.12 mole/liter heteropolyacid designated $HNa_6PMo_8V_4O_{40}$, with 0.01 mole/liter $PdSO_4$, with various co-solvents, at 20° C., in one-stage mode. The heteropolyacid is said to be prepared by the method described in UK 1,508,331; the "pH" of the catalyst solution is not specifically disclosed. For the reaction, 1-octene and oxygen are contacted simultaneously with the catalyst solution. The heteropolyacid cocatalyst is said to be regenerated by treating the aqueous solution with 1 atm. $O_2$ at 75° C.

*Reaction Kinetics and Catalysis Letters*, vol 3 (1975), pp. 305–310 reports the oxidation of vanadium(IV) in aqueous solutions of vanadyl sulfate ($V^{IV}OSO_4$), 0.05–0.25 mole/liter, in the "pH" region 2.5–4.5, in the presence of small amounts of sodium molybdate in a shaker reactor, at 30° C. with 730 mmHg oxygen pressure. At "pH" values below 3.0 the reaction rate is reported to decrease sharply. A heteropolyacid complex of molybdenum and vanadium was isolated from a reaction solution.

*Koordinatsionnaya Khimiya*, vol. 3 (1977), pp. 51–58 (English translation edition pp. 39–44) reports the oxidation of reduced phosphomolybdovanadium heteropolyacids containing vanadium(IV), in aqueous solution at "pH"'s<1, at 60° C. by oxygen. Heteropolyacids designated $H_{3+n}[PMo_{12-n}V_nO_{40}]$, n=1–3, were said to be synthesized by the method of *Zh. Neorg. Khim.*, vol. 18 (1973), p. 413 (see above), and a solution of the sodium salt of the heteropolyacid designated n=6 was said to be prepared by dissolving stoichiometric amounts of sodium phosphate, molybdate, and vanadate in water, boiling the solution, and acidifying it to "pH" 1. Different "pH" values for the solutions of the reduced forms of these heteropolyacids were said to be obtained by altering the initial "pH" values of the heteropolyacid solutions, monitored by a pH meter. The acid used for acidification and for altering the initial "pH" values are not disclosed. Oxygen reaction rates for the reduced forms of the heteropolyacids designated n=2,3, and 6 show maxima at about "pH" 3 (at about $34 \times 10^{-3}$ (mole/liter)/minute; or, 0.57 (millimole/liter)/second), and decline precipitously as the "pH" is lowered; it becomes almost negligible for n=2 at "pH" 1.

*Koordinatsionnaya Khimiya*, vol. 5 (1979), pp. 78–85 (English translation edition pp. 60–66) reports the oxidation of vanadium(IV) in aqueous solutions of vanadyl sulfate, 0.1–0.4 mole/liter, in the "pH" region 2.5–4.5, in the presence of smaller amounts of molybdovanadophosphoric heteropolyacid designated $H_9PMo_6V_6O_{40}$, in an agitated reactor, at 0°–30° C., by oxygen. A weak dependence of the rate on "pH" is reported, with the rate decreasing with decreasing "pH" below about "pH" 3.5. The addition of $Na_2SO_4$ is said to have no influence on the rate of the reaction.

*Izvestiya Akademii Nauk SSSR, Seriya Khimicheskaya*, 1981, pp. 2428–2435 (English translation edition pp. 2001–2007) reports studies of the oxidation of reduced forms ("blues") of molybdovanadophosphate heteropolyacids designated $H_{3+n}[PMo_{12-n}V_nO_{40}]$, n=1–4,6, containing vanadium(IV), in aqueous solution at "pH" 3.0, in a glass flask with magnetically-coupled stirring of the liquid phase, at 25° C. with 2–10 kPa (0.3–1.5 psi) oxygen. Reaction rates are extremely slow under these low temperature, low pressure conditions in this reaction mixing vessel. (From the data, reaction rates in the region <0.0001 (millimoles/liter)/second are calculated.) The oxygen reaction rates of a reduced form of the molybdovanadophosphate n=3 were measured at "pH"'s 2.0,3.0, and 4.0. A maximum was observed at "pH" 3.0. Aqueous solutions of Na salts of the heteropolyacids and the corresponding blues for the experiments were said to be obtained as in *Izvestiya Akademii Nauk SSSR, Seriya Khimicheskaya*, 1980, pp. 1469. This reference discloses that aqueous solutions of heteropolyanions were obtained by reacting stoichiometric amounts of $H_3PO_4$, $MoO_3$, and $NaVO_3 \cdot 2H_2O$ with heating in the presence of $Na_2CO_3$. (Neither the amount of $Na_2CO_3$ added, the concentration of heteropolyanion, the resulting "pH"'s, nor the complete compositions of the solutions are disclosed.) This reference further discloses the addition of vanadium(IV) in the form of $VOSO_4 \cdot 2H_2O$ to produce the heteropoly blues. The experimental solutions in this reference are said to comprise heteropolyanion and vanadyl at "pH" 1.60–2.98, buffer solution of $NaHSO_4$ and $Na_2SO_4$; neither the concentration of the buffering sulfate ions nor an accounting of their origin is disclosed.

*Reaction Kinetics and Catalysis Letters*, vol 17 (1981), pp. 401–406 reports the oxidation of vanadium(IV) in aqueous solutions of vanadyl sulfate, 0.02–0.4 mole/liter, in the "pH" region 2.5–4.5, in the presence of smaller amounts of molybdovanadophosphoric heteropolyacid designated $H_6PMo_9V_3O_{40}$, by the methods of *Koordinatsionnaya Khimiya*, vol. 5 (1979), pp. 78–85. At "pH" values below 3.0 the reaction rate is reported to decrease sharply.

*J. Chem. Soc. Dalton Trans.*, 1984, pp. 1223–1228 reports studies of the palladium sulfate-catalyzed oxidation of 1-butene to 2-butanone (methyl ethyl ketone) with phosphomolybdovanadic acids both in the absence and in the presence of oxygen. These studies are reported in greater detail in Palladium and Heteropolyacid Catalyzed Oxidation of Butene to Butanone, S.F. Davison, Ph.D. Thesis, University of Sheffield, 1981. These references report, as do others loc. cit., that phosphomolybdovanadic acids are extremely complex mixtures of anions of the type $[PMo_{12-x}V_xO_{40}]^{(3+x)-}$. Crystalline phosphomolybdovanadic acids, designated $H_{3+n}[PMo_{12-n}V_nO_{40}]$, n=1–3, prepared by the ether extraction method of *Inorg. Chem.*, 7 (1968), p. 137 were observed to be mixtures which disproportionated still further in the acidic media used for catalysis. Accordingly, solutions prepared by the method of UK 1,508,331 were chosen as appropriate for the catalytic reactions (see Davison Thesis, pp. 63 and 77), except that stoichiometric amounts of $V_2O_5$ (not excess) were used. The solutions were prepared from $V_2O_5$, $MoO_3$, $Na_3PO_4 \cdot 12H_2O$, and $Na_2CO_3$, at 0.2 M P, and acidified to "pH" 1 by addition of concentrated sulfuric acid The reactions of *J. Chem. Soc. Dalton Trans,.* 1984, pp. 1223–1228 and Davison Thesis in the absence of oxygen were conducted at 20° C. and 1 atm 1-butene in a mechanically shaken round-bottomed flask. Reactions using 5 mM $PdSO_4$ and 0.05 M vanadium(V) in aqueous sulfuric acid (0.03–0.2 mole/liter, depending on n) are reported to give similar initial reaction rates for n=1–7. The reactions required ca. 30 minutes for completion and gave 5 turnovers on Pd (stoichiometric for two vanadium(V) reduced to vanadium(IV) per 1-butene oxidized to 2-butanone.). A stated intention of the work was to minimize chloride content; $PdCl_2$ is said to have similar reactivity to $PdSO_4$.

The reactions of *J. Chem. Soc. Dalton Trans.*, 1984, pp. 1223–1228 and Davison Thesis in the presence of oxygen were conducted at 20° C. and 1 atm of 1:1 1-butene:oxygen in a round-bottomed flask with magnetically coupled stirring. Results are reported for the solutions used in reactions in the absence of oxygen; up to about 40 turnovers on Pd were obtained in about 120 minutes with the heteropolyacid designated $PMo_6V_6$ ($H_9[PMo_6V_6O_{40}]$ in the journal account). An experiment is also reported using this heteropolyacid in 0.87 M sulfuric acid (in the journal account it is cited as 1 M sulfuric acid and the "pH" is stated to be ca.-0.3.). The extra acid is said to be slightly detrimental: up to about 32 turnovers on Pd were obtained in about 120 minutes. The various P-Mo-V co-catalysts are said to be longer lasting in the "pH" range 1–2.

U.S. Pat. Nos. 4,434,082; 4,448,892; 4,507,506; 4,507,507; 4,532,362; and 4,550,212, assigned to Phillips Petroleum Company, disclose systems for oxidizing olefins to carbonyl compounds comprising a palladium component, a heteropolyacid component, and additional components. U.S. Pat. No. 4,434,082 and 4,507,507 both add a surfactant and a diluent of two liquid phases, one of which is an aqueous phase, and one of which is an organic phase, U.S. Pat. No. 4,448,892 and 4,532,362 also both add a surfactant and a fluorocarbon. U.S. Pat. No. 4,507,506 adds cyclic sulfones (e.g. sulfolane). U.S. Pat. No. 4,550,212 adds boric acid and optionally a surfactant. The disclosure of heteropolyacids in each of these patents is the same as in Matveev patents, and the heteropolyacids demonstrated by working examples are prepared by the same method as in Matveev patents, including acidification to "pH" 1.00 with sulfuric acid. $PdCl_2$ is among the palladium components exemplified. Among the disclosed surfactants are quaternary ammonium salts and alkyl pyridinium salts, including chloride salts. However, cetyltrimethylammonium bromide is the only surfactant demonstrated by working example.

The working examples for olefin oxidation among the above patents predominantly demonstrate the one-stage oxidation of individual n-butenes to 2-butanone in the presence of oxygen. U.S. Pat. No. 4,434,082 and 4,507,507 demonstrate oxidation of 3,3-dimethyl-1-butene. U.S. Pat. No. 4,448,892 and 4,532,362 demonstrate the oxidation of 1-dodecene. U.S. Pat. No. 4,507,506 is concerned with the one-stage oxidation of long-chain alpha-olefins and demonstrates oxidations of 1-decene and 1-dodecene.

U.S. Pat. Nos. 4,720,474 and 4,723,041, assigned to Catalytica Associates, disclose systems for oxidizing olefins to carbonyl products comprising a palladium component, a polyoxoanion component, and additionally a redox active metal component (certain copper, iron, and manganese salts are disclosed) and/or a nitrile ligand. The disclosures emphasize the elimination of chloride from the system; the catalyst systems do not contain chloride ions except sometimes as "only trace amounts" resulting from the presence of chloride in the synthesis of the polyoxoanion "in order to form and (or) crystallize the desired structure". The patents disclose that "pH" or acidity can be adjusted by various proton sources, such as an acid form of a polyoxoanion or certain inorganic acids; sulfuric acid is said to be a preferred acid and is the only acid so described. The "pH" of the liquid phase is said to be preferably maintained between 1 and 3 by the addition of appropriate amounts of $H_2SO_4$. The working examples for olefin oxidation all add $H_2SO_4$ to the reaction solution, either to obtain 0.1 N concentration or to obtain "pH" 1.5 or 1.6.

U.S. Pat. No. 4,720,474 and 4,723,041 demonstrate by working example the oxidation of various olefins to carbonyl products: predominantly 1-hexene, as well as ethylene, 1- and 2-butenes, 4-methyl-1-pentene, cyclohexene, 1-octene, and 2-octene, all in the presence of oxygen. Example XL gives initial olefin reaction rates using a catalyst solution including $Pd(NO_3)_2$, $K_5H_4PMo_6V_6O_{40}$, and $Cu(NO_3)_2$, with $H_2SO_4$ added to "pH" 1.5, at 85° C. and 100 psig total pressure with oxygen in a stirred reactor without baffles. The reported ethylene reaction rate is $8.58 \times 10^{-7}$ moles $C_2H_4$/sec ml (0.858 (millimoles/liter)/second). This corresponds to a palladium turnover frequency of 0.17 (millimoles $C_2H_4$/millimole Pd)/second. A slightly lower rate is reported for 1-butene.

OBJECTS OF THE INVENTION

The present invention is directed towards one or more of the following objects. It is not intended that every embodiment will provide all these recited objects. Other objects and advantages will become apparent from a careful reading of this specification.

An object of this invention is to provide an effective and efficient process for oxidation of an olefin to a carbonyl compound. Another object of this invention is to provide a catalyst solution for oxidation of an olefin to a carbonyl compound. Another object of this invention is to provide an effective and efficient process for the preparation of catalyst solutions for oxidation of an olefin to a carbonyl compound.

A further object of this invention is to provide an effective and efficient process for oxidation of an olefin to a carbonyl compound by one or more polyoxoanion oxidants in aqueous solution, catalyzed by palladium. Another object of this invention is to provide an effective and efficient process for reoxidation of one or more reduced polyoxoanions in aqueous solution by reaction with dioxygen. Another object of this invention is to provide an effective and efficient process for oxidation of an olefin to carbonyl compound by dioxygen catalyzed by palladium and one or more polyoxoanion in aqueous solution.

A further object of this invention is to provide an economically practicable catalyst solution and process for oxidation of ethylene to acetaldehyde in an industrial acetaldehyde plant designed to operate the Wacker process chemistry. Another object of this invention is to provide an economically practicable process for oxidation of an olefin, other than ethylene, to a ketone in an industrial plant originally designed to operate the Wacker process chemistry for the production of acetaldehyde.

A further object of this invention is to provide an economically practicable catalyst solution and process for oxidation of an olefin directly to a carbonyl compound, which could not be so accomplished previously due to co-production of chlorinated by-products, due to reaction rates which were too slow, or due to another reason.

A further object of this invention is to achieve any of the above objectives with a less corrosive catalyst solution than the Wacker catalyst solution. Another object of this invention is to achieve any of above objectives while minimizing or avoiding the co-production of hygienically or environmentally objectionable chlorinated organic by-products. Another object of this invention is to achieve any of the above objectives in the essential absence of copper chlorides.

A further object of this invention is to achieve any of the above objectives with a higher volumetric productivity (molar amount of olefin oxidized to carbonyl product per unit volume catalyst solution per unit time) than previously disclosed catalyst systems and processes. A further object of this invention is to achieve any of the above objectives with a smaller concentration or amount of palladium catalyst than previously disclosed catalyst systems and processes. Another object of this invention is to achieve any of the above objectives with greater turnovers on palladium (lesser Pd cost per mole carbonyl product) than previously disclosed catalyst systems and processes. Another object of this invention is to achieve any of the above objectives with greater catalyst stability to long term operation than previously disclosed catalyst systems and processes which avoid the use of copper chlorides. Another object of this invention is to achieve any of the above objectives while avoiding the inverse squared rate inhibition by chloride ion concentration and the inverse rate inhibition by hydrogen ion concentration which are typical of the Wacker chemistry.

A further object of this invention is to achieve any of the above objectives with a greater effective utilization of the oxidation capacity of a vanadium (V)containing polyoxoanion oxidant solution, or greater olefin reaction capacity per unit volume, than previously disclosed catalyst systems and processes. Another object of this invention is to achieve any of the above objectives with a greater volumetric reaction rate for the oxidation of vanadium (IV) to vanadium (V) by dioxygen (molar amount of dioxygen reacted per unit volume catalyst solution per unit time) than previously disclosed vanadium-containing catalyst systems and processes. A further object of this invention is to provide an effective and efficient process for oxidation of palladium(0), particularly palladium metal, to dissolved palladium (II) catalyst, in order to provide and sustain palladium catalyst activity in the inventive catalyst system.

Still another object of this invention is to provide a method of preparing an aqueous catalyst solution suitable for accomplishing any of the above objectives.

SUMMARY OF INVENTION

The present invention provides aqueous catalyst solutions useful for oxidation of olefins to carbonyl products, comprising a palladium catalyst and a polyoxoacid or polyoxoanion oxidant comprising vanadium. It also provides processes for oxidation of olefins to carbonyl products, comprising contacting olefin with aqueous catalyst solutions of the present invention. It also provides processes for oxidation of olefins to carbonyl products by dioxygen, comprising contacting olefin with the aqueous catalyst solutions of the present invention, and further comprising contacting dioxygen with the aqueous catalyst solutions.

In certain aqueous catalyst solutions and related processes of the present invention, the solution has a hydrogen ion concentration greater than 0.10 mole per liter when essentially all of the oxidant is in its oxidized state.

In other aqueous catalyst solutions and related processes of the present invention, the solution is essentially free of mineral acids and acid anions other than of the polyoxoacid oxidant and hydrohalic acids. In other aqueous catalyst solutions and related processes of the present invention, the solution is essentially free of sulfuric acid and sulfate ions.

In other aqueous catalyst solutions and related processes of the present invention, the solution further comprises dissolved olefin at a concentration effective for oxidizing the olefin at a rate which is independent of the dissolved olefin concentration. In other aqueous catalyst solutions and related processes of the present invention, the aqueous catalyst solution further comprises the olefin dissolved at a concentration effective for maintaining the activity and stability of the palladium catalyst for continued process operation.

In other aqueous catalyst solutions and related processes of the present invention, the solution further comprises dissolved olefin at a concentration effective for oxidizing the olefin at a rate of at least 1 (millimole olefin/liter solution)/second. In other processes of the present invention, the process comprises contacting the olefin with an aqueous catalyst solution, comprising a palladium catalyst and a polyoxoacid or polyoxoanion oxidant, in mixing conditions sufficient for the olefin oxidation rate to be governed by the chemical kinetics of the catalytic reaction and not be limited by the rate of olefin dissolution (mass transfer) into the solution. In other aqueous catalyst solutions and related processes of the present invention, the aqueous catalyst solution further comprises the olefin dissolved at a concentration effective for the olefin oxidation rate to be proportional to the concentration of the palladium catalyst. In other aqueous catalyst solutions and related processes of the present invention, the aqueous catalyst solution further comprises the olefin dissolved at a concentration effective for providing a palladium turnover frequency of at least 1 (mole olefin/mole palladium)/second. In other aqueous catalyst solutions and related processes of the present invention, the solution further comprises dissolved olefin at a concentration effective for oxidizing the olefin at a rate which is independent of the dissolved olefin concentration. In other aqueous catalyst solutions and related processes of the present invention, the aqueous catalyst solution further comprises the olefin dissolved at a concentration effective for maintaining the activity and stability of the palladium catalyst for continued process operation.

In other aqueous catalyst solutions and related processes of the present invention, the solution further comprises chloride ions. In other aqueous catalyst solutions and related processes of the present invention, the solution further comprises chloride ions at a concentration effective for maintaining the activity and stability of the palladium catalyst for continued process operation. In other aqueous catalyst solutions and related processes of the present invention, the solution further comprises chloride ions at a concentration greater than twice the concentration of palladium. In other aqueous catalyst solutions and related processes of the present invention, the solution further comprises chloride ions at a concentration of at least 5 millimole per liter.

Preferred aqueous catalyst solutions and related olefin oxidation processes of the present invention combine the recited features of two or more of the above mentioned catalyst solutions and related processes. Especially preferred are aqueous catalyst solutions and related processes which combine most or all of the above features.

The present invention also provides processes for the oxidation of vanadium (IV) to vanadium (V) comprising contacting dioxygen with an aqueous solution comprising vanadium and a polyoxoanion. In certain such processes of the present invention the solution has a hydrogen ion concentration greater than 0.10 mole per liter when essentially all of the oxidant is in its oxidized state. In other such processes of the present invention the solution is essentially free of sulfate ions. In other such processes of the present invention the dioxygen is mixed with the aqueous solution under mixing conditions effective to provide a dioxygen reaction rate of at least 1 (millimole dioxygen/liter solution)/second.

The present invention also provides processes for the oxidation of palladium (0) to palladium (II) comprising contacting the palladium (0) with an aqueous solution comprising a polyoxoacid or polyoxoanion oxidant comprising vanadium and chloride ions. In certain such processes of the present invention the palladium (0) comprises palladium metal or colloids.

The present invention also provides processes for the preparation of acidic aqueous solutions of salts of polyoxoanions comprising vanadium, by dissolving oxides, oxoacids, and/or oxoanion salts of the component elements (for example: phosphorus, molybdenum, and vanadium), and optionally carbonate, bicarbonate, hydroxide and/or oxide salts, in water, such that the resulting ratio of hydrogen ions and salt countercations balancing the negative charge of the resulting polyoxoanions in the solution provides a hydrogen ion concentration greater than $10^{-5}$ moles/liter.

We anticipate that the solutions and processes of the present invention will prove useful in oxidation processes other than the oxidation of olefins to carbonyl compounds, including, for example, oxidation of carbon monoxide, oxidation of aromatic compounds, oxidative coupling reactions, oxidative carbonylation reactions, oxidation of halides to halogen, and the like.

DETAILED DESCRIPTION OF THE INVENTION

Empirical and Theoretical Bases for the Invention:

We have found after extensive investigations that certain catalyst solutions and processes discussed in the background references are wholly impractical or practically unworkable for economically practicable commercial manufacture of carbonyl products by the oxidation of olefins. Characteristic problems we found for background catalyst solutions and processes using palladium and polyoxoanions include insufficient olefin oxidation reaction rates, insufficient palladium catalyst activity, insufficient catalyst stability for continued process operation, and insufficient dioxygen reaction rates. The following discussion outlines the results of our investigations towards solving these problems and our understanding of why our solutions to these problems are successful. We do not intend to be bound by the following theoretical explanations since they are offered only as our best beliefs in furthering this art.

In the oxidation of olefins to carbonyl compounds by palladium catalysts and polyoxoanion oxidants comprising vanadium, palladium appears to catalyze the oxidation of olefins by vanadium (V) in the polyoxoanion oxidant (illustrated in reaction (12) for ethylene oxidation to acetaldehyde), where $[V^V]$ and $[V^{IV}]$ represent a single vanadium (V) atom and single vanadium (IV) atom in an aqueous solution of polyoxoanion oxidant, respectively:

$$C_2H_4 + 2[V^V] + H_2O \xrightarrow{Pd^{II}} CH_3CHO + 2[V^{IV}] + 2H^+ \qquad (12)$$

In a subsequent step, conducted either simultaneously (one-stage process) or sequentially (two-stage process) to the above, vanadium (IV) in the polyoxoanion solution can be oxidized by dioxygen to regenerate vanadium (V) for the oxidation of additional olefin:

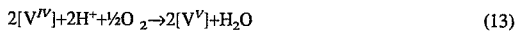

$$2[V^{IV}]+2H^++\tfrac{1}{2}O_2 \rightarrow 2[V^V]+H_2O \qquad (13)$$

(Reactions (12) and (13) combined give the overall reaction (1) for oxidation of ethylene to acetaldehyde by dioxygen.)

Palladium appears to catalyze the oxidation of olefins by vanadium (V) in the polyoxoanion oxidant (reaction (12)) by oxidizing the olefin (reaction (14), illustrated for ethylene), and then reducing vanadium (V) (reaction (15)):

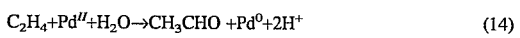

$$C_2H_4+Pd^{II}+H_2O \rightarrow CH_3CHO + Pd^0+2H^+ \qquad (14)$$

$$Pd^0+2[V^V] \rightarrow Pd^{II}+2[V^{IV}] \qquad (15)$$

Functionally, the vanadium in the polyoxoanion solution mediates the indirect oxidation of the reduced $Pd^0$ by dioxygen (reaction (15) plus reaction (13)), and functions in a manner similar to copper chloride in the Wacker process.

We have determined that, in preferred processes of the present invention, under mixing conditions sufficient for the olefin oxidation rate to be governed by chemical kinetics (not limited by the kinetics of olefin dissolution into the solution), the volumetric rate of olefin oxidation by aqueous polyoxoanion comprising vanadium (V) (reaction (12)) is first-order dependent on (proportional to) the concentration of palladium (II), and is substantially independent of the concentration vanadium (V). Accordingly, the oxidation of the $Pd^0$ product of reaction (14) by vanadium (V) (reaction (15)) is rapid relative to the rate of olefin oxidation by palladium (II) (reaction (14)).

We discovered that the catalyst systems of the background references discussed above become deactivated with agglomeration of $Pd^0$ to colloidal palladium or even to precipitated solid palladium metal. Such agglomeration and precipitation competes with the oxidation of $Pd^0$ by vanadium (V) to regenerate the olefin-active $Pd^{II}$ form (reaction (15)). Accordingly, what would have been an originally active palladium inventory would progressively accumulate into an inactive form. For olefin oxidation in the absence of dioxygen (as in equation (12)), essentially complete palladium catalyst deactivation would often occur in these referenced processes before effective utilization of the oxidizing capacity of the vanadium (V) content of the solution. Even when most of the palladium would remain active through the olefin reaction in two-stage operation with subsequent dioxygen reaction, multiple olefin/oxygen reaction cycles resulted in a cumulative loss of the active palladium catalyst concentration.

The aqueous catalyst solutions of this invention have increased stability towards deactivation because of palladium colloid or solid metal formation. Apparently, our processes more rapidly oxidize $Pd^0$ with vanadium (V) (reaction (15)) in competition with agglomeration of $Pd^0$ into colloids or solid palladium metal, and/or they aggressively oxidize already agglomerated palladium (0) forms with vanadium (V), with the result that the concentration of olefin-active $Pd^{II}$ is maintained. Among features of the inventive solutions and related processes which contribute to the increased stability are the following: 1) hydrogen ion concentrations greater than 0.10 mole/liter, 2) presence of chloride ions, especially when above a concentration coincidental to using $PdCl_2$ as the palladium source, 3) concentrations of dissolved olefin effective for rapid reaction rates and sustained palladium catalyst activity, and 4) essential absence of sulfate ions.

The favorable influences of hydrogen ion and chloride ion concentrations on catalyst stability are thought to be related, in part, to decreasing palladium O/II oxidation potentials, favoring oxidation of all forms of reduced palladium to active $Pd^{II}$. We have also discovered that chloride ion catalyzes the corrosive oxidation of even solid palladium metal to soluble $Pd^{II}$ catalyst by polyoxoanions comprising vanadium(V). Accordingly, chloride ions can function to disfavor net accumulation of inactive colloidal and solid metallic palladium by catalyzing rapid regeneration of all forms of palladium(O) to active $Pd^{II}$ catalyst.

A theoretical explanation for the favorable influence of dissolved olefin concentration on palladium catalyst stability is that dissolved olefin is able to bind to the $Pd^0$ product of olefin oxidation, stabilizing it in solution and thereby slowing its rate of agglomeration into colloidal or metallic forms. The oft-used sulfate salts may decrease ("salt-out") olefin solubility in the aqueous solution, thereby decreasing its ability to stabilize the palladium catalyst.

In any event, we have found that, when the concentration of chloride ions in the solution is insufficient to otherwise maintain palladium activity, when ethylene concentration in solution is reduced (due to low ethylene pressure in the gas phase and/or due to insufficient mixing of the gas and liquid phases such that the ethylene oxidation rate becomes limited by the rate of ethylene dissolution into the solution), initial palladium activity declines precipitously. We have determined that such conditions are typical of the examples disclosed in Matveev patents, and contribute to their low apparent palladium catalyst activities relative to the present invention; a significant fraction of the loaded palladium appears to reside in inactive forms.

Effective concentrations of dissolved olefin for sustaining the palladium activity may be achieved when the olefin is contacted with the aqueous catalyst solution in mixing conditions sufficient for the olefin oxidation rate to be governed by the chemical kinetics of catalysis (not limited by the rate of ethylene diffusion into the solution), and are further enhanced by raising the concentration of olefin in the olefinic phase (as in raising the partial pressure of gaseous olefins). Mixing conditions sufficient for the olefin oxidation rate to be governed by the chemical kinetics of the catalytic reaction are established when the reaction rate is governed by chemical characteristics of the catalyst solution, such as its palladium(II) catalyst concentration, and independent of moderate variations in the phase mixing efficiency. When mixing conditions are insufficient, the dissolved olefin concentration in the bulk catalyst solution is depleted by reaction, and the olefin oxidation rate becomes determined by the rate of dissolution (mass transfer) of the olefin into the catalyst solution. When mixing conditions are sufficient, the dissolved olefin concentration approaches the phase partitioning limit (the solubility of the olefin in the solution) and this limit is increased in proportion to the olefin concentration in the olefinic phase. For each combination of olefin, olefin concentration in the olefinic phase, precise catalyst solution composition, and reaction temperature, sufficient mixing requirements in a given reactor device can be established by observing reaction rates governed by chemical kinetic parameters. For ethylene, with preferred aqueous catalysts of the present invention, the ethylene oxidation reactor of a Wacker plant, operated at its typical pressure and temperature provides sufficient concentrations of dissolved ethylene.

In comparison to the inventive catalyst solutions and processes, the catalyst systems and processes of background references using catalysts comprising palladium and polyoxoanion components have generally poor palladium catalyst activity. The background references typically utilize much higher high palladium catalyst loadings to compensate for low palladium activity, and even then do not report acceptable volumetric olefin oxidation rates. A higher palladium concentration results in a lesser number of palladium turnovers (moles olefin reacted/mole palladium present) to react an amount of olefin. Accordingly, the palladium in the systems of the background references is used relatively inefficiently; that is, more palladium is used for the production of a given amount of carbonyl product. Since palladium is a very costly catalyst solution component, this places an economic burden on commercial utilization of the background reference processes.

A convenient measure of palladium catalyst activity is the palladium turnover frequency, (moles olefin reacted/mole palladium)/unit time. Palladium turnover frequencies for ethylene oxidation determined from data presented in the background references, are substantially less than 1 (mole ethylene/mole Pd)/second, often less than 0.1 (mole ethylene/mole Pd)/second. Aqueous catalyst solutions and processes of the present invention can provide palladium turnover frequencies greater than 1 (mole ethylene/mole Pd)/second, generally greater than 10 (mole ethylene/mole Pd)/second. Palladium turnover frequencies greater than 100 (mole ethylene/mole Pd)/second have even been achieved with the present invention.

Similarly improved palladium catalyst activities are also obtained for olefins other than ethylene. Each olefin will have its own intrinsic rate of reaction with the $Pd^{II}$ in a given aqueous catalyst solution, and these rates are influenced by the conditions of the olefin oxidation process using the solution. However, the relative reaction rates of different olefins with various palladium catalyst solutions under various reaction conditions generally follow the same qualitative order.

The poor palladium catalyst activity of the catalyst systems of the background references can be attributed in part to the extent of deactivation of the active palladium catalyst into inactive forms; a fraction of the palladium load resides in colloidal or solid metallic forms with little or no activity. To that extent, the features of the catalyst solutions and related processes of the present invention which contribute to improved palladium catalyst stability, as recited above, also contribute to better apparent palladium catalyst activity.

Aqueous catalyst solutions and related processes of the present invention were also discovered to provide higher intrinsic palladium(II) activity than the catalyst systems and processes of background references. (Intrinsic palladium(II) activity can be determined by observing initial reaction rates under conditions when all the palladium loaded is initially present as olefin-active palladium(II); that is, in the absence of any accumulation of inactive forms.) Among the features of the inventive solutions and related processes which contribute to increased intrinsic palladium(II) activity are: 1) hydrogen ion concentrations greater than 0.10 mole/liter, 2) mixing conditions sufficient for the olefin oxidation rate to be governed by the chemical kinetics of the catalysis, not limited by the rate of olefin dissolution into the solution, 3) increased concentrations of dissolved olefin in solution provided by increasing its solubility (for example, by increasing the pressure of gaseous olefins), and 4) essential absence of sulfate ions. Surprisingly, the presence of chloride ions may also contribute to higher palladium activity, depending on the chloride concentration and the hydrogen ion concentration. Particularly, at hydrogen ion concentrations less than about 0.10 moles/liter, the presence of an effective concentration of chloride ions can increase palladium activity over the level with no chloride present.

In acidic aqueous solutions comprising palladium(II) (containing no coordinating ligands or anions other than water), $Pd^{II}$ exists in aqueous solution predominantly as its hydrolytic forms: tetraaquopalladium dication, $Pd(H_2O)_4^{2+}$, aquated palladium hydroxide, $Pd(OH)_2(H_2O)_2$ and solid phase palladium oxide which may be hydrated. These forms are interconverted by the following equilibria:ps

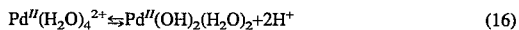

$$Pd^{II}(H_2O)_4^{2+} \rightleftharpoons Pd^{II}(OH)_2(H_2O)_2 + 2H^+ \qquad (16)$$

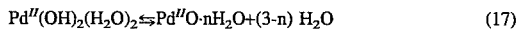

$$Pd^{II}(OH)_2(H_2O)_2 \rightleftharpoons Pd^{II}O \cdot nH_2O + (3-n) H_2O \qquad (17)$$

The two step-wise acid dissociation constants of reaction 16 have not been resolved ($Pd^{II}(OH)(H_2O)_3^+$ has not been detected), and the $pK_a$ of reaction 16, as written, is reported to be 2 in water, at or near zero ionic strength.

We have found that, contrary to the teaching of Matveev patents, the activity of the catalyst solution, specifically its volumetric olefin oxidation reaction rate, is independent of the vanadium content of phosphomolybdovanadate heteropolyacids, when tested at the same hydrogen ion concentration greater than 0.10 mole/liter, in the absence of sulfuric acid and sulfate ions, under mixing conditions sufficient for the rate to be governed by the chemical kinetics of catalysis. Since the chemical kinetics are first-order dependent on the concentration of the $Pd^{II}$, these findings indicate that under these conditions, the olefin-active $Pd^{II}$ is not coordinated by phosphomolybdovanadate heteropolyanions (since its reactivity does not depend on the identity of heteropolyanions). Accordingly, it appears that under these conditions, the olefin-active $Pd^{II}$ exists in solution as tetraaquopalladium, $Pd^{II}(H_2O)_4^{2+}$.

We further discovered that (in the effective absence of chloride ion) the rate of palladium catalyzed olefin oxidation in the polyoxoanion solution is highest with solutions having hydrogen ion concentrations greater than 0.1 mole/liter, and rates decrease substantially as the hydrogen ion concentration of the solution is decreased to 0.1 mole/liter and less. This indicates that the dicationic tetraaquopalladium, $Pd^{II}(H_2O)_4^{2+}$ is the most active form of palladium(II) under these conditions, and that as the hydrogen ion concentration of the solution is decreased to 0.1 mole/liter and less, an increasing fraction of the palladium(II) present as $Pd^{II}(H_2O)_4^{2+}$ is converted to less active (lower positively charged and less electrophilic) hydroxo-and/or oxo-forms by deprotonation of coordinated water, via equilibria such as reaction (16)(17). These hydrolytic forms are apparently less active due to their lower positive charge and decreased electrophilicity at $Pd^{II}$. Therefore, it is quite desirable to utilize polyoxoanion solutions having hydrogen ion concentrations greater than 0.10 mole/liter.

Hydrogen ion concentrations of polyoxoanion solutions, as recited herein, refer to the hydrogen ion concentration when essentially all the polyoxoanion is fully oxidized, which is when essentially all the vanadium is vanadium(V). The hydrogen ion concentrations of preferred polyoxoanion solutions often change when they are reduced, and these changes are not yet completely understood and predictable. Some solutions having hydrogen ion concentrations greater than 0.10 mole/liter when fully oxidized were discovered to have hydrogen ion concentrations less than even 0.01 mole/liter after being fully reduced by olefin oxidation. Since the theoretical equation for olefin oxidation (reaction (12)) potentially adds hydrogen ions into solution, the decreased hydrogen ion concentration in these reduced solutions presumably results from some re-equilibration of the initially produced vanadium(IV)-polyoxoanion species with water which consumes even more hydrogen ions than are potentially released by reaction (12).

None-the-less, olefin oxidation reactions using such an oxidized solution were found to proceed with an essentially constant rate characteristic of the initial hydrogen ion concentration up to high conversion of the vanadium(V) when provided with a sufficient combination of palladium concentration, dissolved olefin concentration, temperature, and other reaction conditions to achieve a relatively rapid olefin reaction. In contrast, when the reaction conditions were not sufficient to provide such a relatively rapid olefin reaction, the reaction rate would decelerate with vanadium(V) conversion, commensurate with a concomitant decrease in hydrogen ion concentration. Apparently, when sufficient reaction conditions are provided for relatively rapid olefin reaction, high vanadium(V) conversion occurs before a significant decrease in hydrogen ion concentration can occur by what must be relatively slow re-equilibration of the initially produced vanadium(IV)-polyoxoanions. In contrast, when the reaction conditions are not sufficient to provide relatively rapid olefin reaction, this slow re-equilibration of the initially produced vanadium(IV)-polyoxoanions can occur while they are relatively slowly formed and the reaction rate decelerates concomitant with the decreasing hydrogen ion concentration.

Background references for the oxidation of olefins with systems using palladium and vanadium-containing polyoxoacids generally teach that $PdCl_2$ and $PdSO_4$ are equivalent palladium catalysts. $PdSO_4$ completely ionically dissociates in water to sulfate ions and one or more hydrolytic forms of $Pd^{II}$, as governed by hydrogen ion concentration. Accordingly, one would be led to conclude that when $PdCl_2$ is added in the systems of the background references, chloride is similarly dissociated to give the same hydrolytic form(s) of $Pd^{II}$. However, the background references do not report the addition of chloride ions at a concentrations in excess of that coincidental to providing $PdCl_2$. Indeed, the background references generally promote that chloride-free systems are most desirable. The Wacker system, with its higher concentrations of chloride, typically about 2 moles/liter, exhibits a severe, second order inhibition of the ethylene oxidation rate by chloride ion concentration.

Inventive aqueous catalyst solutions and related processes, by having an effective concentration of chloride ions, give substantially improved catalyst stability with little to only moderate inhibition of the intrinsic $Pd^{II}$ activity. Moreover, since a greater fraction of loaded palladium can be maintained in the active $Pd^{II}$ form, greater productivity can be obtained from the total palladium load in continuous operation by the addition of an effective concentration of chloride ions.

In tested embodiments with hydrogen ion concentrations less that 0.1 mole/liter, the presence of chloride ion at 5 millimoles/liter does not inhibit $Pd^{II}$ activities to any important degree. With chloride ion at 25 millimoles/liter, $Pd^{II}$ activities were within $40 \geq 60\%$ of those in the absence of chloride ions, and still about 100 times greater than for a typical Wacker catalyst system under comparable conditions.

Even more surprisingly discovered, as the hydrogen ion concentration is decreased below 0.1 moles/liter, a region where $Pd^{II}$ activity in the absence of chloride ions decrease substantially, $Pd^{II}$ activity in the presence of an effective concentration of chloride ions can be substantially maintained. Said another way, intrinsic $Pd^{II}$ activity in the presence of chloride can exceed $Pd^{II}$ activity in the absence of chloride. In tested embodiments with hydrogen ion concentrations about 0.01 mole/liter, $Pd^{II}$ activity in the presence of 25 millimoles/liter chloride ion were about 5 times greater than those without chloride.

When chloride ions are added to solutions of acidic solutions of $Pd^{II}$ in water, a series of aquated chloride complexes are formed as the chloride ion concentration is increased. Where the acidity is such to provide $Pd^{II}(H_2O)_4^{2+}$ as the hydrolytic form, the series is as follows (in each of the following equilibria a chloride ion is added and a water is lost, to the right as written):

$$Pd(H_2O)_4^{2+} \rightleftharpoons PdCl(H_2O)_3^+ \rightleftharpoons PdCl_2(H_2O)_2 \rightleftharpoons PdCl_3(H_2O)^- \rightleftharpoons PdCl_4^= \qquad (18)$$

As the acidity of a solution is decreased, each of the complexes containing coordinated water can dissociate a hydrogen ion to leave a complex of coordinated hydroxide. With the successive replacement of coordinated water in $Pd(H_2O)_4^{2+}$ by chloride ions (equation (18)), the positive charge on the palladium complex is decreased and the $pK_a$ for deprotonation of remaining coordinated water is increased. This increase in $pK_a$ by chloride coordination appears sufficient so that the chloro-aquo species formed in the presence of moderate amounts of chloride, are not significantly deprotonated to chloro-hydroxo species as the hydrogen ion concentration is decreased to at least 0.01 millimoles/liter. Thereby, the $Pd^{II}$ catalyst activity of these chloride-bound catalysts at hydrogen ion concentrations greater than 0.1 mole/liter can be substantially maintained on decreasing the hydrogen ion concentration to at least 0.01 millimoles/liter. Further, the chloro-aquo species appear substantially more active for olefin oxidation than hydroxo-aquo species (such as $Pd^{II}(OH)_2(H_2O)_2$) formed when $Pd(H_2O)_4^{2+}$ is deprotonated as the hydrogen ion concentration is decreased towards 0.01 millimoles/liter.

We have also discovered that in using the inventive chloride-comprising catalyst solutions for the oxidation of olefins, chlorinated organic by-products are not formed or are formed in amounts insignificant relative to the amounts formed with the Wacker catalyst system. Apparently, the essential absence of copper ions in preferred catalyst solutions which include chloride, substantially avoids significant oxychlorination of organics.

The polyoxoanion in the solutions and processes of the present invention appears to provide two functions which are not provided with vanadium alone in aqueous solution. First, the polyoxoanion solution provides an environment for dissolution of suitably high concentrations of vanadium. In acidic aqueous solutions with hydrogen ion concentrations comparable to preferred solutions of the present invention, vanadium(V) alone exists predominantly as the pervanadyl ion, $VO_2^+{}_{aq}$, whose solubility is limited; at saturation, it deposits solid $V_2O_5$. Likewise, vanadium(IV) alone exists predominantly as the vanadyl ion, $VO^{2+}{}_{aq}$, which saturates with respect to insoluble reduced vanadium oxides. In contrast, polyoxoanions comprising vanadium can provide vanadium solubilities to much higher concentrations, such as the decimolar to molar level concentrations of vanadium utilized in preferred solutions and processes of the present inventions.

Second, the polyoxoanion solution appears to enable suitably rapid reaction of vanadium(IV) with oxygen, to regenerate vanadium(V) (reaction (13)). Although pervanadyl ion is capable of palladium-catalyzed oxidation of olefins, in a reaction similar to reaction (12), vanadyl ion alone reacts only very slowly with dioxygen to regenerate pervanadyl. In contrast, in our preferred polyoxoanion solutions, polyoxoanions comprising vanadium(IV) react very rapidly with dioxygen, thereby providing preferred processes of the present invention. Moreover, when vanadyl(IV) ion is present in the polyoxoanion solution, it too can react rapidly with dioxygen. Preferred polyoxoanions comprising vanadium, which enable particularly rapid oxidation of vanadium(IV) to vanadium (V), further comprise phosphorus or molybdenum. Particularly preferred polyoxoanions further comprise both phosphorus and molybdenum.

Our processes, which include reaction of preferred polyoxoanion solutions comprising vanadium(IV) with dioxygen, can proceed with volumetric dioxygen reaction rates of at least 1 (millimole dioxygen/liter solution)/second and up to multiplicatively greater rates than those in background references. Improved volumetric dioxygen reaction rates can be achieved, in part, by operating the vanadium(IV)-dioxygen reaction process under more efficient gas-liquid mixing conditions. It was surprisingly discovered that these even improved rates are still limited by the diffusion (mass transfer) of dioxygen into the aqueous solution, so that still more rapid rates could be achieved under still more efficient gas-liquid mixing conditions.

The air reactors in a Wacker-type acetaldehyde manufacturing plant provide efficient gas-liquid mixing for achieving the commercially practicable dioxygen reaction rates provided by the present invention. The dioxygen reaction rates so achieved are suitable for utilization in manufacturing a carbonyl product using a Wacker-type manufacturing plant.

We also surprisingly discovered that the presence of sulfate salts in aqueous polyoxoanion solutions, such as those of background references which are prepared by acidification using sulfuric acid, results in slower volumetric dioxygen reaction rates. Rates of reaction which are limited by diffusion (mass transfer) of a gas into a solution are a positive function of the solubility of the gas in the solution. The presence of sulfate salts may decrease ("salts-out") the solubility of dioxygen in aqueous catalyst solutions and so decrease volumetric dioxygen reaction rates, but there may be other explanations. In any case, in comparisons under the same mixing and reaction conditions, polyoxoanion solutions comprising vanadium(IV) react with dioxygen at greater volumetric reaction rates when the solution is essentially free of sulfate ions.

Background references teach that volumetric reaction rates of reduced polyoxoanion solutions with dioxygen decrease as the recited "pH"s of solutions are decreased towards 1. Matveev patents specifically teach that with "lower pH values" (their preferred "pH" is said to be 1), the rate of the oxygen reaction is appreciably diminished. In contrast, we have found that our solutions and processes oxidize vanadium(IV) in aqueous solution by dioxygen at substantially undiminished volumetric dioxygen reaction rates over a range of hydrogen ion concentrations extending substantially greater than 0.1 mole/liter. Consequently, we are able to use high hydrogen ion concentrations (e.g. greater than 0.1 mole/liter) to promote palladium catalyst stability and olefin oxidation activity and yet maintain exceptional polyoxoanion oxidant regeneration rates.

Catalyst Solution and Process Description:

The following is additional description of the aqueous solutions of the present invention and their use in processes for the oxidation of olefins to carbonyl products:

Olefins:

Olefins suitable for oxidation according to the process of this invention are organic compounds having at least one carbon-carbon double bond, or mixtures thereof. Examples of suitable olefins are compounds represented by the formula RR'C=CHR" wherein R, R', and R" each represents a hydrogen atom, a hydrocarbyl substituent, or a heteroatom selected from the group halogen, oxygen, sulfur, or nitrogen, which may be the same or different, and which may be connected in one or more ring structures. Although there is no inherent limit on the size of the hydrocarbyl substituents R, R', or R", they suitably may be linear, branched, or cyclic as well as mononuclear or polynuclear aromatic. The hydrocarbyl substituents described may be $C_1$ to $C_{20}$, although $C_1$ to $C_4$ are especially preferred. Each hydrocarbyl substituent may also contain one or more heteroatoms of halogen, oxygen, sulfur, or nitrogen.

The olefins themselves may be either cyclic or acyclic compounds. If the olefin is acyclic, it can have either a linear structure or branched structure, and the carbon-carbon double bond may be either terminal ("alpha-olefins") or non-terminal ("internal olefins"). If the olefin is cyclic, the carbon-carbon double bond may have either one, both, or neither of the carbon atoms of the double bond within the cycle. If the olefin contains more than one carbon-carbon double bond, the double bonds may be either conjugated or unconjugated.

Examples of suitable olefins are ethylene, propylene, 1-butene, 2-butene (cis and trans), 1-pentene, 2-pentene, 1-hexene, 2-hexene, 3-hexene, 1-octene, 1-decene, 1-dodecene, 1-hexadecene, 1-octadecene, 1-eicosene, 1-vinylcyclohexane, 3-methyl-1-butene, 2-methyl-2-butene, 3,3-dimethyl-1-butene, 4-methyl-1-pentene, 1,3-butadiene, 1,3-pentadiene, 1,5-hexadiene, 1,7-octadiene, 1,9-decadiene, cyclopentene, cyclohexene, cycloheptene, cyclooctene, cyclododecene, 1,5-cyclooctadiene, 1,5,9-cyclododecatriene. Preferred olefins are ethylene, propylene, 1-butene, cis-2-butene, trans-2-butene, 3-methyl-1-butene, 2-methyl-2-butene, 4-methyl-1-pentene, cyclopentene, and cyclohexane. Mixtures of olefins may also be oxidized. Preferred mixtures of olefins comprise olefins which yield a common carbonyl product on oxidation, for example, mixtures of 1-butene, cis-2-butene, and/or trans-2-butene for the production of 2-butanone, and mixtures of 3-methyl-1-butene and 2-methyl-2-butene for the production of 3-methyl-2-butanone.

The olefins introduced in the process of the present invention may be diluted by other compounds which are inert towards the oxidation reaction condition, for example, by dinitrogen, carbon dioxide, water and saturated aliphatic compounds such as methane, ethane, propane, butane, cyclohexane, and the like. For example, 1-butene, cis-2-butene, and/or trans-2-butene for the oxidation process may be provided in admixture with butane; cyclohexane may be provided in admixture with cyclohexane and/or benzene.

With gaseous olefins, the process involves mixing a gaseous olefinic phase with the aqueous catalyst solution. With olefins which are liquid under the reaction conditions, the process typically involves mixing an olefinic phase with the aqueous catalyst solution. Surfactants and/or cosolvents may optionally be used to increase the solubility of the olefin in the aqueous solution, or to increase the efficiency of diffusion (mass transfer) of olefins into the aqueous catalyst solution, or both. See for example, the surfactants and cosolvents disclosed in U.S. Pat. Nos. 4,434,082 and 4,507,507. Alternatively, cosolvents which miscibilize otherwise separate olefinic and aqueous phases may be added. See for example, the cyclic sulfone cosolvents disclosed in U.S. Pat. No. 4,507,506.

Dioxygen:

Dioxygen may be introduced into processes of the present invention as oxygen, air, or mixtures thereof (enriched air). The dioxygen may be in admixture with an inert gas, for example, dinitrogen, carbon dioxide, water vapor. The dioxygen is typically added to the process at a partial pressure at least equal to its partial pressure in air at one atmosphere pressure.

Carbonyl Products:

The carbonyl products of the present invention are organic compounds comprising at least one carbon-oxygen double bond: aldehydes, ketones, carboxylic acids, and derivatives thereof. Acetaldehyde is the initial catalytic reaction product of ethylene oxidation. Ketones are typically the initial catalytic reaction products of oxidations of higher olefins. For olefins which have double-bond positional isomers, mixtures of isomeric ketones may be obtained. For example, 1-hexene may yield mixtures of 2-hexanone and 3-hexanone.

The process of the present invention is highly selective to the initial catalytic reaction products (acetaldehyde and ketones); they are formed with selectivities typically higher than 80%, usually higher than 90%, and often higher than 95%. These carbonyl products may be separated in high yield from the reaction solution. Alternatively, the initial products may be further oxidized by continued exposure to the oxidizing reaction conditions, especially the dioxygen reaction for regenerating the oxidant. Typically, the initial carbonyl products are oxidized to carboxylic acids by such continued exposure. For example, acetaldehyde may be converted to acetic acid, and cyclohexanone may be converted to adipic acid.

Palladium Catalysts:

The palladium catalyst of the present invention may comprise any palladium containing material which is suitable for oxidation of olefins under the oxidation process conditions. The active palladium catalyst in the solution may be provided to the solution as palladium(0), for example palladium metal, or a palladium compound. Palladium(II) salts are convenient sources of palladium catalyst. Preferred palladium(II) salts include palladium acetate ($Pd(CH_3CO_2)_2$), palladium trifluoroacetate ($Pd(CF_3CO_2)_2$), palladium nitrate ($Pd(NO_3)_2$), palladium sulfate ($PdSO_4$), palladium chloride ($PdCl_2$), disodium tetrachloropalladate ($Na_2PdCl_4$), dilithium tetrachloropalladate ($Li_2PdCl_4$), and dipotassium tetrachloropalladate ($K_2PdCl_4$).

It is preferred that palladium catalyst is dissolved in the aqueous solution. When palladium(0) metal is the palladium source, it is dissolved by oxidation to palladium(II) by the polyoxoanion oxidant. This oxidative dissolution of palladium(0) to give active palladium catalyst generally requires heating of the mixture, and is accelerated in the present invention by the presence of chloride ions. Palladium(0) may be provided as palladium metal or colloids. Palladium metal may be provided as bulk metal (shot, wire, foil), palladium sponge, palladium black, palladium powder, and the like.

Since palladium catalyst activity depends on such factors as the identity of the olefin, olefin concentration dissolved in aqueous solution, chloride ion concentration, hydrogen ion concentration, sulfate ion concentration, temperature, and other reaction conditions, the palladium concentration in the aqueous catalyst solution can vary in a broad range, typically within 0.01 to 100 millimoles/liter. Although the preferred palladium concentration will depend on other such aspects of the embodiment, it can be readily determined for each application. The ratio of the molar palladium concentration to the molar polyoxoanion concentration will be an effective amount but less than 1. Preferred palladium concentrations are generally 1/10 to 1/10000 of the concentration of the polyoxoanion. For oxidation of gaseous olefins, such as ethylene, propylene, and butenes, preferred palladium concentrations are typically 0.1 to 10 millimolar. The present invention enables practical ethylene oxidation reactions using palladium catalyst concentrations less than 1.0 millimolar.

Polyoxanion and Polyoxoacid Oxidants:

Polyoxoanions, and corresponding polyoxacids, utilized as oxidants in the present processes, are isopolyoxoanions and heteropolyoxoanions comprising vanadium. A treatise on polyoxoanion compositions, structures, and chemistry is found in *Heteropoly and Isopoly Oxometallates* by M. T. Pope, Springer-Verlag, N.Y., 1983, which is incorporated by reference entirely. Polyoxoanions comprising vanadium have at least one vanadium nucleus and at least one other metal nucleus, which may be another vanadium nucleus or any other metal nucleus which combines with vanadium in an oxoanion composition.

Examples of suitable polyoxoanions and polyoxoacids are represented by the general formula:

wherein:

H is proton bound to the polyoxoanion;

V is vanadium;

O is oxygen;

X is selected from the group consisting of boron, silicon, germanium, phosphorus, arsenic, selenium, tellurium and iodine—preferably phosphorus;

M and M' are the same or different and are independently selected from the group consisting of tungsten, molybdenum, niobium, tantalum, and rhenium—preferably at least one of M and M' is molybdenum;

y,a,b,c, and m are individually zero or an integer (a is zero for isopolyoxoanions and mixed isopolyoxoanions, or a is an integer for heteropolyoxoanions);

x, and z are integers; and, b+c+x is greater than or equal to 2.

Preferred polyoxoanions are the so-called Keggin heteropolyoxoanions represented by the above general formula, additionally defined wherein:

a is one, b+c+x is 12;

z is 40.

Most preferred are Keggin heteropolyoxoanions and heteropolyacids comprising phosphorus, molybdenum, and vanadium (phosphomolybdovanadates), represented by the following formula when in the oxidized state:

$$[H_yPMo_{(12-x)}V_xO_{40}]^{(3+x-y)-}$$

wherein:

x and y are integers;

$0 > x \leq 12$; and, $0 \leq y \leq (3+x)$.

More specifically, $0 \leq y \leq (3+x)$ for polyoxoanion species and $0 \leq y \leq (3+x)$ for polyoxoacid species. Except when a polyoxo species is completely deprotonated (i.e., y=0) or completely protonated (i.e., y=(3+x)), it is both a polyoxoanion species and a polyoxoacid species. However, protons dissociated into solution may also be considered in designating a solution as comprising a polyoxoacid, even though all the polyoxo species present may be fully deprotonated in the solution. The Keggin phosphomolybdovanadates have been found to be anions of very strong acids, and are believed never to be fully protonated in aqueous solution.

Preferred phosphomolybdovanadate solutions have phosphorus, molybdenum, and vanadium present in relative molar amounts approximating the composition of the Keggin heteropolyoxoanions; that is ([Mo]+[V]) ≅12[P]). However, solutions having an excess of one or two components over these ratios are also intended. In particular, excess phosphoric acid or phosphate salt may be present. It is also intended that the Keggin phosphomolybdovanadate solutions may optionally comprise excess vanadium (for example, as $VO_2^+$) over the Keggin ratios.

The net negative charge of the polyoxoanions is balanced by countercations which are protons and/or salt cations. When only protons are present as countercations (when y=(3+x) for the Keggin phosphomolybdovanadic acid), one has a "free acid" polyoxoacid. When one or more salt cations are present as countercations, in place of protons, one has a polyoxoanion salt, also called a salt of the polyoxoacid. When both protons and salt cations are present, one has a partial salt of the polyoxoacid; the free polyoxoacid is partially neutralized.

Suitable salt countercations are those which are inert, or in some way advantageous (for example, $Pd(H_2O)_4^{2+}$, $VO_2^+$), under the reaction conditions. Preferred salt countercations are alkali metal cations and alkaline earth cations which do not precipitate insoluble polyoxoanion salts; for example: lithium, sodium, potassium, beryllium, and magnesium cations, or mixtures thereof. Most preferred are lithium ($Li^+$), sodium ($Na^+$), and magnesium ($Mg^{2+}$) cations. Mixtures of salt countercations may be present.

The Keggin phosphomolybdovanadates exist in aqueous solution as equilibrium mixtures of anions varying in vanadium and molybdenum content (varying in x). Moreover, for each value x such that 1>x>11, there are a number of positional isomers for the placement of the vanadium and molybdenum in the Keggin structure: for x=2 there are five isomers, for x=3 there are 13 isomers, for x=4 there are 27 isomers, and so on. Each of these compositional and isomeric species has its own acid dissociation constants which determine the extent to which it is protonated at a given hydrogen ion concentration is solution. (That is, each compositional and isomeric species can have its own average y value in a given solution.) Accordingly, the compositions of aqueous Keggin phosphomolybdovanadate solutions are not generally easily characterized in terms of a their component species $[H_yPMo_{(12-x)}V_xO_{40}]^{(3+x-y)-}$ and their individual concentrations.

The present inventors have adopted a simplified, yet definitive, method of designating the elemental constitution of solutions containing Keggin phosphomolybdovanadate free acids or alkali metal salts in the oxidized state, in terms of the general formula:

$$\{A_pH_{(3+n-p)}PMO_{(12-n)}V_nO_{40}\}$$

wherein:

A is an alkali metal cation ($Li^+$, $Na^+$);

the designated concentration of the solution is its phosphorus concentration, usually reported in moles/liter (molar, M);

phosphorus, molybdenum, vanadium are present in the concentration ratios defined by n, and 0<n<12;

alkali metal is present in solution in a concentration ratio to phosphorus defined by p, and $0 \leq p \leq (3+n)$.

Accordingly, the negative charge of the designated Keggin formula in fully deprotonated form, 3+n, is balanced in solution by p+q monocations. Since this designation refers to a mixture of polyoxoanions, n and p may be non-integral.

This designation completely defines the elemental constitution of an aqueous solution. A given elemental constitution will have one thermodynamic equilibrium distribution of species comprising its component elements. When the phosphorus, molybdenum, and vanadium in these solutions are predominantly present in Keggin heteropolyanions of formula $[H_yPMo_{(12-x)}V_xO_{40}]^{(3+x-y)-}$(which is usually the case in the preferred solutions of the present invention), then n is approximately equal to the average value of x among the distribution of species. The concentration of free hydrogen ions in such a solution is approximately the concentration of phosphorus multiplied by the difference between p and the average value of y among the distribution of species. When the phosphomolybdovanadates are the only acids in solution, the acidity of the solution can be set by the phosphomolybdovanadate concentration, its identity (n), and the ratio of alkali cations (p) to hydrogen ions (3+n-p).

Preferred phosphomolybdovanadate solutions following this method of designation have 0<n<12. Especially preferred solutions have 2<n<6.

The concentration of the polyoxoanion can be varied over a broad range, typically within 0.001 to 1.0 moles/liter. Preferred concentrations depend strongly on the composition of the polyoxoanion, the specific application, and the reaction conditions. For oxidation of gaseous olefins, such as ethylene, propylene, and butenes, preferred polyoxoanion concentrations are typically 0.1 to 1.0 molar.

The polyoxoanions can be provided to the aqueous catalyst solution by dissolving prepared polyoxoanion solids (free acids or salts) or by synthesis of the polyoxoanion directly in the aqueous solution from component elemental precursors. Suitable polyoxoanion solids and polyoxoanion solutions can be prepared by methods in the art, such as in the background references cited in the section Background of the Invention. For those solutions and related processes of the present invention which are not required to be essentially free of sulfate ions, the polyoxoanion may be prepared by the methods which add sulfuric acid in the aqueous solution, U.S. Pat. No. 4,146,574, incorporated by reference entirely, teaches a method for the preparation of solutions consisting of free phosphomolybdovanadic acids.

Alternatively, the present invention provides a process for the direct preparation of acidic aqueous solutions of salts of polyoxoacids comprising vanadium without the introduction of mineral acids other than the polyoxoacid or its component oxoacids. The acidity of the resulting solutions is readily adjusted by the balance of salt cations and protons in the salt.

Process for the Preparation of Polyoxoanion Solutions:

According to the present invention, acidic aqueous solutions of salts of polyoxoanions comprising vanadium are prepared by dissolving in water oxides, oxoacids, and/or salts of oxoanions of the component polyoxoanion elements, and optionally salts of carbonate, bicarbonate, hydroxide, and oxide, such that the resulting ratio of protons and salt countercations balancing the net negative charge of the resulting polyoxanions in the solution provides a hydrogen ion concentration in solution greater than $10^{-5}$ moles/liter.

Preferably, the resulting hydrogen ion concentration is greater than $10^{-3}$ moles/liter, and most preferably, greater than 0.1 moles/liter.

Preferred Keggin phosphomolybdovanadate salts are preferably prepared in solution by dissolving vanadium oxide and/or vanadate salt, molybdenum oxide and/or molybdate salt, phosphoric acid and/or phosphate salt, and optionally carbonate, bicarbonate, and/or hydroxide salt in water, such that the ratio of protons (3+n-p) and other salt countercations (p) balancing the negative charge of the phosphomolybdovanadates (3+n) in the solution provides the desired hydrogen ion concentration in the solution. Preferably the vanadium, molybdenum, and phosphorus reactants are added in ratios corresponding to the desired average Keggin composition of the solution.

The temperature of the preparation process may be within the range 50 to 120° C. It is most conveniently operated in boiling water at about 100° C.

Typically, a solution of alkali vanadate, for example sodium metavanadate ($NaVO_3$) or hexasodium decavanadate ($Na_6V_{10}O_{28}$), is prepared in water. This solution can be prepared by dissolving solid salts into water, but is prepared most economically by adding alkali carbonate (e.g. $Na_2CO_3$), alkali bicarbonate (e.g. $NaHCO_3$), or alkali hydroxide (e.g. $NaOH$) to a suspension of vanadium oxide ($V_2O_5$) in water and heating to complete the reactive dissolution. Then, molybdenum oxide and phosphoric acid (or alkali phosphate salt) are added to the alkali vanadate solution and heating is continued to complete the preparation of an acidic aqueous phosphomolybdovanadate salt solution. Finally, the solution is adjusted to the desired concentration by evaporation and/or volumetric dilution.

Additional basic alkali salt (carbonate, bicarbonate, of hydroxide) can be added at any point during or after the preparation to further neutralize the resulting polyoxoacid solution and obtain decreased acidity; that is, to adjust the value p in the designation $\{A_pH_{(3+n-p)}PMo_{(12-n)}V_nO_{40}\}$.

When solutions having the same phosphorus concentration and vanadium content, n, but different acidities (different p) are already prepared and available, solutions of intermediate acidity (intermediate p) can be prepared by blending the available solutions in the appropriate volumetric ratios. More generally, solutions of determinate composition can be prepared by blending measured volumes of two or more solutions, of known phosphorus concentration, vanadium content (n), and salt cation content (p).

Hydrogen Ions:

Hydrogen ions and hydrogen ion concentrations, as used herein, have their usual meaning. Hydrogen ions in aqueous solution are free, aquated protons. Hydrogen ion concentration is not meant to include protons bound in other solute species, such as in partially protonated polyoxoanions or bisulfate.

Hydrogen ions may be provided by providing an acid which dissociates protons when dissolved in aqueous solution. Organic and mineral acids which are sufficiently acidic to provide the desired hydrogen ion concentration are suitable. The acid is preferably inert to oxidation and oxidative destruction under intended process conditions. Acid anhydrides and other materials which hydrolytically release protons on reaction with water may likewise be used to provide hydrogen ions.

Strong mineral acids, such as polyoxoacids, sulfuric acid, hydrochloric acid, and the like, are preferred sources of hydrogen ions. Particularly preferred are polyoxoacids. Certain solutions and related processes of the present invention are essentially free of sulfuric acid. Certain solutions and related processes of the present invention are essentially free of mineral acids other than of polyoxoacids and hydrohalic acids.

Hydrogen ion concentrations of polyoxoanion solutions, as recited herein, refer to the hydrogen ion concentration when essentially all the polyoxoanion is in its fully oxidized state, which is when essentially all the vanadium in the polyoxoanion solution is in the vanadium(V) state. It has been determined that the acidity of the preferred polyoxoanion solutions change with reduction, and these changes are not yet completely understood and predictable. (For example, 0.30M $\{Na_3H_3PMo_9V_3O_{40}\}$ solution has a hydrogen ion concentration greater than 0.10 moles/liter in equilibrated fully oxidized state, but less than 0.01 moles/liter in equilibrated fully reduced state, when all the vanadium is in the vanadium(V) state.) The preferred polyoxoanions of the present invention are most readily prepared essentially fully oxidized, and can be readily returned to that condition by reaction with dioxygen according to processes of the present invention. In the context of determining hydrogen ion concentrations, the phrase "when essentially all the oxidant is in its oxidized state" means when the solution of oxidant is sufficiently oxidized so as to have the hydrogen ion concentration which is obtained when it is fully oxidized.

The hydrogen ion concentration is sufficient to provide an acidic solution having a hydrogen ion concentration greater than $10^{-5}$ mole/liter. Preferably, the hydrogen ion concentration is greater than $10^{-3}$ mole/liter, and most preferably, greater than 0.1 moles/liter. Certain solutions and related processes of the present invention specifically comprise hydrogen ions at a concentration greater than 0.1 mole per liter of solution when essentially all the oxidant is in its oxidized state.

Hydrogen Ion Concentration Measurement:

Background references for polyoxoanion solutions generally recite "pH" values for the solution but do not specify methods for determining them. pH is technically defined as $-\log[\alpha_{H+}]$, where $\alpha_{H+}$ is the hydrogen ion activity. The hydrogen ion activity is identical to the hydrogen ion concentration in otherwise pure water. The hydrogen ion activity and hydrogen ion concentration are still good approximations of each other in aqueous solutions which are low in ionic strength and otherwise approximately ideal. Solutions of polyoxoacids at decimolar concentrations, typical in background references and in the present invention, have high ionic strength and are very non-ideal solutions, especially when they also contain high concentrations of other mineral acid salts.

The common method to obtain pH measurements of aqueous solutions uses pH-sensitive glass electrodes, monitored with an electrometer (a "pH meter"). Such electrodes are known to exhibit an "acid error", measuring increasingly incorrect "pH"s as pH is decreased below 2 and especially at real pH 1 and below. Moreover, successful measurement at any pH level requires calibration with solutions of similar ionic media and ionic strength. Common calibration solutions for pH meters are at relatively low ionic strength and of very different ionic media compared to decimolar polyoxoanion salt solutions. We have found that using different common calibration solutions can lead to different "pH" measurements for the same polyoxoanion solution. Unless a disclosure contains a recitation of the method of "pH" measurement for these solutions, including the methods of calibration, one having ordinary skill does not know what a reported "pH" value really means, nor how to reproduce it.

We have developed a more definitive method of measuring hydrogen ion concentration in the polyoxoanion solutions of the present invention. It Is based on the observation (by $^{31}$P- and $^{51}$V-NMR studies) that in solutions designated $\{A_pH_{(4-p)}PMo_{11}VO_{40}\}$, $PMo_{11}VO_{40}^{4-}$ is essentially the only species present. It was further determined that $PMo_{11}VO_{40}^{4-}$ remains completely unprotonated even in concentrated solutions (>0.3M) of the free acid $\{H_4PMo_{11}VO_{40}\}$. (Species having two or more vanadia do become protonated in acidic aqueous solutions.) Accordingly, for solutions of $\{A_pH_{(4-p)}PMo_{11}VO_{40}\}$, the hydrogen ion concentration is the phosphorus concentration multiplied by (4-p). Such solutions were prepared and used to calibrate glass pH electrodes for measurement of the hydrogen ion concentration of solutions of undetermined acidity, having the same phosphorus concentration. This method is illustrated in the examples.

Sulfate ions:

Sulfate ions, as used herein, is meant to include both sulfate dianion ($SO_4^=$) and bisulfate anion ($HSO_4^-$). Since sulfuric acid is a very strong acid, addition of sulfuric acid to an aqueous solution results in a solution of sulfate and/or bisulfate ions, depending on the acidity of the solution.

Certain solutions and related processes of the present invention are "essentially free of sulfate ions". This means the concentration of sulfate and/or bisulfate salts is sufficiently low so that their undesired influence on palladium catalyst activity, palladium catalyst stability, volumetric olefin oxidation rate, or volumetric dioxygen reaction rate is not significantly manifested. This can be readily determined experimentally. Preferably, these solutions are free of sulfate and/or bisulfate salts.

Chloride ions:

Chloride ions can be provided by any chloride-containing compound which readily dissolves in water, or reacts with water, to release free, aquated chloride ions into solution. Suitable chloride-containing compounds include hydrochloric acid, chlorides and oxychlorides of oxoanion-forming elements, chloride complexes and chloride salts, and the like. Examples of chlorides and oxychlorides of the oxoanion-forming elements are $PCl_5$, $POCl_3$, $VOCl_3$, $VOCl_2$, $MoOCl_4$, and the like. Suitable chloride salt countercations are those which are inert, or in some way advantageous (for example, $Pd^{II}$), under the reaction conditions and which do not precipitate insoluble polyoxoanion salts out of aqueous solution. Preferred chloride-containing compounds are hydrochloric acid, palladium chloride compounds, and chloride salts of alkali metal cations and alkaline earth cations which do not precipitate insoluble polyoxoanion salts. Examples of suitable palladium chloride compounds are $PdCl_2$, $Na_2PdCl_4$, $K_2PdCl_4$, and the like. Examples of suitable alkali and alkaline earth salts are lithium chloride (LiCl), sodium chloride (NaCl), potassium chloride (KCl), and magnesium chloride ($MgCl_2$).

Significant amounts of chloride may also be present as impurities in the starting materials for polyoxoanion preparation. For example, we surprisingly discovered that several commercial sources of sodium vanadate are sufficiently contaminated with chloride to provide effective amounts of chloride in polyoxoanion solutions prepared from them.

Certain solutions and related processes of the present invention comprise chloride at concentrations greater than coincidental to using $PdCl_2$ as the palladium source; that is greater than twice the palladium concentration. Preferably, the chloride concentration is greater than four times the palladium concentration. Most preferably, the chloride concentration is at least 5 millimolar. There is no particular upper limit on the chloride concentration, but is preferably less than a concentration at which the palladium catalyst activity becomes inversely dependent on the square of the chloride concentration. Chloride is usually present at a concentration of 0.001 to 1.0 moles/liter, preferably 0.005 to 0.50 moles per liter, and most preferably 0.010 to 0.100 moles per liter. Typically, the chloride is present in millimolar to centimolar concentrations, where unquantified "millimolar concentrations" refers to concentrations of 1.0 to 10.0 millimolar, and unquantified "centimolar concentrations" refers to concentrations of 10.0 to 100.0 millimolar. Generally, the chloride is present in these solutions at a molar ratio of 10/1 to 10,000/1 relative to palladium.

Chloride may also be provided by copper chlorides, for example by residual Wacker catalyst retained in an industrial plant designed to operate the Wacker process chemistry after draining the Wacker catalyst solution. However, the chloride-containing solutions and related processes of the present invention are preferably essentially free of copper ions. "Essentially free of copper ions ions" means the olefin oxidation process with the solution does not produce substantially higher amounts of chlorinated organic by-products than a corresponding solution which is free of copper ions.

Process Conditions:

Broadly, olefin oxidation processes of the present reaction are conducted under oxidative conditions sufficient to oxidize the olefin to a carbonyl product. Likewise, in processes involving reaction of dioxygen, the dioxygen reaction is conducted under oxidative conditions sufficient to utilize dioxygen to oxidize the olefin, or intermediately, to regenerate the polyoxoanion oxidant in its oxidized state.

The preferred temperature range for processes of the present invention varies with the identity of the olefin and is interdependent with such factors as the olefin concentration in aqueous solution, chloride ion concentration, palladium concentration, and other factors which determine reaction rates. Increasing temperature generally provides increased reaction rates, although these increases are slight for reactions which are limited by diffusion. In some cases, lower temperatures may be preferred to avoid troublesome side-reactions. In two-stage operation, temperatures for the olefin reaction and the dioxygen reaction can be set independently. Generally, temperatures utilized in processes of the present invention may range from about 20° to about 200° C., usually in the range 60° to 160° C. For gaseous olefins, such as ethylene, propylene, and butenes, the temperature is preferably in the range 90° to 130° C.

Pressures for the processes of the present invention depend strongly on the nature of the olefin, whether gaseous or liquid under the reaction conditions, whether dioxygen reaction is conducted simultaneously or separately with the olefin oxidation reaction, whether oxygen is added as oxygen or air, and reaction temperatures. For example, at reaction temperatures less than 100° C., the atmospheric boiling point of water, with olefins which are liquid under the reaction conditions, in the absence of dioxygen, the olefin oxidation process may be conveniently conducted at atmospheric pressure. For temperatures near or above 100° C. and above, water vapor contributes significantly to the total pressure in the reactor device.

For gaseous olefins, elevated partial pressure is usually utilized to increase the concentration of olefin in the gas phase in contact with the liquid phase and thereby increase its solubility in the liquid phase, to increase reaction rates and decrease reactor volumes. Generally, gaseous olefins are reacted at partial pressures of 1 atmosphere to 100 atmospheres, typically in the range 4 atmospheres (about 60 psi) to 20 atmospheres (about 300 psi). In two-stage mode, gaseous olefins are preferably reacted at partial pressures in the range of 8 atmospheres (about 120 psi) to 12 atmospheres (about 180 psi).

In certain solutions and processes of the present invention, olefin is dissolved in the catalyst solution at concentrations effective for its rate of oxidation to be at least 1 (millimole olefin/liter solution)/second, or at concentrations effective to provide a palladium turnover frequency of at least 1 (mole olefin, mole palladium)/second, or preferably both. Reaction conditions and mixing conditions which meet these criteria can be established by routine experimentation, for example using the procedures of the following Examples. In certain solutions and processes of the present invention, the olefin is dissolved at concentrations such that its rate of oxidation is not further increased by further increasing its concentration (olefin saturation kinetics).

For dioxygen reaction processes, elevated partial pressure is usually utilized to increase the concentration of oxygen in the gas phase in contact with the liquid phase, to increase reaction rates and decrease reactor volumes. Generally, oxygen is reacted at partial pressures of 0.2 atmosphere (1 atmosphere air) to 100 atmospheres, typically in the range 0.2 atmospheres to 20 atmospheres, and preferably in the range 1 atmosphere (about 15 psi) to 10 atmosphere (about 150 psi).

For oxidation of gaseous olefins by dioxygen in two stage mode, the total pressures in the olefin reactor and the dioxygen reactor are typically similar, but may be varied independently. In two stage mode, compressed air is typically used, but oxygen could be used as well.

For oxidation of gaseous olefins by dioxygen in one-stage mode, oxygen is typically used and olefin and oxygen are typically fed in near stoichiometric ratios, about 2:1.

Liquid olefins can be reacted neat or in combination with substantially inert diluents. Generally, the concentration of the liquid olefin in a second liquid olefinic phase is increased to increase reaction rates and decrease reactor volumes. However, in some applications, it may be advantageous to use a diluent. Such diluent may improve the mixing and mass transfer of the olefin into the aqueous catalyst solution, or provide improved recovery of the carbonyl product by improved liquid-liquid phase distribution, and/or improved phase separation. In other applications, the olefinic feed may be obtained in combination with substantially inert diluents which are more easily or economically separated from the carbonyl product than from the olefin. For example, butenes may be obtained in combination with butane, cyclohexene may be obtained in combination with cyclohexane and/or benzene. In other applications, it may be desirable to use a cosolvent diluent which miscibilizes the olefinic and aqueous solution components.

Suitable reactors for the processes of the invention provide for efficient mixing of olefinic and aqueous catalyst phases. Efficient mixing in the olefin reaction is established when the rate of the reaction is governed by the chemical kinetics of catalysis, and is not limited by diffusion of the olefin into the aqueous phase. Once that condition is established, dissolved olefin concentration in the aqueous solution can be increased by increasing the olefin concentration in the olefinic phase (for gaseous olefins, by increasing the partial pressure of the olefin). In some embodiments, the olefin concentration in the aqueous solution is effective for the olefin oxidation rate to become independent of the olefin concentration in the aqueous solution (olefin saturation kinetics). Efficient mixing in the dioxygen reaction is established when the diffusion-limited dioxygen reaction rate proceeds rapidly enough for convenient and economical utilization in the intended application, preferably at least 1 (millimole dioxygen/liter solution)/second.

Reactors and associated equipment in contact with the aqueous catalyst solution should withstand the oxidizing nature of the solution and processes without corrosion. For solutions and processes in the absence of chloride, stainless steel, Hastelloy C, glass, and titanium provide suitable equipment surfaces. For solutions and processes in the presence of chloride, titanium and/or glass is preferred.

The carbonyl product of the reaction may be separated from the reaction solution by usual methods such as vaporizing ("flashing" by pressure drop), stripping, distilling, phase separation, extraction, and the like. It is preferred that the carbonyl product is recovered while leaving the aqueous solution in a form suitable to use directly in continued process operation. In two-stage operation, it is preferred to remove the product before the dioxygen reaction. In one-stage operation for a volatile carbonyl product, it is preferred to continuously remove the product as it is formed in the process.

Processes for the oxidation of palladium (0) to palladium (II) require only that the palladium (0) is contacted with the polyoxoanion oxidant solution under conditions sufficient to oxidize palladium (0) to palladium (II) at the desired rate. Temperature, chloride ion concentration, and palladium (0) surface area are particularly interdependent in determining such conditions. Generally, the greater the chloride ion concentrations, the lower the temperature required to achieve a desired rate. If the dissolved palladium (II) is to be used in an olefin oxidation process, the conditions are generally similar to those of the olefin oxidation process.

Solutions and Processes wherein the hydrogen ion concentration is greater than 0.1 mole/liter:

Solutions and related processes of the present invention wherein the hydrogen ion concentration is greater than 0.1 mole/liter need not be essentially free of sulfate, nor further comprise chloride ions, nor further comprise any minimum dissolved olefin concentration. However, preferred embodiments of such solutions and processes may include one or more of these features.

Solutions and Processes essentially free of sulfate:

Solutions and related processes of the present invention which are essentially free of sulfate ions need not also comprise a hydrogen ion concentration greater than 0.1 mole/liter, nor further comprise chloride ions, nor further comprise any minimum dissolved olefin concentration. However, preferred embodiments of such solutions and processes may include one or more of these features. In particular, it is preferred that the hydrogen ion concentration of the solution be at least greater than $10^{-3}$ moles/liter.

Solutions and Processes comprising Chloride:

Solutions and related processes of the present invention using those solutions which comprise chloride ions need not also comprise a hydrogen ion concentration greater than 0.1 mole/liter, nor also be essentially free of sulfate, nor further comprise any minimum dissolved olefin concentration. However, preferred embodiments of such solutions and processes may use one or more of these features. In particular, it is preferred that the hydrogen ion concentration of the solution be at least greater than $10^{-3}$ moles/liter.

It is especially preferred that solutions and processes which do not provide effective concentrations of dissolved olefin, do comprise chloride ions.

Solutions and Processes comprising dissolved olefin at effective concentrations:

Solutions and related processes of the present invention which comprise certain effective dissolved olefin concentrations in the aqueous catalyst solution, and processes which comprise certain effective mixing conditions need not also comprise a hydrogen ion concentration greater than 0.1 mole/liter, nor be essentially free of sulfate, nor further comprise chloride ions. However, preferred embodiments of such solutions and processes include one or more of these features. In particular, it is preferred that the hydrogen ion concentration of the solution be at least greater than $10^{-3}$ moles/liter.

EXAMPLES

Figure 1:
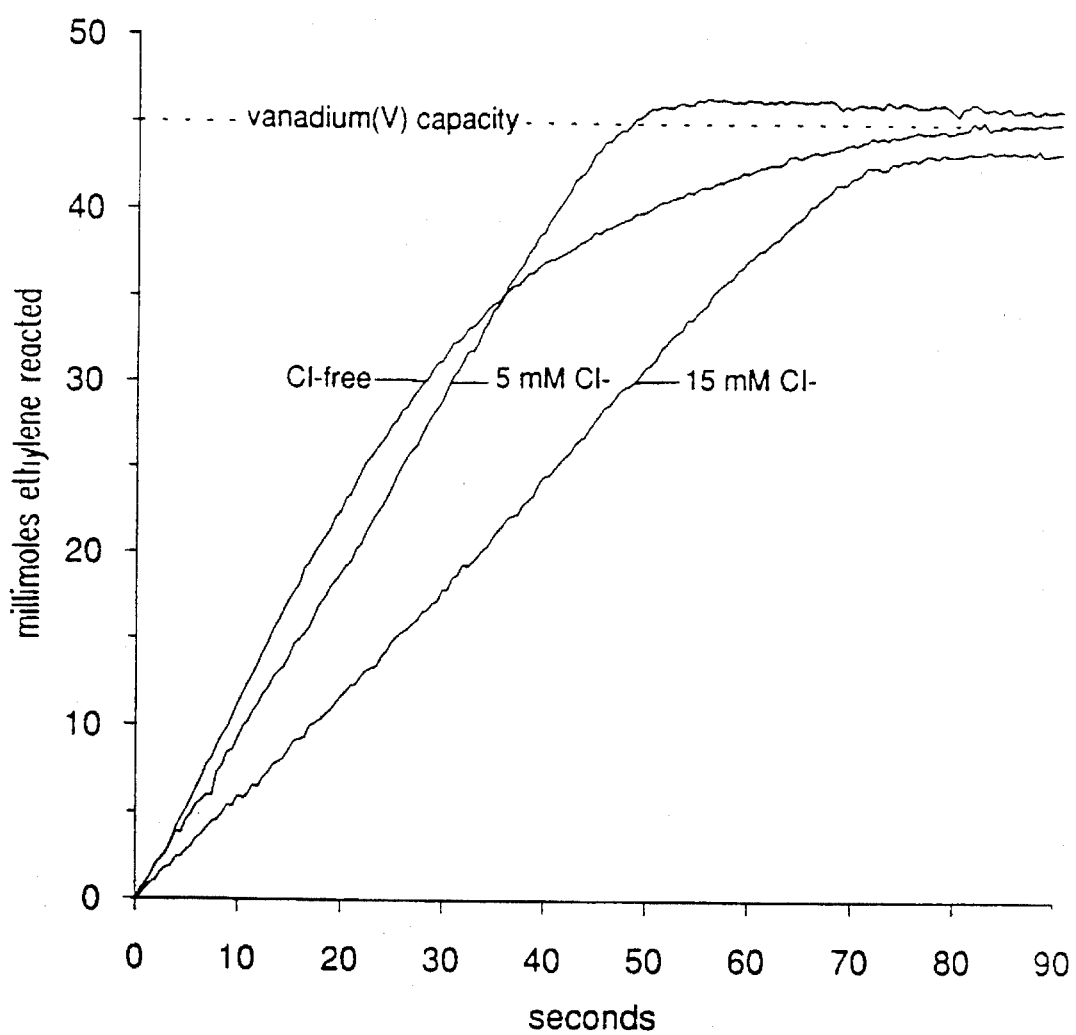
FIG. 1 is an overlay plot of ethylene consumptions vs. time in palladium catalyzed ethylene oxidations by 0.30M $\{Li_3H_3PMo_9V_3O_{40}\}$ solutions containing various concentrations of chloride ions. The plotted reactions are further described at Examples 25, 32, and 34 (Table 2).

Without further elaboration, it is believed that one skilled in the art can, using the preceding description, utilize the present invention to its fullest extent. The following specific examples are, therefore, intended to be merely illustrative, and not limitative of the disclosure in any way whatsoever. Further exemplification is provided in co-filed U.S. patent applications Ser. Nos. 07/689,050, 07/689,048, and 07/675, 937, each of which is incorporated by reference entirely.

Every $-\log[H^+]$ value recited in these examples and in the drawings is the base 10 logarithm of the hydrogen ion concentration in units of mole/liter. Thus, $-\log[H^+]=1.0$ corresponds to a hydrogen ion concentration of 0.10 mole/liter, and a $-\log[H^+]<1.0$ corresponds to a hydrogen ion concentration greater than 0.10 mole/liter Preparations of Polyoxoanion Solutions:

Examples 1 through 8 and 10 through 22 show preparations of solutions of polyoxoanions within the scope of the invention which are useful in the inventive catalyst solutions and processes. Except when otherwise stated, the exemplified polyoxoanion syntheses used $H_3PO_4$ (food grade), $MoO_3$ (pure molybdic oxide), and $V_2O_5$ (chemical grade) and were conducted in a 3 neck Morton flask, of 5.0 liter or 12.0 liter capacity, equipped with an electric heating mantle, an efficient reflux condenser/demister, a powder addition funnel and a high torque overhead mechanical stirrer. Distilled water rinses were used for every solution transfer in the preparations to ensure essentially quantitative recovery of dissolved solution components in the final solution.

EXAMPLE 1

Preparation of 0.30M $\{H_4PMo_{11}VO_{40}\}$: An aqueous solution of the phosphomolybdovanadic free acid $H_4PMo_{11}VO_{40}$ was prepared according to the following reaction equation:

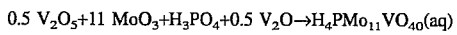

$$0.5\ V_2O_5+11\ MoO_3+H_3PO_4+0.5\ V_2O \rightarrow H_4PMo_{11}VO_{40}(aq)$$

45.47 grams granular $V_2O_5$ (0.25 mole) and 791.67 grams $MoO_3$ (5.50 mole) were suspended in 5.0 liters distilled water with moderate stirring. 57.37 grams 85.4% (w/w) $H_3PO_4$ (0.05 mole) was added, the mixture was diluted to a total volume of 10.0 liters with an additional 4.5 liters of distilled water, and the mixture was heated to reflux. After 2 days at reflux, 15 drops of 30% $H_2O_2$ was added dropwise to the mixture. The mixture was maintained at reflux for a total of 7 days, giving a slightly turbid light burgundy-red mixture. The mixture was cooled to room temperature and clarified by vacuum filtration. The volume of the solution was reduced to about 1.5 liters by rotating-film evaporation at 50° C. under vacuum. The resulting homogenous, clear, burgundy-red solution was volumetrically diluted with distilled water to a total volume of 1.667 liters, giving 0.30 molar $H_4PMo_{11}VO_{40}$.

$H_4PMo_{11}VO_{40}$ is a very strong acid whose four acidic hydrogens are completely dissociated from the polyoxoanion as hydrogen ions in this solution. The hydrogen ion concentration of this solution is explicitly 1.2 mole/liter; $-\log[H^+]=-0.08$

EXAMPLE 2

Preparation of 0.30M $\{Na_4PMo_{11}VO_{40}\}$: An aqueous solution of the phosphomolybdovanadate full salt $Na_4PMo_{11}VO_{40}$ was prepared according to the following reaction equations:

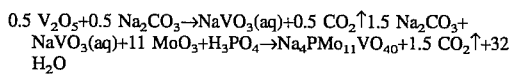

$$0.5\ V_2O_5+0.5\ Na_2CO_3 \rightarrow NaVO_3(aq)+0.5\ CO_2\uparrow 1.5\ Na_2CO_3+ NaVO_3(aq)+11\ MoO_3+H_3PO_4 \rightarrow Na_4PMo_{11}VO_{40}+1.5\ CO_2\uparrow+32\ H_2O$$

109.13 grams granular $V_2O_5$ (0.60 mole) was suspended in 1.0 liter distilled water in a Morton flask with overhead stirring. The mixture was heated to ca. 60° C. and 63.59 grams, granular $Na_2CO_3$ (0.60 mole) was slowly added in portions to the rapidly stirred suspension, causing $CO_2$ liberation and dissolution of the $V_2O_5$ to give an essentially homogeneous solution. The solution was heated at reflux for 60 minutes. Approximately 1 ml of 30% $H_2O_2$ was added dropwise to the mixture, which was maintained at reflux for an additional 60 minutes, then cooled to room temperature. The solution was clarified by vacuum filtration, and the resulting clear, orange sodium vanadate solution was then returned to a Morton flask with additional distilled water. 1900.01 grams $MoO_3$ (13.2 mole) was added with rapid stirring, the mixture was heated to about 60° C., and 190.78 grams granular $Na_2CO_3$ (1.80 mole) was slowly added in portions to the rapidly stirred suspension, causing $CO_2$ liberation and dissolution of $MoO_3$. 137.70 grams 85.4% (w/w) $H_3PO_4$ (1.20 mole) was then slowly added to the mixture, and the mixture was heated at the reflux and thereby converted to a clear, dark, burgundy-brown solution. After 3 hours at reflux, the homogenous solution was cooled to room temperature and volumetrically diluted with distilled water to a total volume of 4.0 liters, giving 0.30 molar $\{Na_4PMo_{11}VO_{40}\}$.

EXAMPLE 3

Preparation of 0.30M $\{Li_4PMo_{11}VO_{40}\}$: The procedure was the same as for $\{Na_4PMo_{11}VO_{40}\}$ in Example 2 except that 133.00 grams granular $Li_2CO_3$ (1.80 mole) was substituted for the $Na_2CO_3$.

These solutions of 0.30M $\{A_4PMo_{11}VO_{40}\}$, A=Na, Li, were found to be reproducibly slightly acidic, having hydrogen ion concentrations ~0.001M. Presumably, a minute fraction of the Keggin polyoxoanion is hydrolytically dissociated, with release of hydrogen ions from water, at equilibrium. 162 MHz $^{31}$P-NMR and 105 MHz $^{51}$V- NMR spectra of these solutions were essentially identical to those of 0.30M $\{H_4PMo_{11}VO_{40}\}$, showing substantially only the $PMo_{11}VO_{40}^{4-}$ ion.

EXAMPLES 4–8

Preparations of 0.30M $\{A_pH_{(4-p)}PMo_{11}VO_{40}\}$, A=Na, Li; The following 0.30M $\{A_pH_{(4-p)}PMo_{11}VO_{40}\}$ solutions were prepared by blending 0.30M $\{H_4PMo_{11}VO_{40}\}$ (Example 1) and 0.30M $\{A_4PMo_{11}VO_{40}\}$, A=Na (Example 2) or Li (Example 3) in (4-p):p volumetric ratios. The hydrogen ion concentration in each of these solutions is explicitly 0.30 (4-p) mole/liter, as indicated:

| Example 4: | 0.30M $\{Na_{0.67}H_{3.33}PMo_{11}VO_{40}\}$ | $-\log[H+] = 0.00$ |
| Example 5: | 0.30M $\{Na_{3.67}H_{0.33}PMo_{11}VO_{40}\}$ | $-\log[H+] = 1.00$ |
| Example 6: | 0.30M $\{Li_{0.67}H_{3.33}PMo_{11}VO_{40}\}$ | $-\log[H+] = 0.00$ |
| Example 7: | 0.30M $\{Li_{3.67}H_{0.33}PMo_{11}VO_{40}\}$ | $-\log[H+] = 1.00$ |
| Example 8: | 0.30M $\{Li_{2.67}H_{1.33}PMo_{11}VO_{40}\}$ | $-\log[H+] = 0.40$ |

Each of these solutions is alternatively prepared by adding the appropriate amount of the alkali (Na, Li) carbonate, bicarbonate or hydroxide to the $\{H_4PMo_{11}VO_{40}\}$ solution or to a $\{A_pH_{(4-p)}PMo_{11}VO_{40}\}$ solution of lesser p.

The following Example shows a method for measurement of the hydrogen ion concentration in acidic aqueous polyoxoanion solutions and corresponding catalyst solutions, which is particularly preferred for determining hydrogen ion concentrations in such solutions having hydrogen ion concentrations greater than 0.10 mole/liter. The described procedures were used to determine all of the hydrogen ion concentrations recited in the present examples and in the drawings, usually expressed as $-\log[H^+]$. These recited hydrogen ion concentrations were measured with the indicated polyoxoanions in solution in their oxidized state.

EXAMPLE 9

Measurement of Hydrogen Ion Concentration: $-\log[H^+]$ measurements were made with a commercial glass combination pH electrode ((Orion) Ross Combination pH electrode) and commercial digital-display pH potentiometer (Corning, Model 103, portable pH meter). In pH display mode, the potentiometer was calibrated to display 1.00 with the electrode in 0.30M $\{Na_{3.67}H_{0.33}PMo_{11}VO_{40}\}$ (Example 5) and 0.00 in 0.30M $\{Na_{0.67}H_{3.33}PMo_{11}VO_{40}\}$ (Example 4), without intermediate adjustment. This calibration was used to measure $-\log[H^+]$ in 0.30M $\{Na_pH_{(3+n-p)}PMo_{(12-n)}V_nO_{40}\}$ solutions with $p \geq 0$ having $-\log[H^+] \leq 1.00$.

To measure $-\log[H^+]$ in 0.30M $\{aNa_pH_{(3+n-p)}PMo_{(12-n)}V_nO_{40}\}$ solutions having $-\log[H^+]>1.00$, the potentiometer was instead calibrated with the 0.30M $\{Na_{3.67}H_{0.33}PMo_{11}V_1O_{40}\}$ solution, $-\log[H^+]=1.00$, and 0.10M $Na_{1.6}H_{1.6}H_{1.4}PO_4$ pH 7.0 buffer (prepared from $Na_2HPO_4 \cdot 7H_2O$ and $NaH_2PO_4 \cdot H_2O$ in distilled water), taken to be $-\log[H^+]=7.0$. (pH 7 is far from the hydrogen ion concentrations in the so measured polyoxoanion solutions, so that any discrepancy between pH and $-\log[H^+]$ in this calibration solution only insignificantly effects the accuracy of those measurements.)

To measure $-\log[H^+]$ in 0.30M $\{Li_pH_{(3+n-p)}PMo_{(12-n)}V_nO_{40}\}$ solutions with p>0, the corresponding $Li^+$ calibration solutions were used: 0.30M $\{Li_{0.67}H_{3.33}PMo_{11}VO_{40}\}$, $-\log[H^+]=0.00$ (Example 6); 0.30M $\{Li_{3.67}H_{0.33}PMo_{11}VO_{40}\}$, $-\log[H^+]=1.00$ (Example 7); and 0.10M $Li_{1.6}H_{1.4}PO_4$ (prepared from $H_3PO_4$ and LiOH in distilled water), taken to be $-\log[H^+]=7$. By this calibration, 0.30M $\{Li_{2.67}H_{1.33}PMo_{11}VO_{40}\}$ (Example 8), with known $-\log[H^+]=0.40$, was measured to be $-\log[H^+]=0.37$, indicating the accuracy of the measurement.

To measure $-\log[H^+]$ in solutions having other Keggin polyoxoanion concentrations, calibration solutions of $\{A_pH_{(4-p)}PMo_{11}VO_{40}\}$ at the same other polyoxoanion concentration are used: $-\log[H^+]$ for X M $\{A_pH_{(4-p)}PMo_{11}VO_{40}\}$ is X(4-p).

Although hydrogen ion concentrations were quantitatively measured for the polyoxoanion and catalyst solutions in the present Examples, it is often sufficient to simply discriminate qualitatively whether the hydrogen ion concentration is greater than or less than 0.10 mole/liter. A single calibration solution of $\{A_pH_{(4-p)}PMo_{11}VO_{40}\}$ with a hydrogen ion concentration of 0.10 mole/liter can be used to determine if another polyoxoanion solution has a hydrogen ion concentration greater than or less than 1.10 mole/liter by comparison. Preferably, the calibration solution has the same polyoxoanion concentration and the same salt countercation as the other solution in question. Any physical measurement technique capable of discriminating between solutions having hydrogen ion concentrations greater than or less such a single calibration solution is suitable for making the comparison.

Example 10

Preparation of 0.30M$\{Na_2H_3PMo_{10}V_2O_{40}\}$: An aqueous phosphomolybdovanadic acid partial salt solution designated 0.30M $\{Na_2H_3PMo_{10}V_2O_{40}\}$ was prepared according to the following reaction equations:

$$V_2O_5+Na_2CO_3 \rightarrow 2NaVO_3(aq)+CO_2\uparrow 2NaVO_3(aq)+10MoO_3+ \\ H_3PO_4 \rightarrow Na_2H_3PMo_{10}V_2O_{40}(aq)$$

218.26 grams granular $V_2O_5$ (1.20 mole) was suspended in 2.0 liters distilled water in a Morton flask with overhead stirring and the mixture was heated to about 60° C. 127.19 grams granular $Na_2CO_3$ (1.20 mole) was slowly added in portion to the rapidly stirred mixture, causing $CO_2$ liberation and dissolution of the $V_2O_5$ to give and essentially homogeneous solution. The solution was heated at the reflux for 60 minutes. The solution was then lime green color due to dissolved $V^{IV}$ which was originally present in the $V_2O_5$. Approximately 1 ml of 30% $H_2O_2$ was added dropwise to the mixture causing the dark, black-blue green color to fade, leaving a slightly turbid, pale-tan sodium vanadate solution. The solution was maintained at reflux for an additional 60 minutes to ensure the decomposition of excess peroxide and then cooled to room temperature. The solution was clarified by vacuum filtration to remove the small amount (>0.1 grams) of brown solid which contained almost all the iron and silica impurities originally present in the $V_2O_5$. The clear, orange sodium vanadate solution was then returned to a Morton flask, and 1727.28 grams $MoO_3$ (12.00 mole) was added with rapid overhead stirring. The mixture was heated to about 60° C. and 137.7 grams 85.4% (w/w) $H_3PO_4$ (1.20 mole) was added. The mixture was heated at the reflux and thereby converted to a clear, dark, burgundy-red solution. After 3 hours at reflux, the homogenous burgundy-red solution was cooled to room temperature and volumetrically diluted with distilled water to a total volume of 4.00 liters, giving 0.30M{$Na_2H_3PMo_{10}V_2O_{40}$}.

The hydrogen ion concentration of 0.30M {$Na_2H_3PMo_{10}V_2O_{40}$} was measured to be 0.67 mole/liter; $-\log[H^+]=0.18$.

EXAMPLE 11

Preparation of 0.30M {$Na_5PMo_{10}V_2O_{40}$}: An aqueous phosphomolybdovanadate full salt solution designated 0.30M {$Na_5PMo_{10}V_2O_{40}$} was prepared according to the following reaction equations:

$$V_2O_5+Na_2CO_3 \rightarrow 2NaVO_3(aq)+CO_2\uparrow 1.5Na_2CO_3+2NaVO_3(aq)+ \\ 10MoO_3+H_3PO_4 \rightarrow Na_5PMo_{10}V_2O_{40}+1.5CO_2\uparrow +1.5H_2O$$

The procedure was the same as in Example 10 except that after the addition of the $MoO_3$, the mixture was heated to the reflux and an additional 190.78 grams granular $Na_2CO_3$ (1.80 mole) was slowly added in portions to the stirred suspension, causing $CO_2$ liberation, before the addition of the $H_3PO_4$.

EXAMPLES 12–16

Preparations of 0.30M {$Na_pH_{(5-p)}PMo_{10}V_2O_{40}$} solutions: The following polyoxoacid partial salt solutions designated 0.30M {$Na_pH_{(5-p)}PMo_{10}V_2O_{40}$} were prepared by blending 0.30M {$Na_2H_3PMo_{10}V_2O_{40}$} (Example 10) and 0.30M {$Na_5PMo_{10}V_2O_{40}$} (Example 11) in (5-p):(p-2) volumetric ratios, and their hydrogen ion concentrations were measured as indicated:

| Example 12 | 0.30M {$Na_4HPMo_{10}V_2O_{40}$} | $-\log[H+] = 0.69$ |
| Example 13 | 0.30M {$Na_{4.40}H_{0.60}PMo_{10}V_2O_{40}$} | $-\log[H+] = 0.91$ |
| Example 14 | 0.30M {$Na_{4.47}H_{0.53}PMo_{10}V_2O_{40}$} | $-\log[H+] = 1.00$ |
| Example 15 | 0.30M {$Na_{4.80}H_{0.20}PMo_{10}V_2O_{40}$} | $-\log[H+] = 1.43$ |
| Example 16 | 0.30M {$Na_{4.94}H_{0.06}PMo_{10}V_2O_{40}$} | $-\log[H+] = 1.96$ |

Each of these solutions is alternatively prepared by adding the appropriate amount of the sodium carbonate, bicarbonate or hydroxide to a 0.30M {$Na_pH_{(5-p)}PMo_{10}V_2O_{40}$} solution of lesser p.

EXAMPLE 17

Preparation of 0.30M {$Na_3H_3PMo_9V_3O_{40}$}: The phosphomolybdovanadic partial salt solution designated {$Na_3H_3PMo_9V_3O_{40}$} was prepared according to the following reaction equations:

$$1.5V_2O_5+1.5Na_2CO_3 \rightarrow 3NaVO_3(aq)+1.5CO_2\uparrow 3NaVO_3(aq)+9 \\ MoO_3+H_3PO_4 \rightarrow Na_3H_3PMo_9V_3O_{40}(aq)$$

818.46 grams granular $V_2O_5$ (4.50 moles) was suspended in 3.5 liters distilled water in a Morton flask with overhead stirring and the mixture was heated to about 60° C. 476.95 grams granular $Na_2CO_3$ (4.50 moles) was slowly added in portions to the rapidly stirred mixture, causing $CO_2$ liberation and dissolution of the $V_2O_5$ to give and essentially homogeneous solution. The solution was heated at the reflux for 60 minutes. The solution was then dark, blue-green due to dissolved $V^{IV}$ which was originally present in the $V_2O_5$. Approximately 1 ml of 30% $H_2O_2$ was added dropwise to the mixture causing the dark, black-blue green color to fade, leaving a slightly turbid, pale-tan sodium vanadate solution. The solution was maintained at reflux for an additional 60 minutes to ensure the decomposition of excess peroxide and then cooled to room temperature. The solution was clarified by vacuum filtration to remove the small amount (<0.2 grams) of brown solid which contained almost all the iron and silica impurities originally present in the $V_2O_5$. The clear, orange sodium vanadate solution was then returned to a Morton flask, diluted with 4.0 liters distilled water, and 3886.38 grams $MoO_3$ (27.00 moles) was added with rapid overhead stirring. The mixture was heated to about 60° C. and 344.25 grams 85.4% (w/w) $H_3PO_4$ (3.00 moles) was added. The mixture was heated at the reflux and thereby converted to a clear, dark, burgundy-red solution. After 3 hours at reflux, the homogenous solution was cooled to room temperature and volumetrically diluted with distilled water to a total volume of 10.00 liters, giving 0.30M {$Na_3H_3PMo_9V_3O_{40}$}. The hydrogen ion concentration of 0.30M {$Na_3H_3PMo_9V_3O_{40}$} was measured to be 0.35 mole/liter; $-\log[H^+]=0.45$

EXAMPLE 18

Preparation of 0.30M {$Na_5HPMo_9V_3O_{40}$}; This solution was prepared by neutralization of 0.30M {$Na_3H_3PMo_9V_3O_{40}$} with $Na_2CO_3$ as follows:

15.90 grams granular $Na_2CO_3$ (0.15 mole) was slowly added to 0.500 liter 0.30M {$Na_3H_3PMo_9V_3O_{40}$} (0.15 mole) with rapid stirring. The resulting solution was heated to the boil for 1.5 hours (with loss of water volume), cooled to room temperature, and volumetrically diluted with distilled water to 0.500 liter. The resulting 0.30M {$Na_5HPMo_9V_3O_{40}$} had $-\log [H^+]=1.96$.

EXAMPLES 19 and 20

Preparations of 0.30M {$Na_pH_{(6-p)}PMo_9V_3O_{40}$} solutions: The following polyoxoacid partial salt solutions designated 0.30M {$Na_pH_{(6-p)}PMo_9V_3O_{40}$} were prepared by blending 0.30M {$Na_3H_3PMo_9V_3O_{40}$} (Example 17) and 0.30M {$Na_5HPMo_9V_3O_{40}$} (Example 18) in (5-p):(P-3) volumetric ratios, and their hydrogen ion concentrations were measured as indicated:

| | | |
|---|---|---|
| Example 19 | 0.30M $\{Na_{4.2}H_{1.8}PMo_9V_3O_{40}\}$ | $-\log[H+] = 1.00$ |
| Example 20 | 0.30M $\{Na_{4.7}H_{1.3}PMo_9V_3O_{40}\}$ | $-\log[H+] = 1.41$ |

EXAMPLE 21

Preparation of 0.30M $\{Li_3H_3PMo_9V_3O_{40}\}$: The procedure was the same as for 0.30M $\{Na_3H_3PMo_9V_3O_{40}\}$ in Example 17 except that 332.51 grams granular $Li_2CO_3$ (4.50 moles) was substituted for the $Na_2CO_3$. The hydrogen ion concentration of the solution was measured as $-\log[H^{3O}]= 0.38$

EXAMPLE 22

Preparations of 0.30M $\{Na_3H_3PMo_9V_3O_{40}\}$ solutions from solid $NaVO_3$; Solutions of 0.30M $\{Na_3H_3PMo_9V_3O_{40}\}$ were prepared according to the second reaction equation under Example 17, starting with solid sodium metavanadate, as follows.

219.5 grams $NaVO_3$ (1.80 Moles) was pulverized and added to 0.40 liters distilled water in an Erlenmayer flask and the mixture was stirred and heated until all the $NaVO_3$ dissolved. The solution was then cooled to room temperature and clarified by vacuum filtration using distilled water rinses to ensure quantitative recovery of the dissolved sodium vanadate in the filtrate. The pale green-yellow solution was transferred to a Morton flask with distilled water added to a total volume of about 2.0 liters. 777.38 grams $MoO_3$ (5.40 moles) was added with rapid overhead stirring. The mixture was heated to about 60° C. and 68.855 grams 84.5% (w/w) $H_3PO_4$ (0.60 moles) was added. The mixture was heated at the reflux and thereby converted to a clear, dark, burgundy-red solution. After about 3 hours at reflux, the homogenous solution was cooled to room temperature and its volume was volumetrically adjusted to 2.00 liters, giving 0.30M $\{Na_3H_3PMo_9V_3O_{40}\}$.

Four 0.30M $\{Na_3H_3PMo_9V_3O_{40}\}$ solutions were prepared in this manner from three different commercial sources of $NaVO_3$ and two different commercial sources of $MoO_3$, one of which was the same as used in Example 17. (The source of $H_3PO_4$ was the same in all these Examples.)

EXAMPLE 23

Measurements of chloride ion concentrations in polyoxoanion solutions prepared from different source material; Chloride ion concentration analyses were made on each of six 0.30m $\{Na_3H_3PMo_9V_3O_{40}\}$ solutions prepared from a matrix of commercial starting materials. Four of the solutions were the ones prepared in Example 22 from three commercial $NaVO_3$ sources and two commercial $MoO_3$ sources. The other two solutions were prepared from the same two commercial $MoO_3$ sources and commercial $V_2O_5$ (via $NaVO_3$(aq) solution) in the manner of Example 17.

Chloride ion concentrations were analyzed by AgCl-precipitating potentiometric titration with 1.00 mN $AgNO_3$ using a commercial chloride ion specific electrode (Orion) and a commercial titroprocessor (Brinkman 686). The analyses were calibrated by titration of precisely weighed 1.5 to 3.0 gram samples of 51.0 ppm (2.01 mM) and 102.0 ppm (4.03 mM) aqueous chloride standards, diluted to about 40 ml with distilled water prior to titration. The accurate detection threshold was estimated to be about 0.1 mM chloride. Precisely weighed samples of six 0.30M $\{Na_3H_3PMo_9V_3O_{40}\}$ solutions, about 2.0 grams each (density=1.40 g/ml) were diluted to about 40 ml with distilled water and titrated.

The two solutions prepared from $V_2O_5$ showed no detectable chloride when titrated in this manner. They also showed no detectable chloride when undiluted 30 grams samples were titrated. This indicates that the $V_2O_5$ source and the two commercial $MoO_3$ sources introduced no more than insignificant amounts of chloride into these polyoxoanion solutions. (Solutions labeled "chloride-free" throughout the Examples herein were prepared from these starting materials.) Solutions prepared from the two commercial $MoO_3$ sources and the same commercial $NaVO_3$ source analyzed for essentially the same concentration of chloride, again indicating that the two $MoO_3$ sources did not introduce significant concentrations of chloride.

Solutions prepared from the three commercial $NaVO_3$ sources analyzed for 3.0, 8.8, and 3.7 millimolar concentrations of chloride. $NaVO_3$ is typically produced by dissolving $V_2O_5$ in water with sodium hydroxide, bicarbonate, or carbonate in water, and evaporating the water. We speculate that chlorinated municipal water was used in the production of these $NaVO_3$ sources, and that chloride was concentrated into the $NaVO_3$ product when the water was evaporated.

This example demonstrates that chloride ions in the inventive solutions and related processes may be provided as an impurity in a starting material used to prepare the polyoxoanion oxidant.

Ethylene reactions:

Examples 24 through 61 show catalyst solutions and olefin-catalyst solution mixtures within the scope of the invention and their use in processes for oxidation of an olefin to a carbonyl product within the scope of this invention, specifically exemplifying processes for oxidation of ethylene to acetaldehyde. In each of these examples, a palladium catalyst solution was prepared by the addition of the indicated palladium salt, as well as any other indicated solution components, to the indicated polyoxoanion oxidant solution. The hydrogen ion concentration of each of the exemplified catalyst solutions was the same as that of its parent polyoxoanion solution, as recited among the preceding Examples.

The illustrated ethylene reactions were conducted in similarly equipped stirred tank autoclave reactors having 300 ml internal volume and fabricated of 316 stainless steel (Reactor #1), Hastelloy C (Reactor 190 2), or titanium (Reactor #3). Each autoclave was equipped with a hollow shaft stirring impeller fitted with a six bladed flat disk turbine, coaxial with the cylindrical internal autoclave volume. The hollow shaft had a hole high in internal volume for gas inlet and another at the impeller turbine for efficient dispersion of the gas phase through the liquid phase. The stirring impeller was magnetically coupled to magnets belted to a rheostated direct current electric motor. Each autoclave was fitted with a vertical baffle which extended along the internal wall through the unstirred gas-liquid interface. Resistive electric heating elements were jacketed to each autoclave body and were controlled by a proportioning controller which monitored the liquid solution temperature via a thermocouple. Volumetrically calibrated reservoirs for gas delivery were connected to each autoclave via feed-forward pressure regulators.

The ethylene reactions were conducted in fed-batch mode, with a batch of catalyst solution and a continuous regulated feed of ethylene from higher pressure in the reservoir into the autoclave to maintain the set autoclave pressure. Thermocouples and pressure transducers monitored the temperatures and pressures of the reaction mixture in the autoclave and the ethylene in the reservoir, and a magnetic-sensing tachometer monitored the impeller revolution rate. These transducers were all interfaced to a computer system for continuous data acquisition as a function of time. Reservoir volume, pressure, and temperature data were converted to moles of ethylene in the reservoir using a non-ideal gas equation incorporating the compressibility of ethylene.

For each exemplified ethylene reaction, 100 milliliters of the indicated catalyst solution was charged to the autoclave and the gas phase in the autoclave was changed to 1 atmosphere dinitrogen. The sealed autoclave was heated to bring the stirring solution to the indicated reaction temperature and the autogenic pressure at this temperature was noted. With very gentle stirring of the solution, ethylene was regulated into the autoclave to give a total autoclave pressure equal to the autogenic pressure plus the indicated ethylene partial pressure. (With only very gentle stirring of the liquid phase, gas-liquid mixing is almost nil and the ethylene reaction is so severely diffusion limited that no detectable reaction occurs. Gentle stirring, rather than no stirring, was provided to avoid thermal gradients in the solution.) With the autoclave open to the forward regulated total pressure from the reservoir, the reaction was initiated by increasing the impeller stirring rate to provide efficient dispersion of the gas through the liquid phase. The increase in stirring rate occurred virtually instantaneously relative to the time scale of the ensuing reaction. The reaction proceeded under constant pressure while reservoir temperature and pressure data was collected. The decrease in moles of ethylene in the reservoir was taken to correspond to the moles of ethylene reacted.

For every exemplified ethylene reaction for which the acetaldehyde product in the solution was quantitatively analyzed (by standard gas-liquid phase chromatography procedures), the reaction selectivity to acetaldehyde was $\geq 90\%$, typically $\geq 95\%$, and often $\geq 98\%$. Major by-products were acetic acid and crotonaldehyde, which are secondary products of acetaldehyde, by oxidation and condensation, respectively. The amounts of these by-products increased and the amount of acetaldehyde decreased with the amount of time the acetaldehyde-containing catalyst solution spent at reaction temperature and subsequently at room temperature after the reaction of ethylene to acetaldehyde reached completion.

Statistically significant modest differences in ethylene reaction rates were measured among the three different reactors for otherwise nominally equivalent reactions. There differences were never more than 25%, usually less, and are attributed to differences in the accuracies of the temperature and ethylene pressure controls among the reactors. All recited comparisons of results among the following Examples are drawn from reactions conducted in the same reactor.

Volumetric ethylene reaction rate is reported as (millimole ethylene liter solution)/second, abbreviated mmol $l^{-1}$ $s^{-1}$. Palladium turnover frequency, TF, is reported as (moles ethylene/mole palladium)/second, abbreviated $s^{-1}$, which is the volumetric ethylene reaction rate divided by the palladium concentration. Ethylene conversion expressed as % theory refers to the % utilization of the vanadium (V) capacity of the solution according to reaction (12); it is 100(moles ethylene reacted)/(moles vanadium(V)/2). The palladium turnover number, TON, is (total moles ethylene reacted/moles palladium).

All the ethylene reaction described in the following Examples were conducted under gas-liquid mixing conditions sufficient for the ethylene reaction rate to not be limited by ethylene dissolution (mass transfer) into the palladium catalyst solution. The reaction rates instead manifested chemical kinetics which were dependent on the palladium (ll) catalyst activity and proportional to its concentration.

EXAMPLES 24–42

Oxidation of ethylene with 0.30M $\{Li_3H_3PMo_9V_3O_{40}\}$ having various chloride concentrations; In each of these examples, a palladium catalyst solution was prepared by dissolving a palladium salt in 0.30M $\{Li_3H_3PMo_9V_3O_{40}\}$ and, in some examples, also adding LiCl or HCl, as indicated in Table 2. 100 milliliters of each catalyst solution was reacted at 120° C. with ethylene at 150 psi partial pressure in Reactor #2 using an impeller stirring rate of about 2000 RPM, usually until ethylene comsumption ceased. Table 2 lists the palladium salt and its millimolar concentration, the added chloride source and its millimolar concentration, the total chloride concentration in the solution, the initial ethylene reaction rate and palladium turnover frequency, and the ethylene consumption in millimoles and as a percent of the theoretical vanadium (V) oxidizing equivalents in the solution.

TABLE 2

| Ex. No. | palladium(II) salt source | mM | added chloride source | mM | total chloride mM | rate mmol $l \cdot s$ | Pd TF $s^{-1}$ | $C_2H_4$ reacted mmol | % theory |
|---|---|---|---|---|---|---|---|---|---|
| 24 | Pd(CH$_3$CO$_2$)$_2$ | 0.10 | none | | 0 | 11.8 | 118 | 45.6 | 101 |
| 25 | Pd(CH$_3$CO$_2$)$_2$ | 0.10 | none | | 0 | 11.9 | 119 | 46.1 | 102 |
| 26 | Pd(CH$_3$CO$_2$)$_2$ | 0.10 | none | | 0 | 11.4 | 114 | 45.0 | 100 |
| 27 | Pd(CH$_3$CO$_2$)$_2$ | 0.10 | none | | 0 | 11.3 | 113 | 44.9 | 100 |
| 28 | PdCl$_2$ | 0.10 | none | | 0.20 | 12.3 | 123 | 44.0 | 98 |
| 29 | Pd(CH$_3$CO$_2$)$_2$ | 0.10 | LiCl | 0.20 | 0.20 | 11.5 | 115 | 43.7 | 97 |
| 30 | Pd(CH$_3$CO$_2$)$_2$ | 0.10 | LiCl | 1.00 | 1.00 | 12.4 | 124 | 41.9 | 93 |
| 31 | Pd(CH$_3$CO$_2$)$_2$ | 0.10 | LiCl | 5.00 | 5.00 | 9.7 | 97 | 43.0 | 96 |
| 32 | Pd(CH$_3$CO$_2$)$_2$ | 0.10 | HCl | 5.40 | 5.40 | 9.5 | 95 | 46.0 | 102 |
| 33 | Pd(CH$_3$CO$_2$)$_2$ | 0.10 | LiCl | 10.2 | 10.2 | 7.4 | 73 | 39.8 | 89 |
| 34 | Pd(CH$_3$CO$_2$)$_2$ | 0.10 | LiCl | 15.3 | 15.3 | 5.8 | 57 | 44.5 | 99 |
| 35 | Pd(CH$_3$CO$_2$)$_2$ | 0.10 | LiCl | 20.1 | 20.1 | 5.2 | 52 | 48.6 | 108 |
| 36 | Pd(CH$_3$CO$_2$)$_2$ | 0.10 | LiCl | 26.2 | 26.2 | 4.3 | 43 | 42.5 | 95 |
| 37 | Pd(CH$_3$CO$_2$)$_2$ | 0.10 | LiCl | 120 | 120 | 0.77 | 7.7 | 60.2 | 134 |
| 38 | Pd(CH$_3$CO$_2$)$_2$ | 0.10 | LiCl | 125 | 125 | 0.82 | 8.2 | 61.26 | 146 |

TABLE 2-continued

| Ex. No. | palladium(II) salt source | mM | added chloride source | mM | total chloride mM | rate mmol l·s | Pd TF s$^{-1}$ | C$_2$H$_4$ reacted mmol | % theory |
|---|---|---|---|---|---|---|---|---|---|
| 39 | Pd(CH$_3$CO$_2$)$_2$ | 0.10 | LiCl | 155 | 155 | 0.62 | 6.2 | not available | |
| 40 | PdCl$_2$ | 1.00 | LiCl | 300 | 302 | 2.08 | 2.08 | 66.0 | 147 |
| 41 | Pd(CH$_3$CO$_2$)$_2$ | 0.10 | LiCl | 600 | 600 | 0.07 | 0.67 | 82.7 | 184 |
| 42 | PdCl$_2$ | 10.0 | LiCl | 2000 | 2020 | 0.55 | 0.055 | 60.7 | 135 |

EXAMPLE 43

Oxidation of ethylene with 0.30M {Li$_3$H$_3$PMo$_9$V$_3$O$_{40}$} having 0.010 mM palladium(II) and 5.0 mM chloride: The procedure was the same as Example 31 with the exception that the palladium(II) catalyst concentration was 0.10 millimolar (1/10 the concentration of Example 31). The initial ethylene reaction rate was 0.96 mmol l$^{-1}$ s$^{-1}$, corresponding to a palladium turnover frequency of 96 s$^{-1}$.

Figure 2:
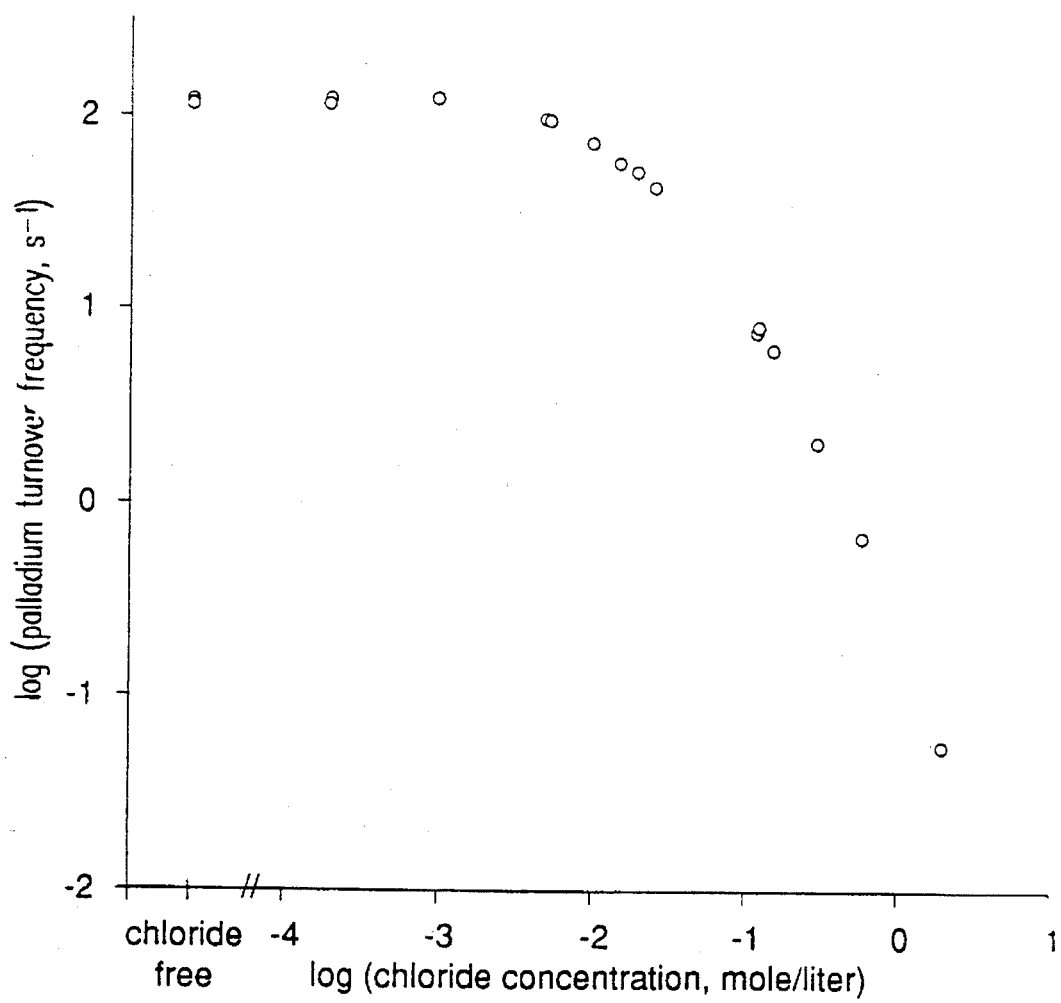
FIG. 2 is a scatter plot, on logarithmic axes, of initial palladium turnover frequencies vs. chloride ion concentrations for palladium catalyzed ethylene oxidations by 0.30M $\{Li_3H_3PMo_9V_3O_{40}\}$ solutions containing various concentrations of chloride ions. The plotted data correspond to Example 24–42, as listed in Table 2.

Comparison to Example 31 (Table 2) confirms that the ethylene reaction rate is first-order dependent on (proportional to) the palladium(II) catalyst concentration; the palladium turnover frequency is the same. It also demonstrates that the fastest reaction rates of Table 2 and FIG. 2 are not limited by by the rate of ethylene dissolution (mass transfer) into the catalyst solution, but instead manifest the chemical kinetics of the catalytic reaction.

FIG. 1 is an overlay plot of the ethylene consumption vs. time profiles for Examples 25, 32, and 34. The slope of such a profile is the reaction rate. Since the initial reaction rate is proportional to the initial palladium(II) catalyst concentration, the initial reaction rate (the initial slope) indicates the activity of the initial palladium(II) catalyst. Later reaction rates, relative to the initial reaction rate, indicate the extent to which the initial palladium(II) catalyst activity is preserved through the reaction.

FIG. 1 shows that the reaction rate of Example 25, using chloride-free solution, decelerates from its initial rate beyond about 50% conversion of the vanadium(V) to vanadium(IV). (That is, beyond about 22.5 millimoles of ethylene consumed; see reaction (12)). This rate decay indicates a decreasing activity of the initial palladium(II) catalyst charge. However, at least some catalyst activity persisted to complete the conversion of the vanadium(V) to vanadium(IV) (~45 millimoles of ethylene consumed).

The ethylene consumption vs. time profiles for the replicate chloride-free reactions of Examples 24, 25, 26, and 27, using 0.10 mM Pd(CH$_3$CO$_2$)$_2$ precatalyst, all exhibited essentially the same rate decay profile. Example 28, using 0.10 mM PdCl$_2$ precatalyst, and Example 29, using 0.10 mM Pd(CH$_3$CO$_2$)$_2$ precatalyst with 0.20 mM LiCl, exhibited similar ethylene consumption vs. time profiles showing, at best, just slightly improved palladium(II) catalyst stability in this test. Their rates still showed substantial deceleration beyond about 50% conversion of the vanadium(V). These examples demonstrate that the chloride concentration provided by PdCl$_2$ as precatalyst at 0.10 mM concentration is not sufficient to provide substantial stabilization of the initial palladium(II) catalyst activity to high conversion of the vanadium(V) oxidant in this test.

In contrast, the ethylene consumption vs. time profiles shown in FIG. 1 for Example 32, with 5.4 mM HCl added, and Example 34, with 15.3 mM LiCl added, both using Pd(CH$_3$CO$_2$)$_2$ precatalyst, are essentially linear, showing no significant rate deceleration to greater than 90% conversion of the vanadium(V) to vanadium(IV) (to at least 40 millimoles of ethylene consumed). The figure thus shows that substantial stabilization of the initial palladium(II) catalyst activity can be obtained in the instant invention by adding millimolar and centimolar concentrations of chloride ions.

Examples 31 using LiCl to provide about the same chloride ion concentration as provided by HCl in Example 32 exhibited essentially the same ethylene consumption vs. time profile as shown for Example 27 in FIG. 1. Example 32 demonstrates that, contrary to the teaching of the Matveev patents, a hydrohalic acid, specifically HCl, may be beneficially used in the inventive catalyst solution.

All of the Examples in Table 2 having at least millimolar concentrations of chloride ions showed improved stabilization of the initial palladium(II) catalyst activity to high conversion of vanadium(V) compared to the Examples which were free of chloride. All Examples having at least 5 millimolar chloride ion concentration showed no significant rate deceleration until at least 90% conversion of the theoretical vanadium(V) oxidizing equivalents initially present in the solution.

Improved preservation of palladium catalyst activity in catalyst solutions and processes comprising chloride ions is also manifested in processes which repeatedly cycle the catalyst solution between ethylene reactions and dioxygen reactions (two-stage mode). Under conditions in which the ethylene reaction rate of chloride-free solutions decays from cycle to cycle until only a substantially depressed rate is sustained, or the reaction even effectively ceases, the ethylene reaction rate of solutions comprising centimolar chloride ions is sustained from cycle to cycle.

FIG. 2 plots, on logarithmic axes, the initial palladium turnover frequency vs. chloride concentration for the Examples in Table 2. The palladium(II) catalyst activity is seen to be increasingly inhibited by increasingly higher chloride ion concentrations above millimolar levels.

However, little inhibition of the palladium(II) catalyst activity is seen at millimolar chloride concentrations and only modest inhibition is seen at centimolar chloride concentrations. Such inhibition can be readily compensated by adjusting the palladium(II) catalyst concentration to achieve the desired volumetric reaction rate. As seen in FIG. 1, although catalyst solutions with millimolar to centimolar chloride concentrations may provide initially slower reaction rates compared to catalyst solutions free of chloride, their enhanced maintenance of the initial rate may none-the-less provide for faster completion of the conversion of the vanadium(V) oxidizing equivalents.

At the highest chloride ion concentrations in FIG. 2, the log (palladium turnover frequency) vs. log (chloride ion concentration) slope reaches the limiting value of −2. That is, the palladium(II) catalyst activity becomes inversely dependent on the square of the chloride ion concentration. (The smooth dependence of turnover frequency on chloride ion concentration over Examples 40, 41, and 42, having palladium(II) concentrations of 1.00 mM, 0.10 mM, and 10.0 mM respectively, confirms that these rates are proportional to palladium(II) concentration and, therefore, reflect palladium(II) catalyst activity.) This limiting high chloride concentration dependence is the same chloride concentration dependence exhibited by the Wacker system, eq (6), which uses a similarly high chloride concentration supplied by copper chlorides. In aqueous solutions having such high chloride ion concentrations, palladium(II) exists as the tetrachloropalladate, $PdCl_4^=$, which must dissociate two chlorides to productively bind and react olefin.

The rate law for ethylene oxidation over the full range of chloride concentrations in FIG. 2 conforms to the following form:

$$-d(C_2H_4)/dt = k_0[Pd(H_2O)_4^{2+}][C_2H_4] +$$
$$k_1[PdCl(H_2O)_3^+][C_2H_4] +$$
$$k_2[PdCl_2(H_2O)_2][C_2H_4] +$$
$$k_3[PdCl_3(H_2O)^-][C_2H_4]/[Cl^-] +$$
$$k_4[PdCl_4^=][C_2H_4]/[Cl^-]^2$$

The concentrations of the various palladium(II) species will be governed by the chloride ion concentration and the equilibrium constants, under the reaction conditions, for the equilibria between these palladium species, shown in equation (18). The rate constants correspond to the catalytic activities (turnover frequencies) of the various palladium(II) species under the reaction conditions. With low or zero chloride ion concentration, tetraaquopalladate, $Pd(H_2O)_4^{2+}$, is essentially the only species present. It is the most active palladium(II) catalyst and gives the highest palladium turnover frequencies seen in FIG. 2. At high chloride concentrations, tetrachloropalladate, $PdCl_4^=$, is the dominant species present. It is not only much less active ($k_4 \ll k_0$) but is severely inhibited by the high chloride ion concentrations required for its formation.

The present invention does not require the high chloride concentrations which the Wacker system requires for the effective functioning of its copper chloride co-catalyst system. Thereby, it can provide stable palladium catalyst activities (turnover frequencies) which are one or more orders of magnitude greater than that of the Wacker system by using chloride ion concentrations which are one or more orders of magnitude less than those of the Wacker system.

Also noteworthy in Table 2 is the consumption of ethylene in excess of the vanadium(V) oxidizing capacity of solutions having chloride ion concentrations greater than 100 millimolar. This indicates that at these chloride concentrations the palladium catalyst is competent to catalyze reduction of a fraction of the molybdenum(VI) in the phosphomolybdovanadate polyoxoanions to molybdenum(V). Accordingly, we anticipate that the addition of chloride ions will be useful in palladium catalyst solutions and processes using polyoxoanions free of vanadium (for example, $PMo_{12}O_{40}^{3-}$ and $PW_6Mo_6O_{40}^{3-}$).

EXAMPLES 44–61

Oxidation of ethylene with 0.30M $\{Na_pH_{(5-p)}PMo_{10}V_2O_{40}\}$ solutions having various hydrogen ion and chloride ion concentrations: In each of these examples, a palladium catalyst solution was prepared by dissolving $Pd(CH_3CO_2)_2$ to 0.10 mM concentration in 0.30M $\{Na_pH_{(5-p)}PMo_{10}V_2O_{40}\}$ (from Examples 10, 12, 13, 14, 15, and 16) and, in some examples, also adding NaCl, as indicated in Table 3. 100 milliliters of each catalyst solution was reacted at 120° C. with ethylene at 150 psi partial pressure in Reactor #3 using an impeller stirring rate of about 2000 RPM, usually until ethylene consumption ceased. In some of these examples, the reaction was repeated with 100 milliliters virgin catalyst solution using an impeller stirring rate of about 3000 RPM.

Figure 3:
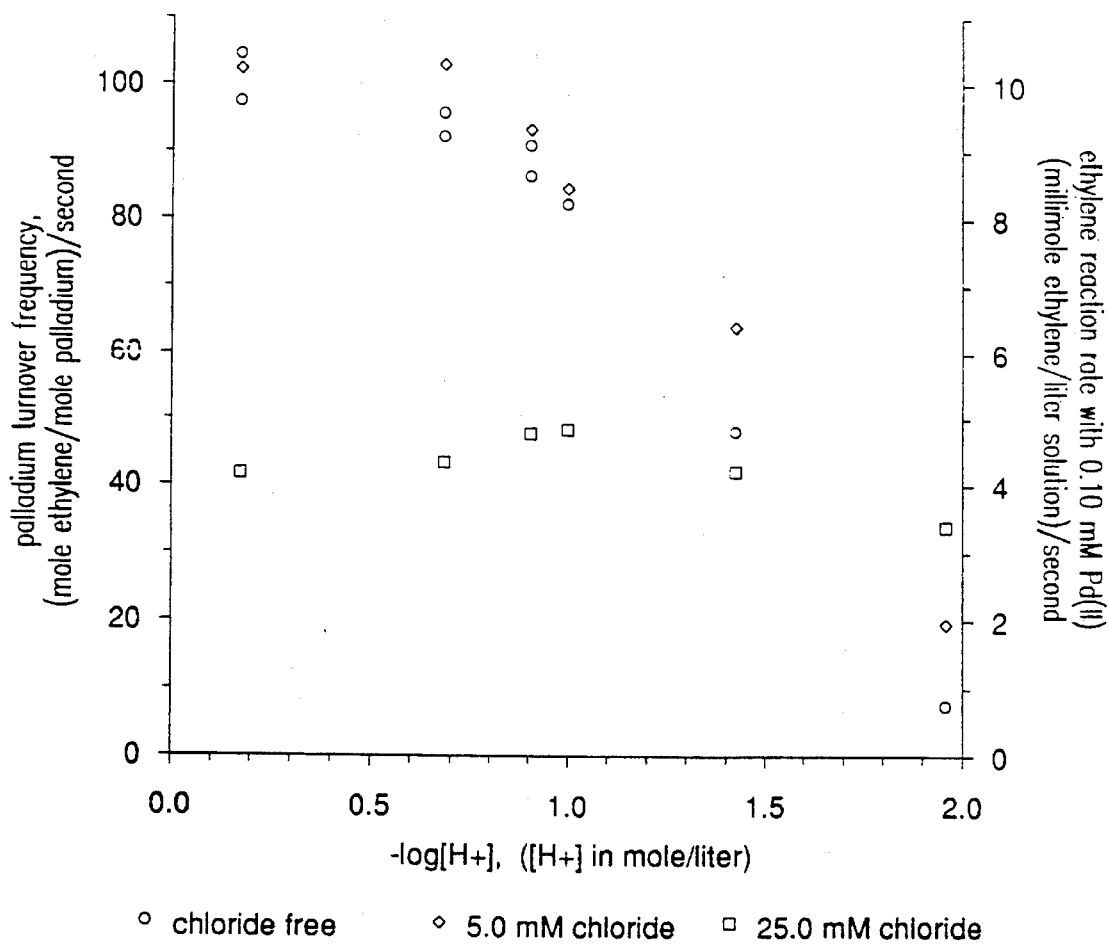
FIG. 3 is a scatter plot of measured palladium catalyst turnover frequencies vs. $-\log[H^+]$ (the negative base 10 logarithm of the hydrogen ion concentration in moles per liter) for palladium catalyzed ethylene oxidations by 0.30M $\{Na_pH_{(5-p)}PMo_{10}V_2O_{40}\}$ solutions containing various concentrations of chloride ions. The plotted data correspond to Examples 44–61, listed in Table 3.

Table 3 lists the sodium countercation balance, p, and hydrogen ion concentration, $-\log[H^+]$, of the phosphomolybdovanadate solution, the millimolar NaCl concentration, the initial ethylene reaction rate and palladium turnover frequency, and the ethylene consumption. FIG. 3 plots the initial ethylene reaction rates and palladium turnover frequencies of these Examples vs. the $-\log[H^+]$ of their catalyst solutions.

TABLE 3

| Ex. No. | $\{Na_pH_{(5-p)}PMo_{10}V_2O_{40}\}$ p | $-\log[H+]$ | [NaCl] mM | RPM | rate mmol $l \cdot s$ | Pd TF $s^{-1}$ | $C_2H_4$ reacted mmoles | % theory |
|---|---|---|---|---|---|---|---|---|
| 44 | 2 | 0.18 | 0 | 2050 | 10.4 | 104 | 32.9 | 110% |
|   |   |   |   | 3010 | 9.7 | 97 | 31.8 | 106% |
| 45 | 4 | 0.69 | 0 | 2060 | 9.2 | 92 | 28.7 | 96% |
|   |   |   |   | 2980 | 9.6 | 96 | 28.9 | 96% |
| 46 | 4.40 | 0.91 | 0 | 2030 | 8.6 | 86 | 28.0 | 93% |
|   |   |   |   | 3020 | 9.1 | 91 | 27.3 | 91% |
| 47 | 4.47 | 1.00 | 0 | 2050 | 8.2 | 82 | 25.1 | 84% |
| 48 | 4.80 | 1.43 | 0 | 2050 | 4.8 | 48 | 25.0 | 83% |
| 49 | 4.94 | 1.96 | 0 | 2050 | 0.7 | 7 | 23.0 | 77% |
| 50 | 2 | 0.18 | 5.0 | 2060 | 10.2 | 102 | 35.2 | 117% |
| 51 | 4 | 0.69 | 5.0 | 2080 | 10.3 | 103 | 29.1 | 97% |
| 52 | 4.40 | 0.91 | 5.0 | 2040 | 9.3 | 93 | 25.5 | 85% |
| 53 | 4.47 | 1.00 | 5.0 | 2050 | 8.5 | 85 | 25.6 | 85% |
| 54 | 4.80 | 1.43 | 5.0 | 2060 | 6.4 | 64 | 23.6 | 79% |
| 55 | 4.94 | 1.96 | 5.0 | 2050 | 2.0 | 20 | 21.2 | 71% |
| 56 | 2 | 0.18 | 25.0 | 2070 | 4.2 | 42 | 38.2 | 127% |
| 57 | 4 | 0.69 | 25.0 | 2070 | 4.3 | 43 | 30.5 | 102% |
| 58 | 4.40 | 0.91 | 25.0 | 2040 | 4.8 | 48 | 28.7 | 96% |
| 59 | 4.47 | 1.00 | 25.0 | 2030 | 4.8 | 48 | 28.1 | 94% |
| 60 | 4.80 | 1.43 | 25.0 | 2040 | 4.2 | 42 | 24.1 | 81% |

TABLE 3-continued

| Ex. No. | {Na$_p$H$_{(5-p)}$PMo$_{10}$V$_2$O$_{40}$} | | [NaCl] mM | RPM | rate mmol l · s | Pd TF s$^{-1}$ | C$_2$H$_4$ reacted | |
|---|---|---|---|---|---|---|---|---|
| | p | −log[H+] | | | | | mmoles | % theory |
| 61 | 4.94 | 1.96 | 25.0 | 2060 | 3.4 | 34 | 23.9 | 75% |

Each of Examples 44, 45, and 46 show ethylene reaction rates that are not significantly different between otherwise identical reactions using impeller stirring rates of about 2000 RPM and about 3000 RPM. This confirms that the fastest reaction rates in Table 3 and FIG. 3 are not limited by dissolution (mass transfer) of ethylene into the catalyst solution, but represent the chemical kinetics of catalysis under these reaction conditions.

Examples 44–49 show that in chloride-free catalyst solutions, the palladium catalyst activity is maximal at hydrogen ion concentrations greater than 0.10 moles/liter (−log[H$^+$] <1.0) and decreases precipitously as the hydrogen ion concentration is decreased below 0.10 moles/liter (−log[H$^+$] <1.0). This is plausibly attributed to the dissociation of protons from the most active palladium(II) catalyst, tetraaquopalladate, Pd(H$_2$O)$_4^{2+}$ (reportedly having two acid dissociation constants with pK$_a$~2) to give relatively inactive hydroxo-aquo palladium (II) species.

The Examples in Table 3 (FIG. 3) having −log[H$^+$]<1.0 again show that palladium catalyst activity is not significantly inhibited by chloride ions at 5 mM concentration, and is 40–60% inhibited by chloride ions at 25 mM concentration. (These are essentially the same responses as with 0.30M {Li$_3$H$_3$PMo$_9$V$_3$O$_{40}$} seen in the Examples of Table 2 (FIG. 2).) Analogous to FIG. 1, the ethylene consumption vs. time profiles of these reactions using solutions with 5.0 mM and 25 mM chloride concentrations manifested substantial stabilization of the initial palladium(II) catalyst activity through the reaction as compared to the corresponding reactions of chloride-free solutions.

The Examples in Table 3 also show that, in contrast to the inhibition by 25 mM chloride in solutions having −log[H$^+$]<1.0, palladium catalyst activity in solutions having −log[H$^+$]~2.0 is surprisingly promoted by the addition of chloride ions up to at least 25 mM concentration. FIG. 3 shows that while chloride-free solutions give precipitously decreasing palladium activity as the hydrogen ion concentration is decreased below 0.10M to about 0.01M (−log[H$^+$]>1.0 to about 2.0), solutions with 5 mM chloride give less severely decreasing palladium activity and solutions with 25 mM chloride give little significant decrease in palladium activity.

This promotion of palladium catalyst activity by chloride at −log[H$^+$]>1 is plausibly attributed to the formation of chloro-aquo palladium(II) species (equation (18)) which have higher pK$_a$'s than tetraaquopalladate, reflecting their lower positive charge. Accordingly, these chloro-aquo palladium(II) species do not dissociate protons to give catalytically less active hydroxo-species until higher −log[H$^+$] than does tetraaquopalladate. As the chloride ion concentration is further increased above 25 mM, the palladium(II) will eventually become PdCl$_3^-$ and PdCl$_4^=$ and its catalytic activity will then again be inhibited by increasing chloride concentration, as indicated in the above rate equation.

Accordingly, the palladium(II) catalyst activity dependence on chloride ion concentration at a −log[H$^+$]>1.0 has a maximum at chloride ion concentrations greater than zero (in contrast to the chloride ion concentration dependence shown in FIG. 2 for −log[H$^+$]<1.0). The maximum palladium(II) catalyst activity will be at increasingly higher chloride ion concentration as the hydrogen ion concentration of the solution is further diminished below 0.10 mole/liter (−log[H$^+$] increasingly greater than 1.0). For example, FIG. 2 shows that 5 mM chloride provides greater activity than 25 mM chloride at −log[H$^+$]≅1.4, and that 25 mM chloride provides greater activity than 5 mM chloride at −log[H$^+$] ≅2.0. The chloride ion concentration which provides maximal palladium(II) catalyst activity at any set hydrogen ion concentration, as well as the hydrogen ion concentration which provides maximal palladium(II) catalyst activity at any set chloride ion concentration, can be readily determined by routine experimentation, using, for example, the techniques exemplified herein.

The Examples in Table 3 also show that as the hydrogen ion concentrations is decreased (−log[H$^+$] is increased), particularly at hydrogen ion concentrations less than 0.10 (−log[H$^+$]>1), the ethylene reacted appears reduced below the theoretical capacity of the initial vanadium(V) concentration, whether the solution is chloride-free or contains up to 25 mM chloride. (See likewise Examples 62–65 and FIG. 4.) While the solutions containing 25 mM chloride all showed comparable initial reaction rates, only the solutions with −log[H$^+$]<1.0 gave sufficient preservation of the initial rate to complete conversion of the vanadium(V) (to 30 millimoles ethylene consumed.)

Accordingly, in some embodiments of the present invention, the hydrogen ion concentration is preferably at least 0.10 moles/liter (−log[H$^+$]<1), even though the chloride ion concentration may be sufficient to provide a comparable initial palladium catalyst activity at hydrogen ion concentrations less than 0.10 moles/liter. The palladium(II) catalyst activity is most stable when the aqueous solution comprises both chloride ions and a concentration of hydrogen ions greater than 0.10 moles/liter. Usually, the greater the concentration of hydrogen ions (the more acidic the solution), the lesser is the concentration of chloride ions required to provide the desired stability of palladium catalyst activity.

EXAMPLES 62–65

Oxidation of ethylene with 0.30M {Na$_p$H$_{(6-p)}$PMo$_9$V$_3$O$_{40}$} solutions having various hydrogen ion and containing 25 mM chloride: In each of these examples, a palladium catalyst solution was prepared containing 0.10 mM Na$_2$PdCl$_4$ and 24.6 mM NaCl in 0.30M {Na$_p$H$_{(6-p)}$PMo$_9$V$_3$O$_{40}$} (from Examples 17, 18, 19, and 20). 100 milliliters of each catalyst solution was reacted at 120° C. with ethylene at 150 psi partial pressure in Reactor #3 using an impeller stirring rate of about 2000 RPM until ethylene consumption ceased. Table 4 lists the sodium countercation balance, p, and hydrogen ion concentration, −log[H$^+$], of the phosphomolybdovanadate solution, the initial ethylene reaction rate and palladium turnover frequency, and the ethylene consumption.

TABLE 4

| Example | {Na$_p$H$_{(6-p)}$PMo$_9$V$_3$O$_{40}$} | | rate mmol l · s | Pd TF s$^{-1}$ | C$_2$H$_4$ reacted | |
|---|---|---|---|---|---|---|
| | p | −log[H+] | | | mmoles | % theory |
| 62 | 3 | 0.45 | 3.3 | 33 | 43.7 | 97 |
| 63 | 4.2 | 1.00 | 3.7 | 37 | 44.1 | 98 |
| 64 | 4.7 | 1.41 | 3.4 | 34 | 38.8 | 86 |
| 65 | 5 | 1.96 | 2.3 | 23 | 35.6 | 79 |

Table 4 shows again that centimolar chloride ion concentrations can provide initial palladium(II) catalyst activities in solutions with −log[H$^+$]'1 comparable to those obtained in solutions with −log[H$^+$]<1. It also shows again that as −log[H$^+$] is increased >1, the ethylene consumption appears reduced below the theoretical capacity of the initial vanadium(V) concentration, even in solutions containing 25 mM chloride.

Figure 4:
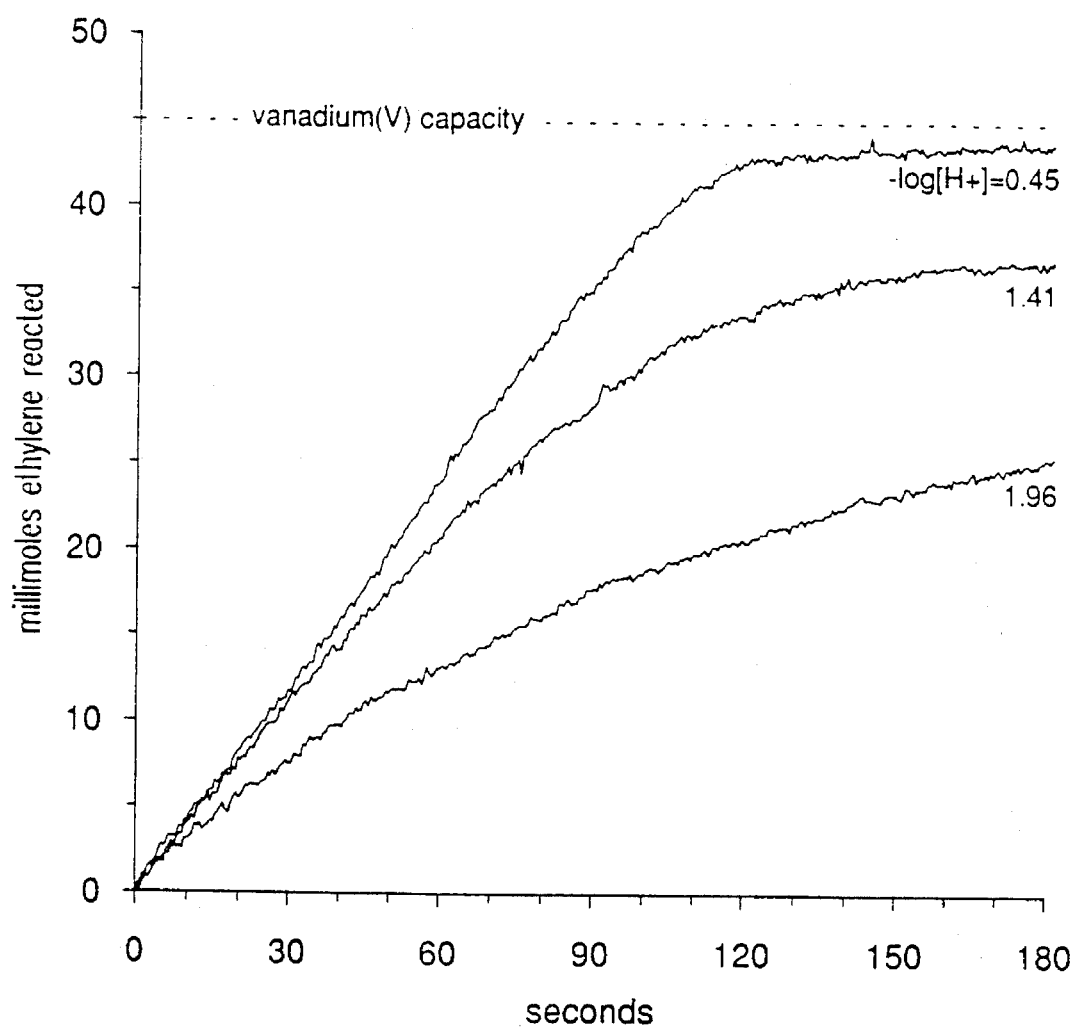
FIG. 4 is an overlay plot of ethylene consumptions vs. time in palladium catalyzed ethylene oxidations by 0.30M $\{Na_pH_{(6-p)}PMo_9V_3O_{40}\}$ solutions having various hydrogen ion concentrations (various p) and 25 millimolar chloride ion concentration. The plotted reactions are further described at Examples 62, 64, and 65 (Table 4).

FIG. 4 is an is an overlay plot of the ethylene consumption vs. time profiles for Examples 62, 64, and 65. (Example 63's profile is substantially the same as Example 62's and is omitted from the Figure for clarity). The figure shows that as the −log[H$^+$] is increased >1, the initial reaction rate increasingly decelerates over the course of the reactions, indicating increased deactivation of initial palladium(II) catalyst activity. This results ultimately in ceased ethylene consumption short of theory on the initial vanadium(V) oxidant capacity in the reactions with −log[H$^+$]>1. While the solutions in Examples 62–65 all showed comparable initial reaction rates, only the solutions with −log[H$^+$]<1.0 gave sufficient preservation of the initial rate to complete conversion of the vanadium(V) (to about 45 millimoles ethylene consumed.)

More rigorous and discriminating tests of catalyst stability (for example. multipass ethylene-dioxygen reactions) reveal that even among solutions with −log[H$^+$]<1.0, palladium(II) catalyst stability is favored by greater hydrogen ion concentrations. That is, 0.30M {Na$_3$H$_3$PMo$_9$V$_3$O$_{40}$} provides for increased preservation of initial palladium(II) activity compared to 0.30M {Na$_{4.2}$H$_{1.8}$PMo$_9$V$_3$O$_{40}$} (which was not markedly revealed in the test of Examples 62–65), and 0.30M {Na$_p$H$_{(5-p)}$PMo$_{10}$V$_2$O$_{40}$} with p<3 would provide still further increased catalyst stability. Viewed another way, the greater the concentration of hydrogen ions (the more acidic the solution), the lesser is the concentration of chloride ions required to provide the same degree of palladium (II) catalyst stability.

EXAMPLE 66

Oxidation of ethylene with chloride-free 0.30M {Na$_3$H$_3$PMo$_9$V$_3$O$_{40}$}: A palladium catalyst solution was prepared containing 0.076 mM Pd(CH$_3$CO$_2$)$_2$ in chloride-free 0.30M {Na$_3$H$_3$PMo$_9$V$_3$O$_{40}$} prepared from V$_2$O$_5$ as in Example 17. 100 milliliters of the solution was reacted at 120° C. with ethylene at 150 psi partial pressure in Reactor #2 using an impeller stirring rate of about 2000 RPM. The initial volumetric ethylene reaction rate was 7.6 mmol l$^{-1}$ s$^{-1}$, corresponding to a palladium turnover frequency of 100 s$^{-1}$. Beyond about 10 millimoles of ethylene reacted (~25% conversion of the initial vanadium(V) oxidizing equivalents) the reaction rate increasingly decelerated and the reaction required about 240 seconds complete its consumption of ethylene at 41.8 millimoles (corresponding to 93% vanadium(V) conversion.)

EXAMPLE 67

Oxidation of ethylene with 0.30M {Na$_3$H$_3$PMo$_9$V$_3$O$_{40}$} solution containing 3 mM chloride provided as an impurity in the starting materials used for its preparation: The procedure was the same as in Example 66 with the exception that the 0.30M {Na$_3$H$_3$PMo$_9$V$_3$O$_{40}$} was prepared from commercial solid NaVC$_3$ as in Example 22, and analyzed for 3 mM chloride (Example 23). The initial volumetric ethylene reaction rate was 8.1 mmol l$^{-1}$ s$^{-1}$, corresponding to a palladium turnover frequency of 107 s$^{-1}$. The reaction rate decelerated only slightly over the course of the reaction, which completed its consumption of ethylene at 42.7 millimoles (95% vanadium(V) conversion) within 70 seconds.

Comparison with Example 66 demonstrates that chloride ions provided as an impurity in a starting material used to prepare the polyoxoanion oxidant are effective for providing improved stability of palladium catalyst activity.
Butene reaction:

The following example shows a catalyst solution within the scope of this invention used in a process for the oxidation of 1-butene to 2-butanone within the scope of this invention. The 1-butene reaction was conducted in a 300 ml Hastelloy C stirred tank autoclave reactor equipped similarly to the previously described reactors used for the preceding examples of ethylene reactions. The volumetrically calibrated 1-butene reservoir and its feed lines to the reactor were heated to keep the contained 1-butene in the gas state. The reaction was conducted in fed-batch mode by the methods described for the ethylene reactions.

EXAMPLE 68

Oxidation of 1-butene with 0.30M [Li$_3$H$_3$PMo$_9$V$_3$O$_{40}$]: A catalyst solution was prepared containing 0.60 mM Pd(CH$_3$CO$_2$)$_2$ and 30 mM LiCl dissolved in 0.30M {Li$_3$H$_3$PMo$_9$V$_3$O$_{40}$} (Example 21), having −log[H$^+$]=0.38.

150 milliliters of this catalyst solution was reacted at 130° C. with 1-butene at 200 psi partial pressure using an impeller stirring rate of about 2000 RPM. The initial volumetric rate of 1-butene reaction was 5.9 mmol l$^{-1}$s$^{-1}$, corresponding to a palladium turnover frequency of 10 s$^{-1}$. The stirring was stopped 60 seconds after its initiation to stop the reaction. 26 millimoles of 1-butene were consumed within that time, giving 2-butanone as the predominant product.
Multiple Pass Ethylene-Dioxygen reactions:

Example 69 through 72 show processes for oxidation of an olefin to a carbonyl product within the scope of this invention, specifically exemplifying multiple-pass processes for oxidation of ethylene to acetaldehyde with intermediate reoxidation of reduced polyoxoanion solution by reaction with dioxygen. These reactions were conducted in a glass stirred tank autoclave reactor having 750 ml internal volume, equipped with a hollow shaft stirring impeller fitted with a multi-bladed flat disk turbine, coaxial with the cylindrical internal autoclave volume. The hollow shaft had a hole high in internal volume for gas inlet and another at the impeller turbine for efficient dispersion of the gas phase through the liquid phase. The stirring impeller was magnetically coupled to magnets belted to a rheostated direct current electric motor. The autoclave was fitted with a vertical baffle which extended along the internal wall through the unstirred gas-liquid interface. The autoclave was double walled with a jacket for circulation of heating fluid from a thermostated recirculating bath. Volumetrically calibrated reservoirs for ethylene and dioxygen delivery were connected to the autoclave via feed-forward pressure regulators.

The ethylene reactions were conducted in fed-batch mode, with a batch of catalyst solution and a continuous regulated feed of ethylene from higher pressure in the reservoir into the autoclave to maintain the set autoclave pressure. Thermocouples and pressure transducers monitored the temperatures and pressures of the reaction mixture in the autoclave and of the ethylene in the reservoir, and a magnetic-sensing tachometer monitored the impeller revolution rate. These transducers were all interfaced to a computer system for continuous data acquisition as a function of time. Reservoir volume, pressure, and temperature data were converted to moles of ethylene in the reservoir using a non-ideal gas equation incorporating the compressibility of ethylene.

For example, 150 milliliters of the indicated catalyst solution was charged to the autoclave and the gas phase in the autoclave was charged to 1 atmosphere dinitrogen. The sealed autoclave was heated to 120° C. bring the stirred solution to 120° C. and the autogenic pressure at this temperature was noted. With very gentle stirring of the solution, ethylene was regulated into the autoclave to give a total autoclave pressure equal to the autogenic pressure plus an ethylene partial pressure of 130 psia. With the autoclave open to the forward regulated total pressure from the reservoir, the reaction was initiated by increasing the impeller stirring to the indicated rate. The ethylene reaction proceeded under constant pressure while reservoir temperature and pressure data was collected. The decrease in moles of ethylene in the reservoir was taken to correspond to the moles of ethylene reacted.

The first pass ethylene reaction was allowed to proceed unit 40 millimoles of ethylene was consumed by reaction. At that time, the ethylene reaction was essentially terminated by stopping the stirring. Subsequent passes of ethylene reactions were allowed to proceed for the same amount of time as the first pass and their ethylene consumptions within that time were recorded.

Immediately following each ethylene reaction, the gas space in the reactor was flushed with nitrogen for 3–4 minutes, after which oxygen was regulated into the autoclave to give a total autoclave pressure equal to the autogenic pressure plus a dioxygen partial pressure of 130 psia. With the autoclave open to the forward regulated total pressure from the dioxygen reservoir, the reaction was initiated by increasing the impeller stirring to 2000 RPM. Dioxygen reactions were allowed to proceed for 1 minute, after which the stirring was stopped and the gas space in the reactor was again flushed with nitrogen for 3–4 minutes. The reaction solution temperature was maintained at 120° C. throughout this operation. Subsequent passes of ethylene reactions immediately followed.

EXAMPLE 69

Multiple-pass ethylene oxidation reactions with chloride-free 0.30M $\{Li_3H_3PMo_9V_3O_{40}\}$ under chemical kinetics control: 150 milliliters of a palladium catalyst solution containing 0.15 mM Pd $(CH_3CO_2)_2$ in 0.30M $\{Li_3H_3PMo_9V_3O_{40}\}$ (Example 21) was reacted with ethylene over 15 passes by the procedure described above using an impeller stirring rate of 2000 RPM. This stirring rate was independently confirmed to provide gas-liquid mixing sufficient to avoid any gas-liquid diffusion limitation on the reaction rate.

In the first pass ethylene reaction, 40 millimoles ethylene was reacted in 30 seconds. Over the next seven passes, the amount of ethylene reacted in 30 seconds decreased to about 25 millimoles. Over the last eight passes, the amount of ethylene reacted in 30 seconds remained constant at about 25 millimoles.

This example demonstrates that, at best, about 60% of the initial palladium(II) catalyst activity could be sustained in this chloride-free solution under these multipass reaction test conditions.

EXAMPLE 70

Multiple-pass ethylene oxidation reactions with 0.30M $\}Li_3H_3PMo_9V_3O_{40}\}$ containing 5.0 mM chloride, under chemical kinetics control: The procedure was the same as for Example 69 with the exception that 5.0 millimolar LiCl was added in the catalyst solution.

In the first pass ethylene reaction, 40 millimoles ethylene was reacted in 30 seconds. This is the same amount of time required to react 40 millimoles ethylene in the first pass of Example 69, showing that 5.0 millimolar chloride ions causes no significant inhibition of palladium(II) catalyst activity. In each of the following fourteen ethylene reaction passes, the amount of ethylene reacted in 30 seconds was 40 millimoles or modestly greater.

Comparison with Example 69 demonstrates that the addition of chloride in the present Example provided essentially complete preservation of the initial palladium catalyst activity under these multipass reaction test conditions.

EXAMPLE 71

Multiple-pass ethylene oxidation reactions with chloride-free 0.30M $\{Li_3H_3PMo_9V_3O_{40}\}$ under gas-liquid diffusion control: The procedure was the same as for Example 69 with the exception that the impeller stirring rate for the ethylene reactions was 500 RPM. (The impeller stirring rate for the dioxygen reactions remained at 2000 RPM.) The first pass ethylene reaction proceeded at a slower rate than that of Example 69, confirming that the reaction rate was limited by gas-liquid diffusion at this slower stirring rate.

In the first pass ethylene reaction, 40 millimoles ethylene was reacted in 100 seconds. In the second pass ethylene reaction, only 16 millimoles ethylene was reacted in 100 seconds. By the seventh pass, the amount of ethylene reacted in 100 seconds decreased to about 12.5 millimoles, and remained constant at that amount over the remaining passes.

Comparison with Example 69 demonstrates that only half as much palladium catalyst activity could be sustained in this chloride-free solution under this multipass reaction protocol when the reaction rate was limited by the rate of ethylene dissolution into the catalyst solution, than in the same solution when the mixing conditions were sufficient to avoid such limitation.

EXAMPLE 72

Multiple-pass ethylene oxidation reactions with 0.30M $\{Li_3H_3PMo_9V_3O_{40}\}$ containing 0.5 mM chloride, under gas-liquid diffusion control: The procedure was the same as for Example 71 with the exception that 5.0 millimolar LiCl was added in the catalyst solution. This procedure was the same as for Example 70 with the exception that the impeller stirring rate for the ethylene reactions was 500 RPM.

In the first pass ethylene reaction, 40 millimoles ethylene was reacted in 110 seconds. In each of the following fourteen ethylene reaction passes, the amount of ethylene reacted in 110 seconds was 40 millimoles or modestly greater.

Comparison with Example 71 demonstrates that the addition of chloride i the present Example provided for essentially complete preservation of the initial palladium catalyst activity under these multipass reaction test conditions, even when the reaction rate was limited by the rate of ethylene dissolution into the catalyst solution.

In contrast to the teachings of the Matveev patent Examples, we found that initial catalyst activity could not be stably sustained in such multipass reactions using chloride-free polyoxoanion solutions. Stable catalyst activity could be sustained at its initial level only by providing chloride in the polyoxoanion solution. Chloride could be provided by intentional addition of a chloride ion source to the polyoxoanion solution or by preparing the polyoxoanion solution from starting materials containing chloride as an impurity (see Examples 22 and 23), or both. For this purpose, the chloride ion concentration is preferably greater than twice the palladium catalyst concentration; most preferably, at least 5 millimolar.

Palladium Metal Oxidative Dissolution Reactions:

Examples 73 through 76 show processes for oxidation of palladium (0) to palladium (II) within the scope of this invention and their use in processes for oxidation of an olefin to a carbonyl product within the scope of this invention.

In each of these examples, palladium (0) metal and 100 milliliters of the indicated polyoxoanion solution were charged to the autoclave Reactor #2. described above and used for preceding examples of ethylene reactions. The gas phase in the sealed autoclave was changed to either nitrogen or dioxygen and the mixture was stirred and heated as described in each example. Following this heat treatment, the mixture was reacted with ethylene at constant 150 psi partial pressure (fed-batch mode) using an impeller stirring rate of about 2000 RPM. following the procedure previously described for the preceding examples of ethylene reactions.

By dividing the measured initial reaction rate by the known palladium (II) catalyst turnover frequency (independently measured under identical reaction conditions by using a palladium(II) salt as precatalyst) the concentration of active palladium (II) catalyst present in the solution after the heat treatment could be calculated.

EXAMPLE 73

Oxidative dissolution of palladium (0) metal by chloride-free 0.30M $\{Li_3H_3PMo_9V_3O_{40}\}$; 1.1 milligram (0.010 millimole) palladium powder (1.0–1.5 micron, surface area=1.6 $m^2/g$) and 100 milliliters a 0.30M $\{Li_3H_3PMo_9V_3O_{40}\}$ were charged to the autoclave reactor and the gas phase in the sealed autoclave was changed to 1 atmosphere dinitrogen. The stirring solution was heated to 120° C. and maintained at that temperature for 2 hours. With very gentle stirring of the solution, ethylene was then regulated into the autoclave to 150 psi partial pressure, and the ethylene reaction was initiated by increasing the impeller stirring rate to about 2000 RPM.

The initial ethylene reaction rate was 0.11 mmol $l^{-1}$ $s^{-1}$. The reaction was discontinued after 45 minutes, having consumed less than 20 millimoles ethylene (<50% conversion of vanadium (V) to Vanadium (IV)).

Examples 24–27 show ethylene reactions using the same 0.30M $\{Li_3H_3PMo_9V_3O_{40}\}$ polyoxoanion solution under the same reaction conditions provided the same molar amount of palladium, but provided as palladium (II) acetate. The average initial reaction rate for these examples is 11.6 mmol $l^{-1}$ $s^{-1}$, corresponding to a palladium turnover frequency of 116 $s^{-1}$. As seen in FIG. 1 for Example 25, these reactions consumed ethylene to the complete vanadium (V) oxidizing capacity of the solution (45 millimoles ethylene) within about 90 seconds.

Accordingly, only about 1% of the palladium (0) metal provided in the present example was oxidatively dissolved to active palladium(II) catalyst during the heat treatment prior to the ethylene reaction.

EXAMPLE 74

Oxidative dissolution of palladium(0) metal by chloride-free 0.30M $\{Li_3H_3PMo_9V_3O_{40}\}$: The procedure was the same as for Example 73 with the exception that the 2 hour heat treatment was at 170° C. The solution was cooled to 120° C. for the ethylene reaction. The initial ethylene reaction rate was 4.0 mmol $l^{-1}$ $s^{-1}$.

Comparison with Examples 24–27 shows that about 35% of the palladium(0) metal provided in the present example was oxidatively dissolved to active palladium (II) catalyst during the 2 hour, 170° C. heat treatment prior to the ethylene reaction.

EXAMPLE 75

Oxidative dissolution of palladium (0) metal by chloride-free 0.30M $\{Li_3H_3PMo_9V_3O_{40}\}$ under dioxygen: The procedure was the same as for Example 73 with the exception that the two hour heat treatment at 120° C. was conducted with 100 psi partial pressure of dioxygen using an impeller stirring speed of about 2000 RPM. After this heat treatment, the mixture was cooled to ambient temperature, the gas phase in autoclave was changed to 1 atmosphere dinitrogen, and the mixture was reheated to 120° C. for the ethylene reaction. The initial ethylene reaction rate was 0.08 mmol $l^{-1}$ $s^{-1}$. The reaction was discontinued after 45 minutes, having consumed less than 12 millimoles ethylene.

Comparison with Example 73 shows that the addition of dioxygen to a chloride free polyoxoanion solution does not significantly promote its kinetic capability to oxidatively dissolve palladium (0) metal to active palladium (II) catalyst.

EXAMPLE 76

Oxidative dissolution of palladium (0) metal by 0.30M $\{Li_3H_3PMo_9V_3O_{40}\}$ containing chloride ions: The procedure was the same as for Example 73 with the exceptions that LiCl was added in the polyoxoanion solution at 15.0 mM concentration and the ethylene reaction was initiated after only 1 hour of heat treatment at 120° C.

The initial ethylene reaction rate was 5.8 mmol $l^{-1}$ $s^{-1}$, corresponding to a palladium turnover frequency of 58 $s^{-1}$. The reaction consumed 43.4 millimoles ethylene (96% of theory on the vanadium (V) oxidizing capacity) within about 75 seconds. The reaction rate and ethylene consumption vs. time profile were essentially the same as for Example 34 (see Table 2 and FIG. 1), which used the same 0.30M {Li₃H₃PMo₉V₃O₄₀} polyoxoanion solution, containing about the same concentration of chloride ions, under the same reaction conditions and provided the same molar amount of palladium, but provided as palladium (II) acetate. This comparison demonstrates that essentially 100% of the palladium (0) metal provided in the present example was oxidatively dissolved to active palladium (II) catalyst during the heat treatment prior to the ethylene reaction.

Comparison to Example 73 demonstrates that the presence of chloride ions in the instant invention critically enables the polyoxoanion oxidant to relatively rapidly oxidize palladium (0) metal to active palladium (II) catalyst. In contrast to the teachings of the Matveev patents, specifically Matveev patents' Example 10, we found that palladium metal could not be directly and facilely used to provide a corresponding molar amount of active palladium catalyst in chloride-free polyoxoanion solutions. Chloride ions can be provided in the present invention by intentional addition of a chloride ion source to the polyoxoanion solution or by preparing the polyoxoanion solution from starting materials containing chloride as an impurity (see Example 22), or both.

The present inventions have been shown by both description and exemplification. The exemplification is only exemplification and cannot be construed to limit the scope of the invention. Persons of ordinary skill in the art will envision equivalents to the inventive solutions and processes described by the following claims which are within the scope and spirit of the claimed invention.

We claim as our invention:

1. An aqueous palladium catalyst solution for the oxidation of an olefin to a carbonyl product comprising a palladium catalyst, a polyoxoanion oxidant comprising vanadium, and chloride ions, wherein the concentration of said chloride ions is greater than twice the concentration of said palladium catalyst and at least 5 millimole per liter.

2. The solution of claim 1 wherein said chloride ions are provided as an impurity in a starting material used to prepare said polyoxoanion oxidant.

3. The solution of claim 1 wherein said polyoxoanion oxidant further comprises phosphorus and molybdenum.

4. The solution of claim 3 wherein said polyoxoanion oxidant comprises a phosphomolybdovanadate having the formula $$[H_yPMo_{(12-x)}V_xO_{40}]^{(3+x-y)-}$$

wherein $0<x<12$ and $0\leq y<(3+x)$, or mixtures thereof.

5. The solution of claim 1, 2, 3, or 4, wherein the concentration of hydrogen ions in the aqueous solution is greater than 0.10 mole per liter of solution when essentially all the oxidant is in its oxidized state.

6. The solution of claim 1, 2, 3, or 4, further comprising at least one of an olefin and a corresponding carbonyl product.

7. A process for oxidation of an olefin to a carbonyl product comprising:
reacting the olefin with an aqueous catalyst solution, wherein the aqueous catalyst solution is the solution of claim 1, 2, 3, or 4, at conditions sufficient to oxidize the olefin to a carbonyl product.

8. A process for oxidation of an olefin to a carbonyl product comprising:
reacting the olefin with an aqueous catalyst solution comprising a palladium catalyst, a polyoxoanion oxidant comprising vanadium, and chloride ions, wherein the concentration of said chloride ions is greater than twice the concentration of said palladium catalyst and at least 5 millimole per liter, at conditions sufficient to oxidize the olefin to a carbonyl product.

9. The process of claim 8 wherein said chloride ions are provided as an impurity in a starting material used to prepare said polyoxoanion oxidant.

10. The process of claim 8 wherein said polyoxoanion oxidant further comprises phosphorus and molybdenum.

11. The process of claim 10 wherein said polyoxoanion oxidant comprises a phosphomolybdovanadate having the formula $$[H_yPMo_{(12-x)}V_xO_{40}]^{(3+x-y)-}$$

wherein $0<x<12$ and $0\leq y<(3+x)$, or mixtures thereof.

12. The process of claim 8, 9, 10, or 11, wherein the olefin is ethylene and the carbonyl product is acetaldehyde.

13. The process of claim 8, 9, 10, or 11, wherein the olefin is propylene and the carbonyl product is acetone.

14. The process of claim 8, 9, 10, or 11, wherein the olefin is one of 1-butene, cis-2-butene, and trans-2-butene, or mixtures thereof, and the carbonyl product is 2-butanone.

15. The process of claim 8, 9, 10, or 11, wherein the olefin is one of 3-methyl-1-butene and 2-methyl-2-butene, or mixtures thereof, and the carbonyl product is 3-methyl-2-butanone.

16. The process of claim 8, 9, 10, or 11, wherein the olefin is 4-methyl-1-pentene and the carbonyl product is 4-methyl-2-pentanone.

17. The process of claim 8, 9, 10, or 11, wherein the olefin is cyclopentene and the carbonyl product is cyclopentanone.

18. The process of claim 8, 9, 10, or 11, wherein the olefin is cyclohexene and the carbonyl product is cyclohexanone.

19. The process of claim 8, 9, 10, or 11, further comprising contacting dioxygen with the aqueous catalyst solution.

20. The process of claim 8, 9, 10, or 11, further comprising the steps of removing the carbonyl product from the aqueous solution, reacting dioxygen with the aqueous catalyst solution at conditions sufficient to regenerate the oxidant in its oxidized state, and reacting additional olefin with the aqueous catalyst solution.

21. In an aqueous palladium catalyst solution for the oxidation of an olefin to a carbonyl product comprising a palladium catalyst and a polyoxoanion oxidant comprising vanadium, the improvement wherein the solution further comprises chloride ions at a concentration greater than twice the concentration of said palladium catalyst and at least 5 millimolar per liter.

22. In a process for oxidation of an olefin to a carbonyl product comprising reacting the olefin with an aqueous catalyst solution comprising a palladium catalyst and a polyoxoanion oxidant comprising vanadium at conditions sufficient to oxidize the olefin to a carbonyl product, the improvement wherein the solution further comprises chloride ions at a concentration greater than twice the concentration of said palladium catalyst and at least 5 millimolar per liter.

* * * * *